US012139541B2

(12) United States Patent
Gulla et al.

(10) Patent No.: US 12,139,541 B2
(45) Date of Patent: Nov. 12, 2024

(54) METHODS OF TREATING DISORDERS ASSOCIATED WITH EXCESS OR UNWANTED KILLER CELL LECTIN-LIKE RECEPTOR SUBFAMILY G MEMBER 1 (KLRG1) EXPRESSING T CELLS WITH KLRG1 DEPLETING ANTIBODIES

(71) Applicant: Abcuro, Inc., Newton, MA (US)

(72) Inventors: Stefano Vincenzo Gulla, Medford, MA (US); Kenneth Evan Thompson, Arlington, MA (US)

(73) Assignee: Abcuro, Inc., Newton, MA (US)

( * ) Notice: Subject to any disclaimer, the term of this patent is extended or adjusted under 35 U.S.C. 154(b) by 246 days.

(21) Appl. No.: 17/506,313

(22) Filed: Oct. 20, 2021

(65) Prior Publication Data

US 2022/0089747 A1   Mar. 24, 2022

Related U.S. Application Data

(62) Division of application No. 16/844,747, filed on Apr. 9, 2020, now Pat. No. 11,180,561.

(Continued)

(51) Int. Cl.
*A61K 39/395* (2006.01)
*C07K 16/28* (2006.01)

(52) U.S. Cl.
CPC ...... *C07K 16/2851* (2013.01); *C07K 2317/24* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS 10,730,950 B2 *   8/2020   Holland ............. C07K 16/2818
11,339,222 B2 *   5/2022   Greenberg ......... C07K 16/2851
(Continued)

FOREIGN PATENT DOCUMENTS

WO   2008140653 A2   11/2008
WO   2017210523 A1   12/2017
(Continued)

OTHER PUBLICATIONS

Tata et al., Combination blockade of KLRG1 and PD-1 promotes immune control of local and disseminated cancers, Oncoimmunol. 10(1): e1933808, 11 pages, doi:10.1080/2162402X.2021.1933808, 2021.*
Li et al., KLRG1 restricts memory T cell antitumor immunity, Oncotarget, 7(38):61670-61678, Aug. 2016.*
(Continued)

*Primary Examiner* — Claire Kaufman
(74) *Attorney, Agent, or Firm* — Hogan Lovells US LLP

(57) ABSTRACT

The receptor killer cell lectin-like receptor G1 (KLRG1) is expressed on T and NK cells, which binds to ligands on epithelial and mesenchymal cells. The ligand for KLRG1 has been described to be E-cadherin, N-cadherin, and R-cadherin. The present disclosure relates to and results from the discovery and characterization of antibodies that bind the extracellular domain (ECD) of KLRG1 but do not interfere with its interaction with the ligands E-cadherin, N-cadherin, and R-cadherin. The antibodies described have been derived by mouse hybridoma technology, and can be humanized by grafting their complementary determining regions (CDRs) into a human framework. The antibodies described can be used as effective therapeutic agents. Various antibodies, or antigen-binding fragments of such antibodies, along with various therapeutic and/or diagnostic methods, among other features, are provided for in the present disclosure.

19 Claims, 6 Drawing Sheets

Specification includes a Sequence Listing.

Related U.S. Application Data

(60) Provisional application No. 62/831,713, filed on Apr. 9, 2019.

(56) References Cited

U.S. PATENT DOCUMENTS

| | | |
|---|---|---|
| 2002/0155110 A1 | 10/2002 | Takahashi et al. |
| 2017/0260282 A1 | 9/2017 | Holland et al. |
| 2019/0085083 A1 | 3/2019 | Greenberg et al. |
| 2019/0292264 A1 | 9/2019 | Greenberg et al. |
| 2021/0002373 A1 | 1/2021 | Liu et al. |

FOREIGN PATENT DOCUMENTS

| | | |
|---|---|---|
| WO | 2018053264 A2 | 3/2018 |
| WO | 2020112109 A2 | 6/2020 |

OTHER PUBLICATIONS

International Search Report; WO 2020/210512 A1 (PCT/US2020/027498; filed Apr. 9, 2020); published Oct. 15, 2020.

MacCallum et al., "Antibody-antigen interactions: contact analysis and binding site topography", J. Mol. Biol. 262:732-745 (1996).

Amminmaki et al., "Crystal structure of a recombinant anti-estradiol Fab fragment in complex with the 17beta-estradiol", J. Biol. Chem. 276:36687-94 (2001).

Chen et al., "Enhancement and destruction of antibody function by somatic mutation: unequal occurrence is controlled by V gene combinatorial association", EMBO J. 14(12):2784-2794 (1995).

Henson et al., "KLRG-1-more than a marker for T cell senescence," Journal of the American Aging Association, vol. 31, No. 4, pp. 285-291 (2009).

Rosshart et al., "Interaction of KLRG1 with E-cadherin: New functional and structural insights, " European Journal of Immunology, vol. 38, No. 12, pp. 3354-3364 (2008).

\* cited by examiner

| Sample Name | IFNγ (pg/ml), replicate #1 | IFNγ (pg/ml), replicate #2 |
|---|---|---|
| CD8 positive control | 1624.09 | 1401.42 |
| Isotype | 390.02 | 355.94 |
| mAb023 | 1579.71 | 1389.6 |
| ABC_G1D01 | NA | NA |
| ABC_G1D02 | 763.71 | 628.25 |
| ABC_G1D03 | 919.95 | 772.32 |
| ABC_G1D04 | NA | NA |
| ABC_G1D05 | 804.64 | 793.9 |
| ABC_G1D06 | 656.08 | 758.43 |

SEQUENCE LISTING

```
<160> NUMBER OF SEQ ID NOS: 86

<210> SEQ ID NO 1
<211> LENGTH: 130
<212> TYPE: PRT
<213> ORGANISM: Homo sapiens
<220> FEATURE:
<221> NAME/KEY: MISC_FEATURE
<223> OTHER INFORMATION: KLRG1 extracellular domain

<400> SEQUENCE: 1

Leu Cys Gln Gly Ser Asn Tyr Ser Thr Cys Ala Ser Cys Pro Ser Cys
1               5                   10                  15

Pro Asp Arg Trp Met Lys Tyr Gly Asn His Cys Tyr Tyr Phe Ser Val
            20                  25                  30

Glu Glu Lys Asp Trp Asn Ser Ser Leu Glu Phe Cys Leu Ala Arg Asp
        35                  40                  45

Ser His Leu Leu Val Ile Thr Asp Asn Gln Glu Met Ser Leu Leu Gln
    50                  55                  60

Val Phe Leu Ser Glu Ala Phe Cys Trp Ile Gly Leu Arg Asn Asn Ser
65                  70                  75                  80

Gly Trp Arg Trp Glu Asp Gly Ser Pro Leu Asn Phe Ser Arg Ile Ser
                85                  90                  95

Ser Asn Ser Phe Val Gln Thr Cys Gly Ala Ile Asn Lys Asn Gly Leu
            100                 105                 110

Gln Ala Ser Ser Cys Glu Val Pro Leu His Trp Val Cys Lys Lys Val
        115                 120                 125

Arg Leu
    130

<210> SEQ ID NO 2
<211> LENGTH: 130
<212> TYPE: PRT
<213> ORGANISM: CYNOMOLGUS MONKEY
<220> FEATURE:
<221> NAME/KEY: MISC_FEATURE
<223> OTHER INFORMATION: KLRG1 extracellular domain

<400> SEQUENCE: 2

Leu Cys Gln Gly Ser Lys Tyr Ser Thr Cys Ala Ser Cys Pro Ser Cys
1               5                   10                  15

Pro Asp His Trp Met Lys Tyr Gly Asn His Cys Tyr Tyr Phe Ser Val
            20                  25                  30

Glu Lys Lys Asp Trp Ile Ser Ser Leu Glu Phe Cys Leu Ala Arg Asp
        35                  40                  45

Ser His Leu Leu Met Ile Thr Asp Lys Gln Glu Met Ser Leu Leu Gln
    50                  55                  60

Asp Phe Leu Ser Glu Ala Phe His Trp Val Gly Leu Arg Asn Asn Ser
65                  70                  75                  80

Gly Trp Arg Trp Glu Asp Gly Ser Pro Leu Asn Phe Ser Arg Ile Tyr
                85                  90                  95

Ser Asn Ser Leu Val Gln Thr Cys Gly Ala Ile Asn Lys Asn Ser Leu
            100                 105                 110
```

```
Gln Ala Ser Ser Cys Glu Val Ser Leu Gln Trp Val Cys Lys Lys Val
        115                 120                 125

Ser Pro
    130

<210> SEQ ID NO 3
<211> LENGTH: 728
<212> TYPE: PRT
<213> ORGANISM: Homo sapiens
<220> FEATURE:
<221> NAME/KEY: MISC_FEATURE
<223> OTHER INFORMATION: E-cadherin full length

<400> SEQUENCE: 3

Asp Trp Val Ile Pro Ile Ser Cys Pro Glu Asn Glu Lys Gly Pro
1               5                   10                  15

Phe Pro Lys Asn Leu Val Gln Ile Lys Ser Asn Lys Asp Lys Glu Gly
            20                  25                  30

Lys Val Phe Tyr Ser Ile Thr Gly Gln Gly Ala Asp Thr Pro Pro Val
        35                  40                  45

Gly Val Phe Ile Ile Glu Arg Glu Thr Gly Trp Leu Lys Val Thr Glu
    50                  55                  60

Pro Leu Asp Arg Glu Arg Ile Ala Thr Tyr Thr Leu Phe Ser His Ala
65                  70                  75                  80

Val Ser Ser Asn Gly Asn Ala Val Glu Asp Pro Met Glu Ile Leu Ile
                85                  90                  95

Thr Val Thr Asp Gln Asn Asp Asn Lys Pro Glu Phe Thr Gln Glu Val
            100                 105                 110

Phe Lys Gly Ser Val Met Glu Gly Ala Leu Pro Gly Thr Ser Val Met
        115                 120                 125

Glu Val Thr Ala Thr Asp Ala Asp Asp Val Asn Thr Tyr Asn Ala
    130                 135                 140

Ala Ile Ala Tyr Thr Ile Leu Ser Gln Asp Pro Glu Leu Pro Asp Lys
145                 150                 155                 160

Asn Met Phe Thr Ile Asn Arg Asn Thr Gly Val Ile Ser Val Val Thr
                165                 170                 175

Thr Gly Leu Asp Arg Glu Ser Phe Pro Thr Tyr Thr Leu Val Val Gln
            180                 185                 190

Ala Ala Asp Leu Gln Gly Glu Gly Leu Ser Thr Thr Ala Thr Ala Val
        195                 200                 205

Ile Thr Val Thr Asp Thr Asn Asp Asn Pro Pro Ile Phe Asn Pro Thr
    210                 215                 220

Thr Tyr Lys Gly Gln Val Pro Glu Asn Glu Ala Asn Val Val Ile Thr
225                 230                 235                 240

Thr Leu Lys Val Thr Asp Ala Asp Ala Pro Asn Thr Pro Ala Trp Glu
                245                 250                 255

Ala Val Tyr Thr Ile Leu Asn Asp Asp Gly Gly Gln Phe Val Val Thr
            260                 265                 270

Thr Asn Pro Val Asn Asn Asp Gly Ile Leu Lys Thr Ala Lys Gly Leu
        275                 280                 285

Asp Phe Glu Ala Lys Gln Gln Tyr Ile Leu His Val Ala Val Thr Asn
    290                 295                 300

Val Val Pro Phe Glu Val Ser Leu Thr Thr Ser Thr Ala Thr Val Thr
305                 310                 315                 320
```

```
Val Asp Val Leu Asp Val Asn Glu Ala Pro Ile Phe Val Pro Pro Glu
            325                 330                 335

Lys Arg Val Glu Val Ser Glu Asp Phe Gly Val Gly Gln Glu Ile Thr
            340                 345                 350

Ser Tyr Thr Ala Gln Glu Pro Asp Thr Phe Met Glu Gln Lys Ile Thr
            355                 360                 365

Tyr Arg Ile Trp Arg Asp Thr Ala Asn Trp Leu Glu Ile Asn Pro Asp
            370                 375                 380

Thr Gly Ala Ile Ser Thr Arg Ala Glu Leu Asp Arg Glu Asp Phe Glu
385                 390                 395                 400

His Val Lys Asn Ser Thr Tyr Thr Ala Leu Ile Ile Ala Thr Asp Asn
            405                 410                 415

Gly Ser Pro Val Ala Thr Gly Thr Gly Thr Leu Leu Leu Ile Leu Ser
            420                 425                 430

Asp Val Asn Asp Asn Ala Pro Ile Pro Glu Pro Arg Thr Ile Phe Phe
            435                 440                 445

Cys Glu Arg Asn Pro Lys Pro Gln Val Ile Asn Ile Ile Asp Ala Asp
            450                 455                 460

Leu Pro Pro Asn Thr Ser Pro Phe Thr Ala Glu Leu Thr His Gly Ala
465                 470                 475                 480

Ser Ala Asn Trp Thr Ile Gln Tyr Asn Asp Pro Thr Gln Glu Ser Ile
            485                 490                 495

Ile Leu Lys Pro Lys Met Ala Leu Glu Val Gly Asp Tyr Lys Ile Asn
            500                 505                 510

Leu Lys Leu Met Asp Asn Gln Asn Lys Asp Gln Val Thr Thr Leu Glu
            515                 520                 525

Val Ser Val Cys Asp Cys Glu Gly Ala Ala Gly Val Cys Arg Lys Ala
            530                 535                 540

Gln Pro Val Glu Ala Gly Leu Gln Ile Pro Ala Ile Leu Gly Ile Leu
545                 550                 555                 560

Gly Gly Ile Leu Ala Leu Leu Ile Leu Ile Leu Leu Leu Leu Leu Phe
            565                 570                 575

Leu Arg Arg Arg Ala Val Val Lys Glu Pro Leu Leu Pro Pro Glu Asp
            580                 585                 590

Asp Thr Arg Asp Asn Val Tyr Tyr Tyr Asp Glu Glu Gly Gly Gly Glu
            595                 600                 605

Glu Asp Gln Asp Phe Asp Leu Ser Gln Leu His Arg Gly Leu Asp Ala
            610                 615                 620

Arg Pro Glu Val Thr Arg Asn Asp Val Ala Pro Thr Leu Met Ser Val
625                 630                 635                 640

Pro Arg Tyr Leu Pro Arg Pro Ala Asn Pro Asp Glu Ile Gly Asn Phe
            645                 650                 655

Ile Asp Glu Asn Leu Lys Ala Ala Asp Thr Asp Pro Thr Ala Pro Pro
            660                 665                 670

Tyr Asp Ser Leu Leu Val Phe Asp Tyr Glu Gly Ser Gly Ser Glu Ala
            675                 680                 685

Ala Ser Leu Ser Ser Leu Asn Ser Ser Glu Ser Asp Lys Asp Gln Asp
            690                 695                 700

Tyr Asp Tyr Leu Asn Glu Trp Gly Asn Arg Phe Lys Lys Leu Ala Asp
705                 710                 715                 720

Met Tyr Gly Gly Gly Glu Asp Asp
            725
```

<210> SEQ ID NO 4
<211> LENGTH: 119
<212> TYPE: PRT
<213> ORGANISM: Mouse
<220> FEATURE:
<221> NAME/KEY: MISC_FEATURE
<223> OTHER INFORMATION: ABC_G1D01-VH

<400> SEQUENCE: 4

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Ile His Trp Val Lys Gln Ser His Gly Lys Ser Leu Glu Trp Ile
        35                  40                  45

Gly Phe Phe Asn Pro Lys Asn Gly Val Thr Ile Asn Asn Gln Asn Phe
    50                  55                  60

Lys Gly Lys Ala Ala Leu Thr Val Asn Lys Ser Ser Thr Ala Tyr
65                  70                  75                  80

Met Glu Leu Arg Arg Leu Thr Ser Glu Asp Ser Ala Val Tyr Tyr Cys
                85                  90                  95

Ala Arg Asp Tyr Tyr Gly Thr Ala Trp Phe Ala Tyr Trp Gly Gln Gly
            100                 105                 110

Thr Leu Val Thr Val Ser Ala
        115

<210> SEQ ID NO 5
<211> LENGTH: 112
<212> TYPE: PRT
<213> ORGANISM: Mouse
<220> FEATURE:
<221> NAME/KEY: MISC_FEATURE
<223> OTHER INFORMATION: ABC_G1D01-VK

<400> SEQUENCE: 5

Asp Ile Val Met Ser Gln Ser Pro Ser Ser Leu Ala Val Ser Val Gly
1               5                   10                  15

Glu Lys Val Thr Met Ser Cys Arg Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Phe Tyr Ser Tyr Pro Thr Phe Gly Gly Gly Thr Lys Leu Glu Ile Lys
            100                 105                 110

<210> SEQ ID NO 6
<211> LENGTH: 115
<212> TYPE: PRT
<213> ORGANISM: Mouse
<220> FEATURE:
<221> NAME/KEY: MISC_FEATURE
<223> OTHER INFORMATION: ABC_G1D02-VH

<400> SEQUENCE: 6

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Phe Ile Glu Trp Ile Lys Gln Arg Pro Gly Gln Gly Leu Glu Trp Ile
        35                  40                  45

Gly Val Ile Asn Pro Gly Ser Gly Gly Thr Asn Tyr Asn Glu Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Thr Arg Pro Gly His Phe Asp Tyr Trp Gly Gln Gly Thr Thr Leu Thr
            100                 105                 110

Val Ser Ser
        115

<210> SEQ ID NO 7
<211> LENGTH: 108
<212> TYPE: PRT
<213> ORGANISM: Mouse
<220> FEATURE:
<221> NAME/KEY: MISC_FEATURE
<223> OTHER INFORMATION: ABC_G1D02-VK

<400> SEQUENCE: 7

Glu Ile Val Leu Thr Gln Ser Pro Thr Thr Met Ala Ala Ser Pro Gly
1               5                   10                  15

Glu Lys Ile Thr Ile Thr Cys Ser Ala Ser Ser Ser Ile Ser Ser Asn
            20                  25                  30

Tyr Leu His Trp Tyr Gln Gln Lys Pro Gly Phe Ser Pro Lys Leu Leu
        35                  40                  45

Ile Tyr Lys Thr Ser Asn Leu Ala Ser Gly Val Pro Pro Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Asn Ser Ile Pro
                85                  90                  95

Arg Thr Phe Gly Gly Gly Thr Lys Leu Glu Ile Lys
            100                 105

<210> SEQ ID NO 8
<211> LENGTH: 119
<212> TYPE: PRT
<213> ORGANISM: Mouse
<220> FEATURE:
<221> NAME/KEY: MISC_FEATURE
<223> OTHER INFORMATION: ABC_G1D03-VH

<400> SEQUENCE: 8

Glu Val Gln Leu Gln Gln Ser Gly Pro Glu Leu Val Lys Pro Gly Ala
1               5                   10                  15

Ser Val Lys Met Ser Cys Lys Thr Ser Gly Tyr Thr Phe Thr Asp His
            20                  25                  30

Asn Met His Trp Leu Lys Gln Ser His Gly Lys Gly Leu Glu Trp Phe
        35                  40                  45

```
Gly Phe Ile Asn Pro Asn Thr Gly Val Thr Arg Tyr Asn Gln Lys Phe
    50                  55                  60

Asn Gly Lys Ala Thr Leu Thr Ile Asn Lys Ser Ser Thr Ala Tyr
 65                  70                  75                  80

Leu Asp Leu Arg Ser Leu Thr Ser Glu Asp Ser Ala Val Tyr Tyr Cys
                 85                  90                  95

Thr Arg Asp Tyr Tyr Gly Ser Ala Trp Phe Ala Tyr Trp Gly Gln Gly
                100                 105                 110

Thr Leu Val Thr Val Ser Ala
        115
```

<210> SEQ ID NO 9
<211> LENGTH: 112
<212> TYPE: PRT
<213> ORGANISM: Mouse
<220> FEATURE:
<221> NAME/KEY: MISC_FEATURE
<223> OTHER INFORMATION: ABC_G1D03-VK

<400> SEQUENCE: 9

```
Asp Ile Val Met Ser Gln Ser Pro Ala Ser Gln Thr Val Ser Val Gly
 1               5                  10                  15

Glu Lys Val Thr Met Ser Cys Lys Ser Ser Gln Thr Leu Leu Tyr Ser
                 20                  25                  30

Ser Asp Gln Lys Asn Tyr Leu Ala Trp Tyr Gln Lys Pro Gly Gln
             35                  40                  45

Ser Pro Lys Leu Leu Ile Tyr Trp Ala Ser Thr Arg Glu Ser Gly Val
         50                  55                  60

Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                 85                  90                  95

Tyr Tyr Asn Tyr Pro Thr Phe Gly Gly Gly Thr Lys Leu Glu Ile Lys
                100                 105                 110
```

<210> SEQ ID NO 10
<211> LENGTH: 119
<212> TYPE: PRT
<213> ORGANISM: Mouse
<220> FEATURE:
<221> NAME/KEY: MISC_FEATURE
<223> OTHER INFORMATION: ABC_G1D04-VH

<400> SEQUENCE: 10

```
Glu Val Gln Leu Gln Gln Ser Gly Pro Glu Leu Val Lys Pro Gly Ser
 1               5                  10                  15

Ser Leu Met Met Ser Cys Lys Ser Gly Tyr Thr Phe Thr Asp Tyr
                 20                  25                  30

Asn Ile His Trp Val Lys Gln Ser His Gly Lys Arg Leu Glu Trp Ile
             35                  40                  45

Gly Phe Ile Asp Pro Lys Asn Gly Gly Thr Leu Tyr Ser Glu Lys Phe
         50                  55                  60

Lys Asp Lys Ala Thr Leu Thr Ile Asn Lys Ser Ser Thr Ala Tyr
 65                  70                  75                  80

Met Glu Leu Arg Ser Leu Thr Ser Glu Asp Ser Ala Val Phe Tyr Cys
                 85                  90                  95

Ala Pro Asp Tyr Tyr Gly Ser Ala Trp Phe Ala Tyr Trp Gly Gln Gly
                100                 105                 110
```

Thr Leu Val Thr Val Ser Ala
        115

<210> SEQ ID NO 11
<211> LENGTH: 112
<212> TYPE: PRT
<213> ORGANISM: Mouse
<220> FEATURE:
<221> NAME/KEY: MISC_FEATURE
<223> OTHER INFORMATION: ABC_G1D04-VK

<400> SEQUENCE: 11

Asp Ile Val Met Ser Gln Ser Pro Ser Ser Leu Thr Val Ser Val Gly
1               5                   10                  15

Glu Asn Val Thr Met Ser Cys Lys Ser Ser Gln Asn Leu Leu Tyr Thr
            20                  25                  30

Ser Asn Gln Lys Asn Tyr Leu Ala Trp Tyr Gln Gln Lys Pro Gly His
        35                  40                  45

Ser Pro Lys Leu Leu Ile Ser Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Thr Ser Val Lys Ala Glu Asp Leu Ala Val Phe Tyr Cys Gln Gln
                85                  90                  95

Tyr Tyr His Tyr Pro Thr Phe Gly Gly Gly Thr Lys Leu Glu Ile Lys
            100                 105                 110

<210> SEQ ID NO 12
<211> LENGTH: 116
<212> TYPE: PRT
<213> ORGANISM: Mouse
<220> FEATURE:
<221> NAME/KEY: MISC_FEATURE
<223> OTHER INFORMATION: ABC_G1D05-VH

<400> SEQUENCE: 12

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Thr His
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Arg Lys Asp Asn Ser Lys Ser Gln Val Phe Phe
65                  70                  75                  80

Lys Met Asn Ser Leu Gln Thr Asn Asp Thr Ala Ile Tyr Tyr Cys Ala
                85                  90                  95

Arg Leu Arg Leu Pro Ala Met Asp Tyr Trp Gly Gln Gly Thr Ser Val
            100                 105                 110

Thr Val Ser Ser
        115

<210> SEQ ID NO 13
<211> LENGTH: 108
<212> TYPE: PRT
<213> ORGANISM: Mouse
<220> FEATURE:
<221> NAME/KEY: MISC_FEATURE
<223> OTHER INFORMATION: ABC_G1D05-VK

```
<400> SEQUENCE: 13

Gln Ile Val Leu Thr Gln Ser Pro Thr Ile Met Ser Ala Ser Leu Gly
1               5                   10                  15

Glu Arg Val Thr Met Thr Cys Thr Ala Ser Ser Val Ser Ser Ser Thr
            20                  25                  30

Tyr Leu His Trp Tyr Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Leu Ser Phe Gly Ala Gly Thr Lys Leu Glu Leu Lys
            100                 105

<210> SEQ ID NO 14
<211> LENGTH: 114
<212> TYPE: PRT
<213> ORGANISM: Mouse
<220> FEATURE:
<221> NAME/KEY: MISC_FEATURE
<223> OTHER INFORMATION: ABC_G1D06-VH

<400> SEQUENCE: 14

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Lys Phe Ser Asp Tyr
            20                  25                  30

Glu Ile His Trp Val Lys Gln Thr Pro Val Tyr Gly Leu Glu Trp Ile
        35                  40                  45

Gly Ala Leu Glu Pro Ala Thr Gly Gly Thr Ala Tyr Asn Pro Asn Phe
    50                  55                  60

Lys Gly Lys Ala Ile Leu Thr Ala Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ser Met His Leu Ala Val Tyr Trp Gly Gln Gly Thr Leu Val Thr Val
            100                 105                 110

Ser Ala

<210> SEQ ID NO 15
<211> LENGTH: 112
<212> TYPE: PRT
<213> ORGANISM: Mouse
<220> FEATURE:
<221> NAME/KEY: MISC_FEATURE
<223> OTHER INFORMATION: ABC_G1D06-VK

<400> SEQUENCE: 15

Asp Val Val Met Thr Gln Thr Pro Leu Thr Leu Ser Val Thr Phe Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60
```

```
Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Val Gln Gly
                 85                  90                  95

Thr His Ser Pro Arg Thr Phe Gly Gly Gly Thr Lys Leu Glu Ile Lys
            100                 105                 110

<210> SEQ ID NO 16
<211> LENGTH: 7
<212> TYPE: PRT
<213> ORGANISM: Mouse
<220> FEATURE:
<221> NAME/KEY: MISC_FEATURE
<223> OTHER INFORMATION: CDR-H1 sequence for ABC_G1D01

<400> SEQUENCE: 16

Gly Tyr Thr Phe Thr Asp Tyr
 1               5

<210> SEQ ID NO 17
<211> LENGTH: 6
<212> TYPE: PRT
<213> ORGANISM: Mouse
<220> FEATURE:
<221> NAME/KEY: MISC_FEATURE
<223> OTHER INFORMATION: CDR-H2 sequence for ABC_G1D01

<400> SEQUENCE: 17

Asn Pro Lys Asn Gly Val
 1               5

<210> SEQ ID NO 18
<211> LENGTH: 10
<212> TYPE: PRT
<213> ORGANISM: Mouse
<220> FEATURE:
<221> NAME/KEY: MISC_FEATURE
<223> OTHER INFORMATION: CDR-H3 sequence for ABC_G1D01

<400> SEQUENCE: 18

Asp Tyr Tyr Gly Thr Ala Trp Phe Ala Tyr
 1               5                  10

<210> SEQ ID NO 19
<211> LENGTH: 17
<212> TYPE: PRT
<213> ORGANISM: Mouse
<220> FEATURE:
<221> NAME/KEY: MISC_FEATURE
<223> OTHER INFORMATION: CDR-L1 sequence for ABC_G1D01

<400> SEQUENCE: 19

Arg Ser Ser Gln Ser Leu Leu Tyr Ser Ser Asn Gln Lys Asn Tyr Leu
 1               5                  10                  15

Ala

<210> SEQ ID NO 20
<211> LENGTH: 7
<212> TYPE: PRT
<213> ORGANISM: Mouse
<220> FEATURE:
<221> NAME/KEY: MISC_FEATURE
<223> OTHER INFORMATION: CDR-L2 sequence for ABC_G1D01
```

```
<400> SEQUENCE: 20

Trp Ala Ser Thr Arg Glu Ser
1               5

<210> SEQ ID NO 21
<211> LENGTH: 7
<212> TYPE: PRT
<213> ORGANISM: Mouse
<220> FEATURE:
<221> NAME/KEY: MISC_FEATURE
<223> OTHER INFORMATION: CDR-L3 for ABC_G1D01

<400> SEQUENCE: 21

Gln Gln Phe Ser Tyr Pro Thr
1               5

<210> SEQ ID NO 22
<211> LENGTH: 7
<212> TYPE: PRT
<213> ORGANISM: Mouse
<220> FEATURE:
<221> NAME/KEY: MISC_FEATURE
<223> OTHER INFORMATION: CDR-H1 sequence for ABC_G1D02

<400> SEQUENCE: 22

Gly Tyr Ala Phe Thr Asn Tyr
1               5

<210> SEQ ID NO 23
<211> LENGTH: 6
<212> TYPE: PRT
<213> ORGANISM: Mouse
<220> FEATURE:
<221> NAME/KEY: MISC_FEATURE
<223> OTHER INFORMATION: CDR-H2 sequence for ABC_G1D02

<400> SEQUENCE: 23

Asn Pro Gly Ser Gly Gly
1               5

<210> SEQ ID NO 24
<211> LENGTH: 6
<212> TYPE: PRT
<213> ORGANISM: Mouse
<220> FEATURE:
<221> NAME/KEY: MISC_FEATURE
<223> OTHER INFORMATION: CDR-H3 sequence for ABC_G1D02

<400> SEQUENCE: 24

Pro Gly His Phe Asp Tyr
1               5

<210> SEQ ID NO 25
<211> LENGTH: 12
<212> TYPE: PRT
<213> ORGANISM: Mouse
<220> FEATURE:
<221> NAME/KEY: MISC_FEATURE
<223> OTHER INFORMATION: CDR-L1 sequence for ABC_G1D02

<400> SEQUENCE: 25

Ser Ala Ser Ser Ser Ile Ser Ser Asn Tyr Leu His
1               5                   10

<210> SEQ ID NO 26
<211> LENGTH: 7
```

```
<212> TYPE: PRT
<213> ORGANISM: Mouse
<220> FEATURE:
<221> NAME/KEY: MISC_FEATURE
<223> OTHER INFORMATION: CDR-L2 sequence for ABC_G1D02

<400> SEQUENCE: 26

Lys Thr Ser Asn Leu Ala Ser
1               5

<210> SEQ ID NO 27
<211> LENGTH: 9
<212> TYPE: PRT
<213> ORGANISM: Mouse
<220> FEATURE:
<221> NAME/KEY: MISC_FEATURE
<223> OTHER INFORMATION: CDR-L3 sequence for ABC_G1D02

<400> SEQUENCE: 27

Gln Gln Gly Asn Ser Ile Pro Arg Thr
1               5

<210> SEQ ID NO 28
<211> LENGTH: 7
<212> TYPE: PRT
<213> ORGANISM: Mouse
<220> FEATURE:
<221> NAME/KEY: MISC_FEATURE
<223> OTHER INFORMATION: CDR-H1 sequence for ABC_G1D03

<400> SEQUENCE: 28

Gly Tyr Thr Phe Thr Asp His
1               5

<210> SEQ ID NO 29
<211> LENGTH: 6
<212> TYPE: PRT
<213> ORGANISM: Mouse
<220> FEATURE:
<221> NAME/KEY: MISC_FEATURE
<223> OTHER INFORMATION: CDR-H2 sequence for ABC_G1D03

<400> SEQUENCE: 29

Asn Pro Asn Thr Gly Val
1               5

<210> SEQ ID NO 30
<211> LENGTH: 10
<212> TYPE: PRT
<213> ORGANISM: Mouse
<220> FEATURE:
<221> NAME/KEY: MISC_FEATURE
<223> OTHER INFORMATION: CDR-H3 sequence for ABC_G1D03

<400> SEQUENCE: 30

Asp Tyr Tyr Gly Ser Ala Trp Phe Ala Tyr
1               5                   10

<210> SEQ ID NO 31
<211> LENGTH: 17
<212> TYPE: PRT
<213> ORGANISM: Mouse
<220> FEATURE:
<221> NAME/KEY: MISC_FEATURE
<223> OTHER INFORMATION: CDR-L1 sequence for ABC_G1D03
```

<400> SEQUENCE: 31

Lys Ser Ser Gln Thr Leu Leu Tyr Ser Ser Asp Gln Lys Asn Tyr Leu
1               5                   10                  15
Ala

<210> SEQ ID NO 32
<211> LENGTH: 7
<212> TYPE: PRT
<213> ORGANISM: Mouse
<220> FEATURE:
<221> NAME/KEY: MISC_FEATURE
<223> OTHER INFORMATION: CDR-L2 sequence for ABC_G1D03

<400> SEQUENCE: 32

Trp Ala Ser Thr Arg Glu Ser
1               5

<210> SEQ ID NO 33
<211> LENGTH: 8
<212> TYPE: PRT
<213> ORGANISM: Mouse
<220> FEATURE:
<221> NAME/KEY: MISC_FEATURE
<223> OTHER INFORMATION: CDR-L3 sequence for ABC_G1D03

<400> SEQUENCE: 33

Gln Gln Tyr Tyr Asn Tyr Pro Thr
1               5

<210> SEQ ID NO 34
<211> LENGTH: 7
<212> TYPE: PRT
<213> ORGANISM: Mouse
<220> FEATURE:
<221> NAME/KEY: MISC_FEATURE
<223> OTHER INFORMATION: CDR-H1 sequence for ABC_G1D04

<400> SEQUENCE: 34

Gly Tyr Thr Phe Thr Asp Tyr
1               5

<210> SEQ ID NO 35
<211> LENGTH: 6
<212> TYPE: PRT
<213> ORGANISM: Mouse
<220> FEATURE:
<221> NAME/KEY: MISC_FEATURE
<223> OTHER INFORMATION: CDR-H2 sequence for ABC_G1D04

<400> SEQUENCE: 35

Asp Pro Lys Asn Gly Gly
1               5

<210> SEQ ID NO 36
<211> LENGTH: 10
<212> TYPE: PRT
<213> ORGANISM: Mouse
<220> FEATURE:
<221> NAME/KEY: MISC_FEATURE
<223> OTHER INFORMATION: CDR-H3 sequence for ABC_G1D04

<400> SEQUENCE: 36

Asp Tyr Tyr Gly Ser Ala Trp Phe Ala Tyr
1               5                   10

```
<210> SEQ ID NO 37
<211> LENGTH: 17
<212> TYPE: PRT
<213> ORGANISM: Mouse
<220> FEATURE:
<221> NAME/KEY: MISC_FEATURE
<223> OTHER INFORMATION: CDR-L1 sequence for ABC_G1D04

<400> SEQUENCE: 37

Lys Ser Ser Gln Asn Leu Leu Tyr Thr Ser Asn Gln Lys Asn Tyr Leu
1               5                   10                  15

Ala

<210> SEQ ID NO 38
<211> LENGTH: 7
<212> TYPE: PRT
<213> ORGANISM: Mouse
<220> FEATURE:
<221> NAME/KEY: MISC_FEATURE
<223> OTHER INFORMATION: CDR-L2 sequence for ABC_G1D04

<400> SEQUENCE: 38

Trp Ala Ser Thr Arg Glu Ser
1               5

<210> SEQ ID NO 39
<211> LENGTH: 8
<212> TYPE: PRT
<213> ORGANISM: Mouse
<220> FEATURE:
<221> NAME/KEY: MISC_FEATURE
<223> OTHER INFORMATION: CDR-L3 sequence for ABC_G1D04

<400> SEQUENCE: 39

Gln Gln Tyr Tyr His Tyr Pro Thr
1               5

<210> SEQ ID NO 40
<211> LENGTH: 7
<212> TYPE: PRT
<213> ORGANISM: Mouse
<220> FEATURE:
<221> NAME/KEY: MISC_FEATURE
<223> OTHER INFORMATION: CDR-H1 sequence for ABC_G1D05

<400> SEQUENCE: 40

Gly Phe Ser Leu Thr Thr His
1               5

<210> SEQ ID NO 41
<211> LENGTH: 6
<212> TYPE: PRT
<213> ORGANISM: Mouse
<220> FEATURE:
<221> NAME/KEY: MISC_FEATURE
<223> OTHER INFORMATION: CDR-H2 sequence for ABC_G1D05

<400> SEQUENCE: 41

Ile Trp Ser Gly Gly Ser
1               5

<210> SEQ ID NO 42
<211> LENGTH: 8
<212> TYPE: PRT
<213> ORGANISM: Mouse
<220> FEATURE:
<221> NAME/KEY: MISC_FEATURE
<223> OTHER INFORMATION: CDR-H3 sequence for ABC_G1D05
```

```
<400> SEQUENCE: 42

Leu Arg Leu Pro Ala Met Asp Tyr
1               5

<210> SEQ ID NO 43
<211> LENGTH: 12
<212> TYPE: PRT
<213> ORGANISM: Mouse
<220> FEATURE:
<221> NAME/KEY: MISC_FEATURE
<223> OTHER INFORMATION: CDR-L1 sequence for ABC_G1D05

<400> SEQUENCE: 43

Thr Ala Ser Ser Ser Val Ser Ser Thr Tyr Leu His
1               5                   10

<210> SEQ ID NO 44
<211> LENGTH: 7
<212> TYPE: PRT
<213> ORGANISM: Mouse
<220> FEATURE:
<221> NAME/KEY: MISC_FEATURE
<223> OTHER INFORMATION: CDR-L2 sequence for ABC_G1D05

<400> SEQUENCE: 44

Ser Thr Ser Asn Leu Ala Ser
1               5

<210> SEQ ID NO 45
<211> LENGTH: 9
<212> TYPE: PRT
<213> ORGANISM: Mouse
<220> FEATURE:
<221> NAME/KEY: MISC_FEATURE
<223> OTHER INFORMATION: CDR-L3 sequence for ABC_G1D05

<400> SEQUENCE: 45

His Gln Tyr His Arg Ser Pro Leu Ser
1               5

<210> SEQ ID NO 46
<211> LENGTH: 7
<212> TYPE: PRT
<213> ORGANISM: Mouse
<220> FEATURE:
<221> NAME/KEY: MISC_FEATURE
<223> OTHER INFORMATION: CDR-H1 sequence for ABC_G1D06

<400> SEQUENCE: 46

Gly Tyr Lys Phe Ser Asp Tyr
1               5

<210> SEQ ID NO 47
<211> LENGTH: 7
<212> TYPE: PRT
<213> ORGANISM: Mouse
<220> FEATURE:
<221> NAME/KEY: MISC_FEATURE
<223> OTHER INFORMATION: CDR-H2 sequence for ABC_G1D06

<400> SEQUENCE: 47

Leu Glu Pro Ala Thr Gly Gly
1               5

<210> SEQ ID NO 48
<211> LENGTH: 5
```

```
<212> TYPE: PRT
<213> ORGANISM: Mouse
<220> FEATURE:
<221> NAME/KEY: MISC_FEATURE
<223> OTHER INFORMATION: CDR-H3 sequence for ABC_G1D06

<400> SEQUENCE: 48

His Leu Ala Val Tyr
1               5

<210> SEQ ID NO 49
<211> LENGTH: 16
<212> TYPE: PRT
<213> ORGANISM: Mouse
<220> FEATURE:
<221> NAME/KEY: MISC_FEATURE
<223> OTHER INFORMATION: CDR-L1 sequence for ABC_G1D06

<400> SEQUENCE: 49

Lys Ser Ser Gln Ser Leu Leu Tyr Ser Asn Gly Lys Thr Tyr Leu Asn
1               5                   10                  15

<210> SEQ ID NO 50
<211> LENGTH: 8
<212> TYPE: PRT
<213> ORGANISM: Mouse
<220> FEATURE:
<221> NAME/KEY: MISC_FEATURE
<223> OTHER INFORMATION: CDR-L2 sequence for ABC_G1D06

<400> SEQUENCE: 50

Leu Val Ser Lys Leu Asp Ser Gly
1               5

<210> SEQ ID NO 51
<211> LENGTH: 9
<212> TYPE: PRT
<213> ORGANISM: Mouse
<220> FEATURE:
<221> NAME/KEY: MISC_FEATURE
<223> OTHER INFORMATION: CDR-L3 sequence for ABC_G1D06

<400> SEQUENCE: 51

Val Gln Gly Thr His Ser Pro Arg Thr
1               5

<210> SEQ ID NO 52
<211> LENGTH: 115
<212> TYPE: PRT
<213> ORGANISM: artificial
<220> FEATURE:
<223> OTHER INFORMATION: humanized synthetic sequence for ABC_HG1D02-VH

<400> SEQUENCE: 52

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Asn Tyr
                20                  25                  30

Phe Ile Glu Trp Val Arg Gln Arg Pro Gly Gln Gly Leu Glu Trp Met
            35                  40                  45

Gly Val Ile Asn Pro Gly Ser Gly Gly Thr Asn Tyr Asn Glu Lys Phe
        50                  55                  60

Lys Gly Arg Val Thr Ile Thr Ala Asp Lys Ser Ser Thr Ala Tyr
65                  70                  75                  80
```

Met Glu Leu Ser Ser Leu Arg Ser Glu Asp Thr Ala Val Tyr Tyr Cys
            85                  90                  95

Ala Arg Pro Gly His Phe Asp Tyr Trp Gly Gln Gly Thr Thr Val Thr
            100                 105                 110

Val Ser Ser
        115

<210> SEQ ID NO 53
<211> LENGTH: 111
<212> TYPE: PRT
<213> ORGANISM: artificial
<220> FEATURE:
<223> OTHER INFORMATION: humanized synthetic sequence for ABC_HG1D02-VK

<400> SEQUENCE: 53

Glu Ile Val Leu Thr Gln Ser Pro Thr Thr Leu Ser Leu Ser Pro Gly
1               5                   10                  15

Glu Arg Ala Thr Leu Ser Cys Ser Ala Ser Ser Ser Ile Ser Ser Asn
            20                  25                  30

Tyr Leu His Trp Tyr Gln Gln Lys Pro Gly Phe Ala Pro Arg Leu Leu
        35                  40                  45

Ile Tyr Lys Thr Ser Asn Leu Ala Ser Gly Ile Pro Pro Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Asn Ser Ile Pro
                85                  90                  95

Arg Thr Phe Gly Gln Gly Thr Lys Val Glu Ile Lys Arg Thr Val
            100                 105                 110

<210> SEQ ID NO 54
<211> LENGTH: 119
<212> TYPE: PRT
<213> ORGANISM: artificial
<220> FEATURE:
<223> OTHER INFORMATION: humanized synthetic sequence for ABC_HG1D03-VH

<400> SEQUENCE: 54

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Asn Met His Trp Val Lys Gln Ala Thr Gly Gln Gly Leu Glu Trp Phe
        35                  40                  45

Gly Phe Ile Asn Pro Asn Thr Gly Val Thr Arg Tyr Asn Gln Lys Phe
    50                  55                  60

Gln Gly Arg Val Thr Leu Thr Ile Asn Lys Ala Ile Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Tyr Tyr Gly Ser Ala Trp Phe Ala Tyr Trp Gly Gln Gly
            100                 105                 110

Thr Leu Val Thr Val Ser Ser
        115

<210> SEQ ID NO 55
<211> LENGTH: 109
<212> TYPE: PRT

<213> ORGANISM: artificial
<220> FEATURE:
<223> OTHER INFORMATION: humanized synthetic sequence for ABC_HG1D03-VK
<220> FEATURE:
<221> NAME/KEY: MISC_FEATURE
<223> OTHER INFORMATION: humanized synthetic sequence for ABC_HG1D03-VK

<400> SEQUENCE: 55

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Leu Leu Tyr Ser
            20                  25                  30

Ser Asp Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asn Tyr Pro Thr Phe Gly Gly Gly Thr Lys Val
            100                 105

<210> SEQ ID NO 56
<211> LENGTH: 7
<212> TYPE: PRT
<213> ORGANISM: artificial
<220> FEATURE:
<223> OTHER INFORMATION: epitope of KLRG1

<400> SEQUENCE: 56

Pro Leu Asn Phe Ser Arg Ile
1               5

<210> SEQ ID NO 57
<211> LENGTH: 13
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 57

Gly Ser Gly Ser Gly Ser Gly Ser Cys Pro Asp Arg Trp
1               5                   10

<210> SEQ ID NO 58
<211> LENGTH: 13
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 58

Gly Ser Gly Ser Cys Pro Asp Arg Trp Met Lys Tyr Gly
1               5                   10

<210> SEQ ID NO 59
<211> LENGTH: 12
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 59

Cys Pro Asp Arg Trp Met Lys Tyr Gly Asn His Cys
1               5                   10

<210> SEQ ID NO 60
<211> LENGTH: 13
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 60

Trp Met Lys Tyr Gly Asn His Cys Tyr Tyr Phe Ser Val
1               5                   10

<210> SEQ ID NO 61
<211> LENGTH: 13
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 61

Gly Asn His Cys Tyr Tyr Phe Ser Val Glu Glu Lys Asp
1               5                   10

<210> SEQ ID NO 62
<211> LENGTH: 15
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 62

Tyr Tyr Phe Ser Val Glu Glu Lys Asp Trp Asn Ser Ser Leu Glu
1               5                   10                  15

<210> SEQ ID NO 63
<211> LENGTH: 15
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 63

Val Glu Glu Lys Asp Trp Asn Ser Ser Leu Glu Phe Cys Leu Ala
1               5                   10                  15

<210> SEQ ID NO 64
<211> LENGTH: 15
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 64

Asp Trp Asn Ser Ser Leu Glu Phe Cys Leu Ala Arg Asp Ser His
1               5                   10                  15

<210> SEQ ID NO 65
<211> LENGTH: 15

```
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 65

Ser Leu Glu Phe Cys Leu Ala Arg Asp Ser His Leu Leu Val Ile
1               5                   10                  15

<210> SEQ ID NO 66
<211> LENGTH: 15
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 66

Cys Leu Ala Arg Asp Ser His Leu Leu Val Ile Thr Asp Asn Gln
1               5                   10                  15

<210> SEQ ID NO 67
<211> LENGTH: 15
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 67

Asp Ser His Leu Leu Val Ile Thr Asp Asn Gln Glu Met Ser Leu
1               5                   10                  15

<210> SEQ ID NO 68
<211> LENGTH: 15
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 68

Leu Val Ile Thr Asp Asn Gln Glu Met Ser Leu Leu Gln Val Phe
1               5                   10                  15

<210> SEQ ID NO 69
<211> LENGTH: 15
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 69

Asp Asn Gln Glu Met Ser Leu Leu Gln Val Phe Leu Ser Glu Ala
1               5                   10                  15

<210> SEQ ID NO 70
<211> LENGTH: 15
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1
```

<400> SEQUENCE: 70

Met Ser Leu Leu Gln Val Phe Leu Ser Glu Ala Phe Cys Trp Ile
1               5                   10                  15

<210> SEQ ID NO 71
<211> LENGTH: 15
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 71

Gln Val Phe Leu Ser Glu Ala Phe Cys Trp Ile Gly Leu Arg Asn
1               5                   10                  15

<210> SEQ ID NO 72
<211> LENGTH: 14
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 72

Ser Glu Ala Phe Cys Trp Ile Phe Leu Arg Asn Asn Ser Gly
1               5                   10

<210> SEQ ID NO 73
<211> LENGTH: 12
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 73

Cys Trp Ile Gly Leu Arg Asn Asn Ser Gly Trp Arg
1               5                   10

<210> SEQ ID NO 74
<211> LENGTH: 12
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 74

Leu Arg Asn Asn Ser Gly Trp Arg Trp Glu Asp Gly
1               5                   10

<210> SEQ ID NO 75
<211> LENGTH: 13
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 75

Ser Gly Trp Arg Trp Glu Asp Gly Ser Pro Leu Asn Phe
1               5                   10

<210> SEQ ID NO 76
<211> LENGTH: 15

```
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 76

Trp Glu Asp Gly Ser Pro Leu Asn Phe Ser Arg Ile Ser Ser Asn
1               5                   10                  15

<210> SEQ ID NO 77
<211> LENGTH: 15
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 77

Ser Pro Leu Asn Phe Ser Arg Ile Ser Ser Asn Ser Phe Val Gln
1               5                   10                  15

<210> SEQ ID NO 78
<211> LENGTH: 15
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 78

Phe Ser Arg Ile Ser Ser Asn Ser Phe Val Gln Thr Cys Gly Ala
1               5                   10                  15

<210> SEQ ID NO 79
<211> LENGTH: 15
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 79

Ser Ser Asn Ser Phe Val Gln Thr Cys Gly Ala Ile Asn Lys Asn
1               5                   10                  15

<210> SEQ ID NO 80
<211> LENGTH: 15
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 80

Phe Val Gln Thr Cys Gly Ala Ile Asn Lys Asn Gly Leu Gln Ala
1               5                   10                  15

<210> SEQ ID NO 81
<211> LENGTH: 15
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1
```

<400> SEQUENCE: 81

Cys Gly Ala Ile Asn Lys Asn Gly Leu Gln Ala Ser Ser Cys Glu
1               5                   10                  15

<210> SEQ ID NO 82
<211> LENGTH: 15
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 82

Asn Lys Asn Gly Leu Gln Ala Ser Ser Cys Glu Val Pro Leu His
1               5                   10                  15

<210> SEQ ID NO 83
<211> LENGTH: 15
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 83

Leu Gln Ala Ser Ser Cys Glu Val Pro Leu His Trp Val Cys Lys
1               5                   10                  15

<210> SEQ ID NO 84
<211> LENGTH: 15
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 84

Ser Cys Glu Val Pro Leu His Trp Val Cys Lys Lys Val Arg Leu
1               5                   10                  15

<210> SEQ ID NO 85
<211> LENGTH: 15
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 85

Pro Leu His Trp Val Cys Lys Lys Val Arg Leu Gly Ser Gly Ser
1               5                   10                  15

<210> SEQ ID NO 86
<211> LENGTH: 15
<212> TYPE: PRT
<213> ORGANISM: Homo sapiens
<220> FEATURE:
<221> NAME/KEY: MISC_FEATURE
<223> OTHER INFORMATION: Peptide fragment of human KLGR1

<400> SEQUENCE: 86

Val Cys Lys Lys Val Arg Leu Gly Ser Gly Ser Gly Ser Gly Leu
1               5                   10                  15

METHODS OF TREATING DISORDERS ASSOCIATED WITH EXCESS OR UNWANTED KILLER CELL LECTIN-LIKE RECEPTOR SUBFAMILY G MEMBER 1 (KLRG1) EXPRESSING T CELLS WITH KLRG1 DEPLETING ANTIBODIES

PRIORITY DATA

This application is a divisional of U.S. patent application Ser. No. 16/844,747, filed Apr. 9, 2020, which claims the benefit of U.S. Provisional Patent Application No. 62/831,713, filed Apr. 9, 2019, the contents of each of which are incorporated herein in their entirety.

SEQUENCE LISTING

The instant application contains a Sequence Listing which has been submitted electronically in ASCII format and is hereby incorporated by reference in its entirety. Said ASCII copy, created on Apr. 9, 2019 is named 20211020_1303482_1.txt and is 42,345 bytes in size.

FIELD

The present disclosure relates to antibodies, or antigen-binding fragments thereof, that specifically bind to killer cell lectin-like receptor G1 (KLRG1). Such antibodies, or antigen-binding fragments of such antibodies, can be useful for various therapeutic or diagnostic purposes, including treatment of autoimmune diseases, cancers, and to increase the effectiveness of vaccines.

BACKGROUND

Autoimmunity and Transplant

Cellular injury occurs in many diseases as a consequence of cytotoxic T cell attack. For example, pathogenic cytotoxic T cells are a key element in the destruction of muscle that occurs in the disease inclusion body myositis. Similar mechanisms of injury to tissues by cytotoxic T cells are implicated in other autoimmune diseases such as multiple sclerosis, rheumatoid arthritis, psoriasis, inflammatory bowel disease, autoimmune thyroid disease, type 1 diabetes, alopecia areata, Bechet's disease, ankylosing spondylitis, and primary biliary cirrhosis.

Similar mechanisms of injury are also present in solid organ transplantation, such as in graft versus host disease and organ rejection developing in the setting of transplantation associated with attack on tissues by CD8+ T cells, where there are increased proportions of highly potent increased differentiated T cells, such as T effector memory (TEM) and T effector memory RA (TEMRA).

As described in PCT Application No. PCT/US2017/051776, killer cell lectin-like receptor G1 (KLRG1), a cell surface marker known to be present on senescent cytotoxic T cells, has been demonstrated by the inventors of the present disclosure to also be present on cytotoxic T cells with high-killing potential. For example, in the case of inclusion body myositis, cell surface KLRG1 marks T cells that are directly killing healthy muscle cells. Unlike the teachings of prior studies regarding the senescent and inactive nature of KLRG1-expressing T cells in the blood of mice and humans, KLRG1-expressing T cells can be active and pathogenic, rendering them an advantageous target for cell depletion therapy.

Such cell depletion therapy comprises, in one example, administering to a subject in need thereof an effective amount of KLRG1 depleting agent (e.g., a KLRG1-expressing-cell depleting agent). The KLRG1 depleting agent can target the extracellular domain of KLRG1, comprising antibody dependent cellular cytotoxicity (ADCC) effector function, and can eliminate or reduce the number of cytotoxic T cells and/or NK cells injuring healthy cells.

Administering a KLRG1 depleting agent also can be effective in treating leukemias and lymphomas, which also involve the abnormal expansion of CD8+ T cells. In particular, T cell large granular lymphocytic leukemia (T-LGLL) is a leukemia characterized by expansion of late-stage differentiated CD8+ T cells, and NK cell lymphoproliferative disorder is a leukemia characterized by NK cell expansion. Extranasal NK/T cell lymphoma is a related disorder.

KLRG1 is type II transmembrane protein and is a co-inhibitory receptor modulating the activity of T and NK cells. Its extracellular portion contains a C-type lectin domain whose known ligands are cadherins and its intracellular portion contains an immunoreceptor tyrosine-based inhibitory motif (ITIM) domain responsible for co-inhibition of T cell receptor (TCR) mediated signaling. In various embodiments, the ligand can be E-cadherin, N-cadherin, R-cadherin, or a combination thereof.

In association with its cadherin ligands, KLRG1 can function as a co-inhibitory receptor in a similar manner as a number of other T cell co-inhibitory receptors such as CTLA-4, PD-1, LAG-3, and TIM-3. Accordingly, KLRG1 is a favorable target for immunotherapy such as cancer immunotherapy. For example, administering to a subject in need thereof an effective amount of KLRG1/ligand binding agent can disrupt KLRG1 signaling and activate CD8+ cytotoxic T and/or NK cells. Thus, a KLRG1/ligand binding agent has numerous therapeutic uses, including for treating cancer, regardless of whether the cancer itself expresses KLRG1.

However, it has been observed that in patients with autoimmune diseases, cancer treatment with checkpoint inhibitor immunotherapy increases the risk of flares. These flares, however, are associated with improved cancer outcomes. As indicated by Ted Bosworth in Rheumatology News in an article entitled "Checkpoint inhibitors in autoimmune disease: More flares, better cancer outcomes," dated Jun. 25, 2018, "[w]ith the initiation of checkpoint inhibitors, which were offered primarily for the treatment of melanoma (59%) and non-small cell lung cancer (36%), 42% of patients with PAD developed a disease flare. Of these, 30% were considered severe . . . . However, those with a flare or another immune-related adverse event had significantly better progression-free survival (P=0.016) and overall survival (P=0.004) when compared with those who did not flare or have an immune-related adverse event." Without being bound by theory, this study indicates that release of checkpoint inhibition activates CD8+ cytotoxic T and/or NK cells with all kinds of specificities in addition to tumor specificities, which may result in instigating or reactivating autoimmune disease in treated patients.

Therefore, there is a need in the art for adjunct therapy for cancer patients undergoing checkpoint therapy (regardless of whether the cancer expresses KLRG1), where the adjunct therapy comprises the use of a KLRG1 binding agent to deplete pathogenic T cells and/or NK cells attacking self-tissues, advantageously with no loss of T cells and/or NK cells directed to the cancer cells[1].

[1] Applicant's working Example 6

Therefore, there is a need in the art for treating patients having a type of cancer wherein the cancer cells express KLRG1, where the treatment comprises the use of a KLRG1 binding agent to deplete cancer cells which express KLRG1, where the KLRG1 binding agent does not release the checkpoint inhibition and subsequent activation of pathogenic CD8+ cytotoxic T and/or NK cells directed to self-tissues.

Therefore, there is a need in the autoimmune art which uses a KLRG1 binding agent to deplete pathogenic T cells and/or NK cells attacking self-tissues, where the KLRG1 binding agent does not release the checkpoint inhibition and subsequent activation of pathogenic CD8+ cytotoxic T and/or NK cells directed to self-tissues.

Therefore, there is a need in the transplantation art which uses a KLRG1 binding agent to deplete pathogenic T cells and/or NK cells attacking transplanted tissues, where the KLRG1 binding agent does not release the checkpoint inhibition and subsequent activation of pathogenic CD8+ cytotoxic T and/or NK cells directed to either transplanted or self-tissues or cells.

SUMMARY

The receptor killer cell lectin-like receptor G1 (KLRG1) is expressed on T and NK cells which binds to ligands on epithelial and mesenchymal cells. The ligands for KLRG1 expressed on T and NK cells have been described to be E-cadherin, N-cadherin, and R-cadherin. The present disclosure provides for the discovery and characterization of binding agents, such as antibodies, that bind the extracellular domain (ECD) of KLRG1, but do not interfere with its interaction with ligands E-cadherin, N-cadherin, and R-cadherin. The antibodies described herein have been derived by mouse hybridoma technology and can be humanized by grafting their complementary determining regions (CDRs) into a human framework. The antibodies provided for herein can be used as effective therapeutic agents.

Disclosed herein, among a number of different embodiments, is one exemplary embodiment of a method of depleting KLRG1 expressing T cells and/or NK cells in a subject in need of depletion treatment without interfering with binding of E-cadherin, N-cadherin, or R-cadherin to the extracellular domain of KLRG1. The method comprises delivering to a subject an effective amount of antibody, or a fragment of the antibody. The antibody, or fragment thereof, specifically binds to the extracellular domain of KLRG1 but does not compete with binding of E-cadherin, N-cadherin, or R-cadherin to the extracellular domain of KLRG1, thereby depleting KLRG1 expressing T cells in the subject.

In some embodiments, the antibody, or a fragment thereof, can comprise a heavy chain variable region comprising three complementarity determining regions of an amino acid sequence of: SEQ ID NO:4, SEQ ID NO:6, SEQ ID NO:8, SEQ ID NO: 10, SEQ ID NO: 12, or SEQ ID NO:14. Alternatively, or additionally, the antibody, or a fragment thereof, can comprise a light chain variable region comprising three complementarity determining regions of an amino acid sequence of: SEQ ID NO:5, SEQ ID NO:7, SEQ ID NO:9, SEQ ID NO: 11, SEQ ID NO: 13, or SEQ ID NO:15.

The KLRG1 can comprise human KLRG1 or Cyano KLRG1.

In some embodiments, the antibody, or a fragment thereof, can comprise a monoclonal antibody, or a fragment thereof. In some such instances, the monoclonal antibody, or a fragment thereof, can specifically bind the epitope PLNFSRI (SEQ ID NO:56), or a fragment thereof, comprising at least five (5) contiguous amino acids. The monoclonal antibody, or a fragment thereof, can comprise a heavy chain variable region comprising an amino acid sequence of SEQ ID NO: 4, or a sequence approximately at least 90% identical to that sequence. Alternatively, the monoclonal antibody, or a fragment thereof, can comprise a light chain variable region comprising an amino acid sequence of SEQ ID NO:5, or a sequence approximately at least 90% identical to that sequence. Further alternatively, the monoclonal antibody, or a fragment thereof, can comprise a heavy chain variable region comprising an amino acid sequence of SEQ ID NO: 6, or a sequence approximately at least 90% identical to that sequence. Still further alternatively, the monoclonal antibody, or a fragment thereof, can comprise a light chain variable region comprising an amino acid sequence of SEQ ID NO:7, or a sequence approximately at least 90% identical to that sequence. Further alternatively, the monoclonal antibody, or a fragment thereof, can comprise a heavy chain variable region comprising an amino acid sequence of SEQ ID NO:8, or a sequence approximately at least 90% identical to that sequence. Still further alternatively, the monoclonal antibody, or a fragment thereof, can comprise a light chain variable region comprising an amino acid sequence of SEQ ID NO:9, or a sequence approximately at least 90% identical to that sequence. Further alternatively, the monoclonal antibody, or a fragment thereof, can comprise a heavy chain variable region comprising an amino acid sequence of SEQ ID NO:10, or a sequence approximately at least 90% identical to that sequence. Still further alternatively, the monoclonal antibody, or a fragment thereof, can comprise a light chain variable region comprising an amino acid sequence of SEQ ID NO:11, or a sequence approximately at least 90% identical to that sequence. Further alternatively, the monoclonal antibody, or a fragment thereof, can comprise a heavy chain variable region comprising an amino acid sequence of SEQ ID NO: 12, or a sequence approximately at least 90% identical to that sequence. Still further alternatively, the monoclonal antibody, or a fragment thereof, can comprise a light chain variable region comprising an amino acid sequence of SEQ ID NO: 13, or a sequence approximately at least 90% identical to that sequence. Further alternatively, the monoclonal antibody, or a fragment thereof, can comprise a heavy chain variable region comprising an amino acid sequence of SEQ ID NO: 14, or a sequence approximately at least 90% identical to that sequence. Still further alternatively, the monoclonal antibody, or a fragment thereof, can comprise a light chain variable region comprising an amino acid sequence of SEQ ID NO: 15, or a sequence approximately at least 90% identical to that sequence.

In some embodiments in which the antibody, or a fragment thereof, comprises a monoclonal antibody, or a fragment thereof, the monoclonal antibody, or a fragment thereof, can comprise a chimeric antibody, or a fragment thereof. In some embodiments in which the antibody, or a fragment thereof, comprises a monoclonal antibody, or a fragment thereof, the monoclonal antibody, or a fragment thereof, can comprise a humanized antibody or a fragment thereof.

Another exemplary embodiment of the present disclosure provides for a method of treating a disorder associated with excess KLRG1 expressing T cells in a subject in need of treatment. The method comprises delivering to a subject a therapeutically effective amount of an antibody, or a fragment of the antibody, that specifically binds to an extracellular domain of KLRG1 without interfering with binding by E-cadherin, N-cadherin, or R-cadherin to the extracellular domain of KLRG1. The delivery to the subject depletes KLRG1 expressing T cells, and does not release checkpoint inhibition and subsequent activation of pathogenic CD8+ cytotoxic T and/or NK cells directed to self-tissues, thereby treating the disorder. The antibody, or a fragment of the antibody, comprises a heavy chain variable region comprising three complementarity determining regions of an amino acid sequence of: SEQ ID NO:4, SEQ ID NO: 6, SEQ ID NO:8, SEQ ID NO: 10, SEQ ID NO: 12, or SEQ ID NO:14. Alternatively, or additionally, the antibody, or a fragment of the antibody, comprises a light chain variable region comprising three complementarity determining regions of an amino acid sequence of: SEQ ID NO: 5, SEQ ID NO:7, SEQ ID NO:9, SEQ ID NO: 11, SEQ ID NO: 13, or SEQ ID NO: 15.

In some embodiments, the disorder can comprise a transplant related disorder, and the delivery to the subject can deplete KLRG1 expressing pathogenic T cells and/or NK cells attacking transplanted tissues in the subject. Alternatively, the disorder can comprise an autoimmune disease, and the delivery to the subject can deplete KLRG1 expressing pathogenic T cells and/or NK cells attacking self-tissues in the subject.

Still another exemplary embodiment of the present disclosure provides for a method of treating cancer in a subject, where the cancer comprises cancer cells that express KLRG1. The method comprises delivering to a subject a therapeutically effective amount of an antibody, or a fragment of the antibody, that specifically binds to an extracellular domain of KLRG1 without interfering with binding by E-cadherin, N-cadherin, or R-cadherin to the extracellular domain of KLRG1. The delivery to the subject depletes the cancer cells expressing KLRG1, and the delivery does not release checkpoint inhibition and subsequent activation of pathogenic CD8+ cytotoxic T and/or NK cells directed to self-tissues. The antibody, or a fragment of the antibody, comprises a heavy chain variable region comprising three complementarity determining regions of an amino acid sequence of: SEQ ID NO:4, SEQ ID NO:6, SEQ ID NO:8, SEQ ID NO: 10, SEQ ID NO: 12, or SEQ ID NO: 14. Alternatively, or additionally, the antibody, or a fragment of the antibody, comprises a light chain variable region comprising three complementarity determining regions of an amino acid sequence of: SEQ ID NO:5, SEQ ID NO:7, SEQ ID NO:9, SEQ ID NO:11, SEQ ID NO:13, or SEQ ID NO: 15.

One, non-limiting exemplary embodiment of a therapy provided for in the present disclosure is an adjunct therapy for treatment of cancer in a subject in which the subject is undergoing checkpoint therapy. The method is performed regardless of whether the cancer expresses KLRG1. The adjunct therapy comprises delivering to a subject a therapeutically effective amount of an antibody, or a fragment of the antibody, that specifically binds to an extracellular domain of KLRG1 without interfering with binding by E-cadherin, N-cadherin, or R-cadherin to the extracellular domain of KLRG1. The delivery depletes KLRG1 expressing pathogenic T cells and/or NK cells attacking self-tissues in the subject. The antibody, or a fragment of the antibody, comprises a heavy chain variable region comprising three complementarity determining regions of an amino acid sequence of: SEQ ID NO:4, SEQ ID NO: 6, SEQ ID NO:8, SEQ ID NO: 10, SEQ ID NO: 12, or SEQ ID NO: 14. Alternatively, or additionally, the antibody, or a fragment of the antibody, comprises a light chain variable region comprising three complementarity determining regions of an amino acid sequence of: SEQ ID NO: 5, SEQ ID NO:7, SEQ ID NO:9, SEQ ID NO: 11, SEQ ID NO: 13, or SEQ ID NO: 15.

Also disclosed herein is one exemplary embodiment of a method of depleting KLRG1 expressing cells in a mixed population of cells in which the KLRG1 expressing cells comprise one or more cells selected from the group of T cells and/or NK cells and/or cancer cells. The method comprises delivering to a mixed population of cells an effective amount of an antibody, or a fragment of the antibody, that specifically binds to KLRG1 and depletes KLRG1 expressing T cells and/or NK cells and/or cancer cells, thereby depleting KLRG1 expressing T cells and/or NK cells and/or cancer cells in the mixed population of cells. The antibody, or a fragment of the antibody, comprises a heavy chain variable region comprising three complementarity determining regions of an amino acid sequence of: SEQ ID NO:4, SEQ ID NO:6, SEQ ID NO:8, SEQ ID NO:10, SEQ ID NO:12, or SEQ ID NO:14. Alternatively, or additionally, the antibody, or a fragment of the antibody, comprises a light chain variable region comprising three complementarity determining regions of an amino acid sequence of: SEQ ID NO:5, SEQ ID NO: 7, SEQ ID NO:9, SEQ ID NO: 11, SEQ ID NO: 13, or SEQ ID NO: 15.

The present disclosure also provides exemplary embodiments of antibodies, or a fragment of such antibodies. One non-limiting exemplary embodiment of an antibody, or a fragment of the antibody, is one that specifically binds to an extracellular domain of KLGR1 but does not compete with E-cadherin, N-cadherin, or R-cadherin binding to KLRG1. The antibody, or fragment of the antibody, depletes cells expressing KLGR1 when administered to a subject.

In some embodiments, the antibody, or a fragment of the antibody, can comprise a heavy chain variable region comprising three complementarity determining regions of an amino acid sequence of: SEQ ID NO:4, SEQ ID NO:6, SEQ ID NO:8, SEQ ID NO: 10, SEQ ID NO: 12, or SEQ ID NO:14. Alternatively, or additionally, the antibody, or a fragment of the antibody, can comprise a light chain variable region comprising three complementarity determining regions of an amino acid sequence of: SEQ ID NO:5, SEQ ID NO:7, SEQ ID NO:9, SEQ ID NO: 11, SEQ ID NO: 13, or SEQ ID NO: 15.

The antibody, or a fragment of the antibody, can be such that the KLRG1 comprises human KLRG1 or Cyano KLRG1.

The antibody, or a fragment of the antibody, can comprise a monoclonal antibody, or a fragment or derivative thereof. In some such instances, the monoclonal antibody, or a fragment thereof, can specifically bind the epitope PLNFSRI (SEQ ID NO:56), or a fragment thereof, comprising at least five (5) contiguous amino acids. The monoclonal antibody, or a fragment thereof, can comprise a heavy chain variable region comprising the amino acid sequence of SEQ ID NO: 4, or a sequence approximately at least 90% identical to that sequence. Alternatively, the monoclonal antibody, or a fragment thereof, can comprise a light chain variable region comprising the amino acid sequence of SEQ ID NO:5, or a sequence approximately at least 90% identical to that sequence. Further alternatively, the monoclonal antibody, or a fragment thereof, can comprise a heavy chain variable region comprising the amino acid sequence of SEQ ID NO: 6, or a sequence approximately at least 90% identical to that sequence. Still further alternatively, the monoclonal antibody, or a fragment thereof, can comprise a light chain variable region comprising the amino acid sequence of SEQ ID NO:7, or a sequence approximately at least 90% identical to that sequence. Further alternatively, the monoclonal antibody, or a fragment thereof, can comprise a heavy chain variable region comprising the amino acid sequence of SEQ ID NO:8, or a sequence approximately at least 90% identical to that sequence. Still further alternatively, the monoclonal antibody, or a fragment thereof, can comprise a light chain variable region comprising the amino acid sequence of SEQ ID NO:9, or a sequence approximately at least 90% identical to that sequence. Further alternatively, the monoclonal antibody, or a fragment thereof, can comprise a heavy chain variable region comprising the amino acid sequence of SEQ ID NO:10, or a sequence approximately at least 90% identical to that sequence. Still further alternatively, the monoclonal antibody, or a fragment thereof, can comprise a light chain variable region comprising the amino acid sequence of SEQ ID NO:11, or a sequence approximately at least 90% identical to that sequence. Further alternatively, the monoclonal antibody, or a fragment thereof, can comprise a heavy chain variable region comprising the amino acid sequence of SEQ ID NO: 12, or a sequence approximately at least 90% identical to that sequence. Still further alternatively, the monoclonal antibody, or a fragment thereof, can comprise a light chain variable region comprising the amino acid sequence of SEQ ID NO: 13, or a sequence approximately at least 90% identical to that sequence. Further alternatively, the monoclonal antibody, or a fragment thereof, can comprise a heavy chain variable region comprising the amino acid sequence of SEQ ID NO: 14, or a sequence approximately at least 90% identical to that sequence. Still further alternatively, the monoclonal antibody, or a fragment thereof, can comprise a light chain variable region comprising the amino acid sequence of SEQ ID NO: 15, or a sequence approximately at least 90% identical to that sequence.

In some embodiments in which the antibody, or a fragment thereof, comprises a monoclonal antibody, or a fragment thereof, the monoclonal antibody, or a fragment thereof, can comprise a chimeric antibody, or a fragment thereof. In some embodiments in which the antibody, or a fragment thereof, comprises a monoclonal antibody, or a fragment thereof, the monoclonal antibody, or a fragment thereof, can comprise a humanized antibody or a fragment thereof.

A person skilled in the art will appreciate that many of the limitations provided for above can be applicable to each of the exemplary embodiments, as well as other embodiments provided for in the present disclosure. By way of non-limiting example, in any of the embodiments provided for in the present disclosure, the monoclonal antibody, or a fragment thereof, can comprise a humanized antibody, or a fragment thereof, or a chimeric antibody, or a fragment thereof.

The present disclosure also provides for exemplary pharmaceutical compositions. In one non-limiting exemplary embodiment, a pharmaceutical composition comprises one or more of an antibody, or fragment of the antibody, a monoclonal antibody, or a fragment of the antibody, or derivative of either such antibody or fragment, as disclosed herein (e.g., the antibodies described above or otherwise provided for in the present disclosure), and a pharmaceutically acceptable carrier.

The present disclosure also provides for exemplary kits. In one non-limiting exemplary embodiment, a kit comprises one or more of an antibody, or fragment of the antibody, a monoclonal antibody, or a fragment of the antibody, or derivative of either such antibody or fragment, as disclosed herein (e.g., the antibodies described above or otherwise provided for in the present disclosure), and instructions for use.

BRIEF DESCRIPTION OF DRAWINGS

This disclosure will be more fully understood from the following detailed description taken in conjunction with the accompanying drawings, in which.

DETAILED DESCRIPTION

Figure 1:
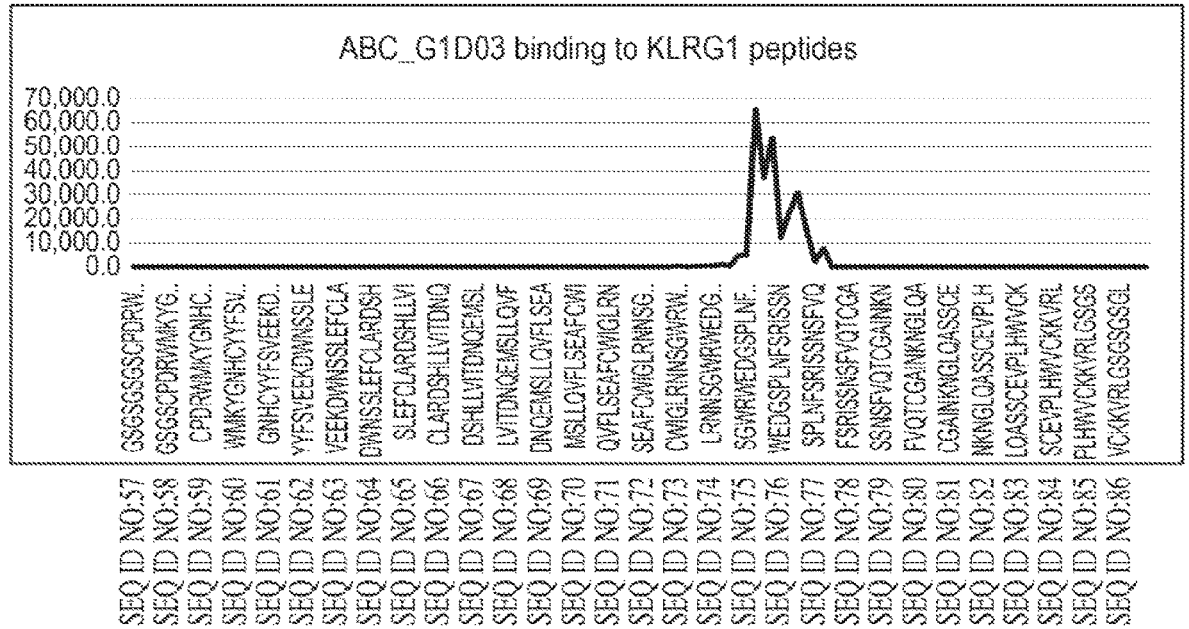
FIG. 1 provides one exemplary embodiment of peptide mapping of binding epitope of ABC_G1D03, showing binding of the antibody to a peptide sequence defined by the amino acids "PLNFSRI" (SEQ ID NO:56)

Certain exemplary embodiments will now be described to provide an overall understanding of the principles of the structure, function, manufacture, and use of the antibodies, fragments thereof, compositions of matter, kits, and related methods and therapies disclosed herein. Those skilled in the art will understand that the disclosures described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

Killer cell lectin-like receptor G1 (KLRG1) is a type II transmembrane protein which can function as co-inhibitory receptor by modulating the activity of T and NK cells. The extracellular portion of KLRG1 contains a C-type lectin domain whose known ligands are cadherins. The intracellular portion of KLRG1 contains an immunoreceptor tyrosine-based inhibitory motif (ITIM) domain responsible for co-inhibition of T cell receptor (TCR) mediated signaling. KLRG1 ligands include E-cadherin, N-cadherin, R-cadherin, and combinations thereof.

The receptor killer cell lectin-like receptor G1 (KLRG1) is expressed on T and NK cells which bind to ligands on epithelial and mesenchymal cells. The ligands for KLRG1 can be E-cadherin, N-cadherin, and R-cadherin.

In humans, KLRG1 expression is generally confined to cells of the immune systems, and specifically to CD8 positive T cells, NK cells, and, to a lesser extent, CD4 positive T cells. KLRG1 expression has been associated with the late differentiated phenotype. As antigen specific T cells differentiate they can acquire increased expression of cytotoxic molecules, and therefore can have increased cytotoxic potential.

The present disclosure is based, at least in part, on the discovery described in PCT Application No. PCT/US2017/051776—that KLRG1, a cell surface marker known to be present on senescent cytotoxic T cells, is also present on cytotoxic T cells with high-killing potential. For example, in the case of inclusion body myositis, KLRG1 can mark T cells that are directly killing healthy muscle cells.

Thus, KLRG1-expressing T cells and/or NK cells can be pathogenic and are therefore an advantageous target for cell depletion therapy. For example, administering to a subject in need of an effective amount of KLRG1 depleting agent (e.g., a KLRG1-expressing-cell depleting agent) with antibody dependent cellular cytotoxicity (ADCC) effector function can eliminate or reduce the number of cytotoxic T cells and/or NK cells injuring healthy cells as, for example, in autoimmune diseases and in transplant disorders.

Methods comprising administering a KLRG1-expressing-cell depleting agent are also advantageous in treating patients with cancer cells expressing KLGR1.

Markedly, the KLRG1-expressing-cell depleting agents disclosed herein have the additional property of not interrupting KLRG1's function as a Lymphocyte co-inhibitory receptor(s) mediated by the binding of E-cadherin, N-cadherin, R-cadherin, or a combination thereof, to the extracellular domain of KLRG1.

A prominent biological function of cell surface KLRG1 is to inhibit cytotoxicity and proliferation of cytotoxic T cells and/or NK cells by functioning as a lymphocyte co-inhibitory receptor. Lymphocyte co-inhibitory receptors modulate the action of the adaptive immune system, e.g., T cells and NK cells, in response to activating signals such as antigenic peptides in the context of the major histocompatibility complex (MHC) binding to the T cell receptor (TCR). Other co-inhibitory receptors known in the art include PD-1, LAG-3, TIM-3, and CTLA4. The action of co-inhibitory receptors can generally be carried out by binding a ligand to the extracellular domain of the co-inhibitory receptor, followed by recruitment of intracellular phosphatases by an immune-receptor tyrosine-based inhibition motif (ITIM) located in the intracellular domain of the co-inhibitory receptor. The action of co-inhibitory receptors is generally to dampen the immune response of TCR engagement.

By not interfering with the binding of E-cadherin, N-cadherin, or R-cadherin to the extracellular domain of KLRG1, the function of KLRG1 as a lymphocyte co-inhibitory receptor can be maintained. Because the KLRG1 binding agent does not release the checkpoint inhibition, the inhibition of the activation of potentially pathogenic CD8+ cytotoxic T and/or NK cells can be maintained.

Accordingly, the KLGR1 depleting agents, and related methods, disclosed herein not only deplete KLRG1 expressing T cells and/or NK cells in a subject, but additionally do not interfere with binding of E-cadherin, N-cadherin, or R-cadherin to the extracellular domain of KLRG1. The targeted depletion of KLRG1 expressing T cells and/or KLRG1 expressing NK cells and/or KLRG1 expressing cancer cells in a subject can be mediated by the fc region of the KLRG1 specific antibody or antigen binding fragment thereof and/or by an fc peptide conjugated to a KLRG1 specific antigen binding fragment thereof, and/or by a cytotoxic agent conjugated to a KLRG1 specific antibody or antigen binding fragment thereof. International Patent Application Publication No. WO 02/44215 describes binding molecules which comprise or consist of the antigen binding site of an antibody and a peptide binding Fc-effector molecule.

Selected Embodiments of the Present Disclosure

Disclosed herein are methods of depleting KLRG1 expressing T cells and/or NK cells in a subject in need of treatment, without interfering with binding of E-cadherin, N-cadherin, or R-cadherin to the extracellular domain of KLRG1. Methods provided for herein include delivering to a subject in need of treatment an effective amount of a KLGR1 depleting agent, such as an antibody, or a fragment thereof, that specifically binds to the extracellular domain of KLRG1 but does not compete with binding of E-cadherin, N-cadherin, or R-cadherin to the extracellular domain of KLRG1, thereby depleting KLRG1 expressing T cells in the subject.

Also disclosed herein are methods of selectively depleting KLRG1 expressing CD8 effector T cells, but not naïve T cells or regulatory T cells, that includes delivering to a subject an effective amount of antibody, or a fragment thereof, such that the antibody, or fragment thereof, specifically binds to the extracellular domain of KLRG1 but does not compete with binding of at least one of E-cadherin, N-cadherin, or R-cadherin to the extracellular domain of KLRG1, thereby selectively depleting KLRG1 expressing CD8 effector T cells.

In some embodiments of the methods, the antibody, or a fragment thereof, comprises a heavy chain variable region that includes three complementarity determining regions of an amino acid sequence of SEQ ID NO:4, SEQ ID NO:6, SEQ ID NO:8, SEQ ID NO: 10, SEQ ID NO: 12, or SEQ ID NO:14, and/or the antibody, or a fragment thereof, comprises a light chain variable region that includes the three complementarity determining regions of the amino acid sequence of SEQ ID NO:5, SEQ ID NO: 7, SEQ ID NO:9, SEQ ID NO: 11, SEQ ID NO: 13, or SEQ ID NO: 15.

In some embodiments of the methods, the KLRG1 can be human KLRG1 or Cyano KLRG1.

In some embodiments of the methods, the antibody, or a fragment thereof, includes a monoclonal antibody, or a fragment or derivative thereof. In some aspects, the monoclonal antibody, or a fragment thereof, can specifically bind the epitope PLNFSRI (SEQ ID NO:56), or a fragment thereof, comprising at least five (5) contiguous amino acids. The monoclonal antibody, or a fragment thereof, can comprise a heavy chain variable region that can include the amino acid sequence of SEQ ID NO:4, or a sequence approximately at least 90% identical thereto. In some aspects, the monoclonal antibody, or a fragment thereof, can comprise a light chain variable region that can include the amino acid sequence of SEQ ID NO:5, or a sequence approximately at least 90% identical thereto. In some aspects, the monoclonal antibody, or a fragment thereof, can comprise a heavy chain variable region that can include the amino acid sequence of SEQ ID NO:6, or a sequence approximately at least 90% identical thereto. In some aspects, the monoclonal antibody, or a fragment thereof, can comprise a light chain variable region that can include the amino acid sequence of SEQ ID NO:7, or a sequence approximately at least 90% identical thereto. In some aspects, the monoclonal antibody, or a fragment thereof, can comprise a heavy chain variable region that can include the amino acid sequence of SEQ ID NO: 8, or a sequence approximately at least 90% identical thereto. 11. In some aspects, the monoclonal antibody, or a fragment thereof, can comprise a light chain variable region that can include the amino acid sequence of SEQ ID NO:9, or a sequence approximately at least 90% identical thereto. In some aspects, the monoclonal antibody, or a fragment thereof, can comprise a heavy chain variable region that can include the amino acid sequence of SEQ ID NO: 10, or a sequence approximately at least 90% identical thereto. In some aspects, the monoclonal antibody, or a fragment thereof, can comprise a light chain variable region that can include the amino acid sequence of SEQ ID NO: 11, or a sequence approximately at least 90% identical thereto. In some aspects, the monoclonal antibody, or a fragment thereof, can comprise a heavy chain variable region that can include the amino acid sequence of SEQ ID NO: 12, or a sequence approximately at least 90% identical thereto. In some aspects, the monoclonal antibody, or a fragment thereof, can comprise a light chain variable region that can include the amino acid sequence of SEQ ID NO: 13, or a sequence approximately at least 90% identical thereto. In some aspects, the monoclonal antibody, or a fragment thereof, can comprise a heavy chain variable region that can include the amino acid sequence of SEQ ID NO: 14, or a sequence approximately at least 90% identical thereto. In some aspects, the monoclonal antibody, or a fragment thereof, can comprise a light chain variable region that can include the amino acid sequence of SEQ ID NO: 15, or a sequence approximately at least 90% identical thereto. In some aspects, the monoclonal antibody, or a fragment thereof, can include a chimeric antibody, or a fragment thereof. In some aspects, the monoclonal antibody, or a fragment thereof, can include a humanized antibody, or a fragment thereof.

Disclosed herein are methods of treating a disorder associated with excess or unwanted KLRG1 expressing T cells in a subject in need of treatment in which the method includes delivering to the subject a therapeutically effective amount of a KLRG1 depleting agent. The KLRG1 depleting agent can include an antibody, or a fragment thereof, that specifically binds to the extracellular domain of KLRG1 without interfering with binding of E-cadherin, N-cadherin, or R-cadherin to the extracellular domain of KLRG1, and can deplete KLRG1 expressing T cells, with the delivery to the subject depleting the excess or unwanted KLRG1 expressing T cells. Such delivery can be performed in such a way that delivery does not release checkpoint inhibition and subsequent activation of pathogenic CD8+ cytotoxic T and/or NK cells directed to self-tissues, thereby treating the disorder.

In some embodiments of the methods, the antibody, or a fragment thereof, comprises a heavy chain variable region that includes three complementarity determining regions of the amino acid sequence of SEQ ID NO:4, SEQ ID NO:6, SEQ ID NO:8, SEQ ID NO: 10, SEQ ID NO: 12, or SEQ ID NO:14; and/or the antibody, or a fragment thereof, comprises a light chain variable region that includes three complementarity determining regions of the amino acid sequence of SEQ ID NO:5, SEQ ID NO:7, SEQ ID NO:9, SEQ ID NO: 11, SEQ ID NO: 13, or SEQ ID NO:15. In some embodiments of the method, the disorder can be a transplant-related disorder, with the delivery to the subject depleting KLRG1 expressing pathogenic T cells and/or NK cells attacking transplanted tissues in the subject. In some embodiments of the method, the disorder can be an autoimmune disease, with the delivery to the subject depleting KLRG1 expressing pathogenic T cells and/or NK cells attacking self-tissues in the subject.

Disclosed herein are methods of treating cancer in a subject, with the cancer including cancer cells that express KLRG1. The methods can include delivering to the subject a therapeutically effective amount of a KLRG1 depleting agent, such an antibody, or a fragment thereof, that specifically binds to the extracellular domain of KLRG1 without interfering with binding by E-cadherin, N-cadherin, or R-cadherin to the extracellular domain of KLRG1. The delivery to the subject can deplete the cancer cells expressing KLRG1, and the delivery can do so while not releasing checkpoint inhibition and subsequent activation of pathogenic CD8+ cytotoxic T and/or NK cells directed to self-tissues.

In some embodiments of the methods, the antibody, or a fragment thereof, comprises a heavy chain variable region that includes three complementarity determining regions of the amino acid sequence of SEQ ID NO:4, SEQ ID NO:6, SEQ ID NO:8, SEQ ID NO: 10, SEQ ID NO: 12, or SEQ ID NO:14; and/or the antibody, or a fragment thereof, comprises a light chain variable region that includes three complementarity determining regions of the amino acid sequence of SEQ ID NO:5, SEQ ID NO:7, SEQ ID NO:9, SEQ ID NO:11, SEQ ID NO: 13, or SEQ ID NO:15.

Disclosed herein are adjunct therapies for treatment of cancer in a subject, such as subject that is undergoing checkpoint therapy. The methods can be performed regardless of whether the cancer expresses KLRG1. The provided for adjunct therapies can include delivering to the subject a therapeutically effective amount of a KLRG1 depleting agent, such an antibody, or a fragment thereof, that specifically binds to the extracellular domain of KLRG1 without interfering with binding by E-cadherin, N-cadherin, or R-cadherin to the extracellular domain of KLRG1. The delivery to the subject can deplete KLRG1 expressing pathogenic T cells and/or NK cells attacking self-tissues in the subject.

In some embodiments of the methods, the antibody, or a fragment thereof, comprises a heavy chain variable region that includes three complementarity determining regions of the amino acid sequence of SEQ ID NO:4, SEQ ID NO:6, SEQ ID NO:8, SEQ ID NO:10, SEQ ID NO: 12, or SEQ ID NO:14; and/or the antibody, or a fragment thereof, comprises a light chain variable region that includes three complementarity determining regions of the amino acid sequence of SEQ ID NO:5, SEQ ID NO:7, SEQ ID NO:9, SEQ ID NO: 11, SEQ ID NO: 13, or SEQ ID NO:15.

Disclosed herein are methods of depleting KLRG1 expressing cells in a mixed population of cells. The KLRG1 expressing cells can include one or more cells selected from a group consisting of T cells and/or NK cells and/or cancer cells. The method can include delivering to the mixed population of cells an effective amount of a KLRG1 depleting agent, such as an antibody, or a fragment thereof, that specifically binds to KLRG1 and depletes KLRG1 expressing T cells and/or NK cells and/or cancer cells, thereby depleting KLRG1 expressing T cells and/or NK cells and/or cancer cells in the mixed population of cells.

In some embodiments of the methods, the antibody, or a fragment thereof, comprises a heavy chain variable region that includes three complementarity determining regions of the amino acid sequence of SEQ ID NO:4, SEQ ID NO:6, SEQ ID NO:8, SEQ ID NO: 10, SEQ ID NO: 12, or SEQ ID NO:14; and/or the antibody, or a fragment thereof, comprises a light chain variable region that includes three complementarity determining regions of the amino acid sequence of SEQ ID NO:5, SEQ ID NO:7, SEQ ID NO:9, SEQ ID NO:11, SEQ ID NO: 13, or SEQ ID NO:15.

Disclosed herein are KLRG1 depleting agents that specifically bind to an extracellular domain of KLRG1 but do not compete with E-cadherin, N-cadherin, or R-cadherin binding to KLRG1, and deplete cells expressing KLGR1 when administered to a subject. The KLRG1 depleting agent can include an antibody, or a fragment thereof, that specifically binds to an extracellular domain of KLRG1 but does not compete with E-cadherin, N-cadherin, or R-cadherin binding to KLRG1, and depletes cells expressing KLGR1 when administered to a subject.

In some embodiments, the antibody, or a fragment thereof, comprises a heavy chain variable region that includes three complementarity determining regions of the amino acid sequence of SEQ ID NO:4, SEQ ID NO:6, SEQ ID NO:8, SEQ ID NO: 10, SEQ ID NO: 12, or SEQ ID NO:14; and/or the antibody, or a fragment thereof, comprises a light chain variable region that includes three complementarity determining regions of the amino acid sequence of SEQ ID NO:5, SEQ ID NO:7, SEQ ID NO:9, SEQ ID NO: 11, SEQ ID NO: 13, or SEQ ID NO: 15. In some embodiments, the KLRG1 can be human KLRG1 or Cyano KLRG1. In some embodiments, the antibody, or a fragment thereof, can include a monoclonal antibody, or a fragment or derivative thereof. In some embodiments, the monoclonal antibody, or a fragment thereof, can specifically bind the epitope PLNFSRI (SEQ ID NO:56), or a fragment thereof, comprising at least five (5) contiguous amino acids. In some aspects, the monoclonal antibody, or a fragment thereof, can comprise a heavy chain variable region that can include the amino acid sequence of SEQ ID NO:4, or a sequence approximately at least 90% identical thereto. In some aspects, the monoclonal antibody, or a fragment thereof, can comprise a light chain variable region that can include the amino acid sequence of SEQ ID NO:5, or a sequence approximately at least 90% identical thereto. In some aspects, the monoclonal antibody, or a fragment thereof, can comprise a heavy chain variable region that includes the amino acid sequence of SEQ ID NO:6, or a sequence approximately at least 90% identical thereto. In some aspects, the monoclonal antibody, or a fragment thereof, can comprise a light chain variable region that includes the amino acid sequence of SEQ ID NO:7, or a sequence approximately at least 90% identical thereto. In some aspects, the monoclonal antibody, or a fragment thereof, can comprise a heavy chain variable region that includes the amino acid sequence of SEQ ID NO: 8, or a sequence approximately at least 90% identical thereto. In some aspects, the monoclonal antibody, or a fragment thereof, can comprise a light chain variable region that includes the amino acid sequence of SEQ ID NO:9, or a sequence approximately at least 90% identical thereto. In some aspects, the monoclonal antibody, or a fragment thereof, can comprise a heavy chain variable region that includes the amino acid sequence of SEQ ID NO: 10, or a sequence approximately at least 90% identical thereto. In some aspects, the monoclonal antibody, or a fragment thereof, can comprise a light chain variable region that includes the amino acid sequence of SEQ ID NO: 11, or a sequence approximately at least 90% identical thereto. In some aspects, the monoclonal antibody, or a fragment thereof, can comprise a heavy chain variable region that includes the amino acid sequence of SEQ ID NO: 12, or a sequence approximately at least 90% identical thereto. In some aspects, the monoclonal antibody, or a fragment thereof, can comprise a light chain variable region that includes the amino acid sequence of SEQ ID NO: 13, or a sequence approximately at least 90% identical thereto. In some aspects, the monoclonal antibody, or a fragment thereof, can comprise a heavy chain variable region that includes the amino acid sequence of SEQ ID NO: 14, or a sequence approximately at least 90% identical thereto. In some aspects, the monoclonal antibody, or a fragment thereof, can comprise a light chain variable region that includes the amino acid sequence of SEQ ID NO: 15, or a sequence approximately at least 90% identical thereto. In some aspects, the monoclonal antibody, or a fragment thereof, can include a chimeric antibody, or a fragment thereof. In some aspects, the monoclonal antibody, or a fragment thereof, can include a humanized antibody, or a fragment thereof. Disclosed herein are pharmaceutical compositions that include one or more of the above monoclonal antibodies, or a fragment thereof, and a pharmaceutically acceptable carrier. A person skilled in the art, in view of the present disclosure, will understand various pharmaceutically acceptable carriers that can be used, including but not limited to (1) sugars, such as lactose, glucose and sucrose: (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) histidine buffered solutions; and (21) other non-toxic compatible substances employed in pharmaceutical formulations. Disclosed herein are also kits that can include one or more of the above monoclonal antibodies, or a fragment(s) thereof, and instructions for use. It will be appreciated that to the extent the term "fragment" is used herein, the fragment can also be more than one fragment, whether or not the term "fragment(s)" is used.

Definitions

Unless otherwise defined, all technical and scientific terms used herein have the same meaning as commonly understood by one skilled in the art to which this present disclosure belongs. The terminology used in the description of the present disclosure herein is for the purpose of describing particular embodiments only and is not intended to be limiting of the present disclosure and any invention(s) described or otherwise provided for herein.

Amino acids are represented herein by either the one-letter code, or the three-letter code, both in accordance with 37 C.F.R. § 1.822 and established usage.

All publications, patent applications, patents, patent publications, and other references cited herein are incorporated by reference in their entireties for the teachings relevant to the sentence and/or paragraph in which the reference is presented.

As used in the description of the present disclosure and the appended claims, the singular forms "a," "an," and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The terms "about" and "approximately" as used herein when referring to a measurable value such as an amount of polypeptide, dose, time, temperature, enzymatic activity or other biological activity and the like, is meant to encompass variations of ±20%, ±10%, ±5%, ±1%, ±0.5%, or even ±0.1% of the specified amount.

The transitional phrase "consisting essentially of" means that the scope of a claim is to be interpreted to encompass the specified materials or steps recited in the claim, "and those that do not materially affect the basic and novel characteristic(s)" of the claimed invention. See In re Herz, 537 F.2d 549, 551-52, 190 USPQ 461, 463 (CCPA 1976) (emphasis in the original); see also MPEP § 2111.03.

The term "consists essentially of" (and grammatical variants), as applied to a polynucleotide or polypeptide sequence of this present disclosure, means a polynucleotide or polypeptide that consists of both the recited sequence (e.g., SEQ ID NO) and a total of ten or less (e.g., 1, 2, 3, 4, 5, 6, 7, 8, 9, or 10) additional amino acids on the N-terminal and/or C-terminal ends of the recited sequence such that the function of polypeptide is not materially altered. The total of ten or less additional amino acids can include the total number of additional amino acids on both ends added together.

An "effective amount" as used herein is an amount that provides a desired effect. The term "effective amount" refers to a dosage or amount that is sufficient to reduce the activity of KLRG1 to result in amelioration of symptoms in a patient or to achieve a desired biological outcome, e.g., reduced activity of KLRG1, modulation of lymphocyte co-inhibition response, increased or decreased activation of cytotoxic T and NK cells, or increased or decreased release of IFNγ by cytotoxic T cells or NK cells.

A "therapeutically effective" amount as used herein is an amount that provides some improvement or benefit to the subject. Alternatively stated, a "therapeutically effective" amount is an amount that will provide some alleviation, mitigation, or decrease in at least one clinical symptom in the subject. Those skilled in the art will appreciate that the therapeutic effects need not be complete or curative, as long as some benefit is provided to the subject.

By the terms "treat," "treating," or "treatment of," it is intended that the severity of the condition of the subject is reduced, or at least partially improved or modified, and that some alleviation, mitigation, or decrease in at least one clinical symptom is achieved.

The term "deplete" as used herein with respect to T cells and/or NK cells and/or KLRG1 expressing cancer cells refers to a measurable decrease in the number of said cells in a subject or in a sample. The reduction can be at least about 10%, e.g., at least about 20%, about 30%, about 40%, about 50%, about 60%, about 70%, about 80%, about 90%, about 95%, about 96%, about 97%, about 98%, about 99%, or more. In certain embodiments, the term refers to a decrease in the number of T cells and/or NK cells and/or KLRG1 expressing cancer cells in a subject or in a sample to an amount below detectable limits.

The term "autoimmune disorders" as used herein refers to any disorder associated with an autoimmune reaction. Examples include, without limitation, multiple sclerosis, Crohn's disease, ulcerative colitis, lupus, inflammatory bowel syndrome, and irritable bowel syndrome.

The term "cancer" as used herein refers to any benign or malignant abnormal growth of cells. Examples include, without limitation, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma. In some embodiments, the cancer is selected from the group of tumor-forming cancers. A person skilled in the art will recognize which cancers fall within the purview of that group.

The term "transplant" refers to a section of tissue, or a complete organ, that is removed from its original natural site or host and transferred to a new position in the same person or in a separate individual. Methods for treating recipients of transplants relates to methods of inhibiting organ or tissue transplant rejection, particularly in mammals. More particularly, the present disclosure relates to methods of inhibiting transplant rejection in mammals in need thereof, which can include administering to such mammals a transplant rejection inhibiting amount of anti-KLRG1 binding agents, including antibodies which specifically bind KLRG1 and fragments thereof.

The term "isolated" can refer to a polypeptide that is substantially free of cellular material, viral material, and/or culture medium (when produced by recombinant DNA techniques), or chemical precursors or other chemicals (when chemically synthesized). Moreover, an "isolated fragment" is a fragment of a polypeptide that is not naturally occurring as a fragment and would not be found in the natural state. "Isolated" does not mean that the preparation is technically pure (homogeneous), but it is sufficiently pure to provide the polypeptide or nucleic acid in a form in which it can be used for the intended purpose. Thus, the term "isolated" refers to a molecule that is substantially free of its natural environment. For instance, an isolated protein is substantially free of cellular material or other proteins from the cell or tissue source from which it is derived. The term "isolated" also refers to preparations where the isolated protein is sufficiently pure to be administered as a pharmaceutical composition, or approximately at least 70-80% (w/w) pure, more preferably, approximately at least 80-90% (w/w) pure, even more preferably, approximately 90-95% pure; and, most preferably, approximately at least 95%, approximately at least 96%, approximately at least 97%, approximately at least 98%, approximately at least 99%, or approximately at least 100% (w/w) pure.

The term "fragment," as applied to a polypeptide, will be understood to mean an amino acid sequence of reduced length relative to a reference polypeptide or amino acid sequence and comprising, consisting essentially of, and/or consisting of an amino acid sequence of contiguous amino acids identical or almost identical (e.g., approximately 90%, approximately 92%, approximately 95%, approximately 98%, approximately 99% identical) to the reference polypeptide or amino acid sequence. Such a polypeptide fragment according to the present disclosure may be, where appropriate, included in a larger polypeptide of which it is a constituent. In some embodiments, such fragments can comprise, consist essentially of, and/or consist of peptides having a length of at least about 4, about 6, about 8, about 10, about 12, about 15, about 20, about 25, about 30, about 35, about 40, about 45, about 50, 7 about 5, about 100, about 150, about 200, or more consecutive amino acids of a polypeptide or amino acid sequence according to the present disclosure.

As used herein, the terms "protein" and "polypeptide" are used interchangeably and encompass both peptides and proteins, unless indicated otherwise.

A "fusion protein" is a polypeptide produced when two heterologous nucleotide sequences or fragments thereof coding for two (or more) different polypeptides not found fused together in nature are fused together in the correct translational reading frame. Illustrative fusion polypeptides include fusions of a polypeptide of the present disclosure (or a fragment thereof) to all or a portion of glutathionestransferase, maltose-binding protein, or a reporter protein (e.g., Green Fluorescent Protein, β-glucuronidase, β-galactosidase, luciferase, etc.), hemagglutinin, c-myc, FLAG epitope, etc.

As used herein, a "functional" polypeptide or "functional fragment" is one that substantially retains at least one biological activity normally associated with that polypeptide (e.g., target protein binding). In particular embodiments, the "functional" polypeptide or "functional fragment" substantially retains all of the activities possessed by the unmodified peptide. By "substantially retains" biological activity, it is meant that the polypeptide retains at least about 20%, about 30%, about 40%, about 50%, about 60%, about 75%, about 85%, about 90%, about 95%, about 97%, about 98%, about 99%, or more, of the biological activity of the native polypeptide (and can even have a higher level of activity than the native polypeptide). A "non-functional" polypeptide is one that exhibits little or essentially no detectable biological activity normally associated with the polypeptide (e.g., at most, only an insignificant amount, e.g., less than about 10% or even less than about 5%). Biological activities such as protein binding can be measured using assays that are well known in the art and as described herein.

Antibodies and Compositions

The present disclosure allows for the identification and characterization of antibodies that specifically bind to the extracellular domain of KLGR1 of cells without interfering with the binding of E-cadherin, R-cadherin, and/or N-cadherin to the extracellular domain of KLRG1. Such antibodies can advantageously be used to deplete cells expressing cell surface KLGR1 in a subject, e.g., for research or therapeutic purposes. Such antibodies can be used to treat disorders associated with pathogenic and autoimmune T cells as well as cancer cells expressing KLGR1. Accordingly, one aspect of the present disclosure relates to antibodies or fragments thereof that specifically bind to the extracellular domain of KLRG1 and depletes cells expressing KLRG1 when administered to a subject. Such antibodies, or fragments thereof, can be used as an adjunct therapy for cancer treatment, regardless if the cancer cells express KLRG1.

Intact antibodies, also known as immunoglobulins, are typically tetrameric glycosylated proteins composed of two light (L) chains of approximately 25 kDa each and two heavy (H) chains of approximately 50 kDa each. Two types of light chain, designated as the λ chain and the k chain, are found in antibodies. Depending on the amino acid sequence of the constant domain of heavy chains, immunoglobulins can be assigned to five major classes: A, D, E, G, and M, and several of these may be further divided into subclasses (isotypes), e.g., IgG1, IgG2, IgG3, IgG4, IgA1, and IgA2.

The subunit structures and three-dimensional configurations of different classes of immunoglobulins are well known in the art. Briefly, each light chain can be composed of an N-terminal variable domain (VL) and a constant domain (CL). Each heavy chain can be composed of an N-terminal variable domain (VH), three or four constant domains (CH), and a hinge region. The CH domain most proximal to VH is designated as CH1. The VH and VL domains consist or comprise of four regions of relatively conserved sequence called framework regions (FR1, FR2, FR3, and FR4), which form a scaffold for three regions of hypervariable sequence called complementarity determining regions (CDRs). The CDRs can contain most of the residues responsible for specific interactions with the antigen. The three CDRs are referred to as CDR1, CDR2, and CDR3. CDR constituents on the heavy chain are referred to as H1, H2, and H3, while CDR constituents on the light chain are referred to as L1, L2, and L3, accordingly. CDR3 and particularly H3, are the greatest source of molecular diversity within the antigen-binding domain. H3, for example, can be as short as two amino acid residues of greater than 26.

The Fab fragment (Fragment antigen-binding), or Fab, consists or comprises of the VH-CH1 and VL-CL domains covalently linked by a disulfide bond between the constant regions. Known to those skilled in the art, a Fab (50,000 daltons) is a monovalent fragment that is produced from IgG and IgM, consisting or comprising of the VH, CH1 and VL, CL regions, linked by an intramolecular disulfide bond. To overcome the tendency of non-covalently linked VH and VL domains in the Fv to dissociate when co-expressed in a host cell, a so-called single chain (sc) Fv fragment (scFv) can be constructed. In a scFv, a flexible and adequately long polypeptide links either the C-terminus of the VH to the N-terminus of the VL, or the C-terminus of the VL to the N-terminus of the VH. Most commonly, a 15-residue (Gly4Ser) 3 peptide can ne used as a linker, but other linkers are also known in the art.

Antibody diversity is a result of combinatorial assembly of multiple germline genes encoding variable regions and a variety of somatic events. The somatic events can include recombination of variable gene segments with diversity (D) and joining (J) gene segments to make a complete VH region and the recombination of variable and joining gene segments to make a complete VL region. The recombination process itself is imprecise, resulting in the loss or addition of amino acids at the V (D) J junctions. These mechanisms of diversity occur in the developing B cell prior to antigen exposure. After antigenic stimulation, the expressed antibody genes in B cells can undergo somatic mutation.

Based on the estimated number of germline gene segments, the random recombination of these segments, and random VH-VL pairing, up to approximately $1.6 \times 10^7$ different antibodies can be produced according to Fundamental Immunology, $3^{rd}$ ed., ed. Paul, Raven Press, New York, N.Y., 1993. When other processes which contribute to antibody diversity (such as somatic mutation) are taken into account, it is thought that upwards of approximately $1 \times 10^{10}$ different antibodies could be potentially generated, as supported by Immunoglobulin Genes, $2^{nd}$ ed., eds. Jonio et al., Academic Press, San Diego, Calif., 1995. Because of the many processes involved in antibody diversity, it is highly unlikely that independently generated antibodies will have identical amino acid sequences in the CDRs.

The present disclosure provides novel CDRs derived from human immunoglobulin gene libraries, which are effective in depleting cells expressing cell surface KLGR1. The scaffold structure for carrying a CDR can generally be, though is not limited to, an antibody heavy or light chain, or a portion thereof, in which the CDR is located at a location corresponding to the CDR of naturally occurring VH and VL. The structures and locations of immunoglobulin variable domains may be determined, for example, as described in Kabat et al., Sequences of Proteins of Immunological Interest, No. 91-3242, National Institutes of Health Publications, Bethesda, Md., 1991.

Depletion of KLGR1 Expressing Cells

Antibodies, such as those described herein, exhibit at least two functions in the immune system. They bind antigens, e.g., KLRG1, and eliminate these antigens, including cells expressing the antigen, via the immunoglobulin effector functions, including but not limited to activation of the complement system or interaction with cellular receptors (Fc receptors) on phagocytic cells such as macrophages, and/or other immune cells such as NK cells, leukocytes, platelets, and placental trophoblasts.

Antibody-dependent cellular phagocytosis (ADCP), antibody-dependent cellular cytotoxicity (ADCC), and complement-dependent cytotoxicity (CDC) are three well known antibody mediated mechanisms for killing, and thus depleting, target cells.

Though not bound by mechanism or theory, binding of the antibody to the target cell through the antigen binding region (variable domain) of the antibody can provide a linkage of the target cell to immune effectors through the Fc region(s) of the constant region of the antibody. In ADCC, typically the fc region of the antibody binds to FcγRIIIa receptor on the immune effector cell, e.g., an NK cell, which can then kill the target cell. In ADCP, typically the fc region of the antibody binds to FcγRIIa receptor on the immune effector cell, e.g., a macrophage cell, which can then engulf and kill the target cell. CDC is induced when the immune complex C1q binds to the fc region of the antibody bound to the target cell, triggering the formation of a membrane attack complex that punches holes into the surface of the target cell.

Thus, the constant region of the antibody mediates effector functions, including the activation of complement and interaction with Fc receptors, enabling effects such as ADCC, ADCP, or CDC. Neither CH1 nor Cκ or Cλ domains mediate effector functions, which is the reason why Fabs do not show ADCC, ADCP, or CDC.

There are three classes of Fc gamma receptors, FcγRI (CD64), FcγRII (CD 32), and FcγRIII (CD 16). Only FcγRI is able to bind IgG in a monomeric form, and the affinity of FcγRI receptors compared to the immunoglobulin receptors FcγRII and FcγRIII is high. The high affinity receptor FcγR1 is constitutively expressed on monocytes, macrophages, and dendritic cells, and expression can be induced on neutrophils and eosinophils. Thus, these cells can be recruited to a target cell through antibody or antibody fragment thereof comprising fc region, bound to the target cell.

The FcγRIIa receptor is found on macrophages, monocytes, and neutrophils, and the FcγRIIb receptor is found on B-cells, macrophages, mast cells, and eosinophils. The FcγRIIIa receptor is found on NK cells, macrophages, eosinophils, monocytes, and T cells, and the FcγRIIIb receptor is highly expressed on neutrophils. Again, these various cell types can be recruited to a target cell by an antibody bound to the target cell through an antibody or antibody fragment thereof comprising the fc region, bound to the target cell.

Thus, the KLRG1 binding molecules, including antibodies and antigen binding fragments thereof, and methods thereof, including those pertaining to KLRG1 depletion in a subject or in vitro, in some aspects comprise a KLRG1 antigen binding site together with an antibody constant domain or fragment thereof. This can function to mediate an effector function, including but not limited to ADCC, ADCP, or CDC. In some aspects the KLRG1 binding molecule consists or comprises of the antigen binding site of an antibody and a peptide binding Fc-effector molecules, as described in International Patent Application Publication No. WO 02/44215.

Immunotoxins as Means for Depletion of KLGR1 Expressing Cells

In some aspects, the antibodies and/or antigen binding fragments thereof provided for by the instant disclosure are conjugated to a toxic agent, and thus do not necessarily rely on endogenous effector cells in ADCC, ADCP, or CDC to deplete the target cells, e.g., pathogenic cells and/or cancer cells expressing cell surface KLGR1.

Immunoconjugates which include one or more cytotoxins are referred to as "immunotoxins." Antibodies conjugated to a cytotoxic agent, drug, or the like are also known as antibody-drug conjugates (ADC). An immunoconjugate may have a half-life of sufficient periods of time for the antibody-drug conjugate to be internalized, degraded, and induce cell killing by the released toxin. A cytotoxin or cytotoxic agent can include any agent that is detrimental to (e.g., kills) cells. Suitable cytotoxic agents for forming immunoconjugates of the present disclosure include taxol, tubulysins, duostatins, cytochalasin B, gramicidin D, ethidium bromide, emetine, mitomycin, etoposide, tenoposide, vincristine, vinblastine, colchicin, doxorubicin, daunorubicin, dihydroxy anthracin dione, maytansine or an analog or derivative thereof, mitoxantrone, mithramycin, actinomycin D, 1-dehydrotestosterone, glucocorticoids, procaine, tetracaine, lidocaine, propranolol, and puromycin; calicheamicin or analogs or derivatives thereof, antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin; as well as duocarmycin A, duocarmycin SA, CC-1065 (a.k.a. rachelmycin), or analogs or derivatives of CC-1065), dolastatin, auristatin, pyrrolo[2,1-c][1,4]benzodiazepins (PDBs), indolinobenzodiazepine (IGNs) or analogues thereof, antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), anti-mitotic agents (e.g., tubulin-targeting agents), such as diphtheria toxin and related molecules (such as diphtheria A chain and active fragments thereof and hybrid molecules); ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, and enomycin toxins. Other suitable conjugated molecules include antimicrobial/lytic peptides such as CLIP, Magainin 2, mellitin, Cecropin, and P18; ribonuclease (RNase), DNase I, Staphylococcal enterotoxin-A, pokeweed antiviral protein, diphtherin toxin, and *Pseudomonas* endotoxin.

Supplemental Therapeutic Agents

The antibodies of the present disclosure, including fragments thereof and conjugates thereof, can optionally be delivered to a patient in conjunction with other therapeutic agents. The additional therapeutic agents can be delivered concurrently with the antibodies of the present disclosure. As used herein, the word "concurrently" means sufficiently close in time to produce a combined effect (that is, concurrently can be simultaneously, or it can be two or more events occurring within a short time period before or after each other).

In some embodiments the antibodies of the present disclosure can be administered in conjunction with anti-cancer agents, such as: 1) vinca alkaloids (e.g., vinblastine, vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide). In some embodiments the antibodies of the present disclosure can be administered in conjunction with anti-angiogenesis agents, such as antibodies to VEGF (e.g., bevacizumab (AVASTIN), ranibizumab (LUCENTIS)) and other promoters of angiogenesis (e.g., bFGF, angiopoietin-1), antibodies to alpha-v/beta-3 vascular integrin (e.g., VITAXIN), angiostatin, endostatin, dalteparin, ABT-510, CNGRC peptide TNF alpha conjugate, cyclophosphamide, combretastatin A4 phosphate, dimethylxanthenone acetic acid, docetaxel, lenalidomide, enzastaurin, paclitaxel, paclitaxel albumin-stabilized nanoparticle formulation (Abraxane), soy isoflavone (Genistein), tamoxifen citrate, thalidomide, ADH-1 (EXHERIN), AG-013736, AMG-706, AZD2171, sorafenib tosylate, BMS-582664, CHIR-265, pazopanib, PI-88, vatalanib, everolimus, suramin, sunitinib malate, XL184, ZD6474, ATN-161, cilengitide, and celecoxib.

In some embodiments, including but not limited to the treatment of an autoimmune disease or in transplantation treatment, the antibodies of the present disclosure can be administered in conjunction with immunosuppressive agents including, for example, cyclosporine A, rapamycin, glucocorticoids, azathioprine, mizoribine, aspirin derivatives, hydroxychloroquine, methotrexate, cyclophosphamide and FK506 (tacrolimus).

Antibody-Related Definitions

The term "antibody" or "antibodies" as used herein refers to all types of immunoglobulins, including IgG, IgM, IgA, IgD, and IgE. The antibody can be monoclonal or polyclonal and can be of any species of origin, including, for example, mouse, rat, rabbit, horse, goat, sheep, camel, or human, or can be a chimeric antibody. The antibodies can be recombinant monoclonal antibodies produced according to the methods disclosed, for example, in U.S. Pat. No. 4,474,893 or U.S. Pat. No. 4,816,567. The antibodies can also be chemically constructed, for example, according to the methods disclosed in U.S. Pat. No. 4,676,980.

The terms "antigen-binding domain," "antigen-binding fragment," and "binding fragment" refer to a part of an antibody molecule that comprises amino acids responsible for the specific binding between the antibody and the antigen. In instances where an antigen is large, the antigen-binding domain may only bind to a part of the antigen. A portion of the antigen molecule that is responsible for specific interactions with the antigen-binding domain is referred to as "epitope" or "antigenic determinant."

Though an antigen-binding domain typically comprises an antibody light chain variable region (VL) and an antibody heavy chain variable region (VH), however, it does not necessarily have to comprise both. For example, a so-called Fd antibody fragment consists only of a VH domain, but still retains some antigen-binding function of the intact antibody.

Anti-KLRG1 antibodies may optionally comprise antibody constant regions or parts thereof. For example, a VL domain may have attached, at its C terminus, antibody light chain constant domains including human Cκ or Cλ chains. Similarly, a specific antigen-binding domain based on a VH domain may have attached all or part of an immunoglobulin heavy chain derived from any antibody isotype, e.g., IgG, IgA, IgE, and IgM and any of the isotype subclasses, which include but are not limited to, IgG1 and IgG4. The DNA and amino acid sequences for the C-terminal fragment of are well known in the art.

The term "repertoire" refers to a genetically diverse collection of nucleotides derived wholly or partially from sequences that encode expressed immunoglobulins. The sequences can be generated by in vivo rearrangement of, e.g., V, D, and J segments for H chains and, e.g., V and J segment for L chains. Alternatively, the sequences may be generated from a cell line by in vitro stimulation, in response to which the rearrangement occurs. Alternatively, part or all of the sequences may be obtained by combining, e.g., unrearranged V segments with D and J segments, by nucleotide synthesis, randomized mutagenesis, and other methods, for example as disclosed in U.S. Pat. No. 5,565,332.

The terms "specific interaction" and "specific binding" refer to two molecules forming a complex that is relatively stable under physiologic conditions. Specific binding can be characterized by a high affinity and a low to moderate capacity, as distinguished from non-specific binding, which usually has a low affinity with a moderate to high capacity. Typically, binding is considered specific when the affinity constant $K_A$ is higher than approximately 106 M 1, or more preferably higher than approximately 108 M 1. If necessary, non-specific binding can be reduced without substantially affecting specific binding, for example, by varying the binding conditions. The appropriate binding conditions such as concentration of antibodies, ionic strength of the solution, temperature, time allowed for binding, concentration of a blocking agent (e.g., serum albumin, milk casein), etc., may be optimized by a skilled artisan using routine techniques.

In certain embodiments, the antibodies can specifically bind an epitope within the extracellular domain (ECD) of human or mouse or monkey KLRG1, with an affinity, as expressed in KD, of at least about 2 nM, about 1 nm, about 100 pM, about 10 pM, or about 5 pM. The amino acid sequences of ECDs of human and cynomolgus KLRG1 are set out in SEQ ID NO: 1 and SEQ ID NO:2, as listed in Working Example 1 below.

Antibody Binding Specificity

It is contemplated that antibodies of the present disclosure may also bind with other proteins, including, for example, recombinant proteins comprising all or a portion of KLRG1.

One skilled in the art will recognize that the antibodies of this present disclosure may be used to detect, measure, and inhibit proteins that differ somewhat from KLRG1. The antibodies can be expected to retain the specificity of binding so long as the target protein comprises a sequence which is at least about 60%, about 70%, about 80%, about 90%, about 95%, or more identical to any sequence of at least about 130, about 100, about 80, about 60, about 40, or about 20 of contiguous amino acids in the sequence set forth SEQ ID NO:1 or SEQ ID NO: 2. The percent identity is determined by standard alignment algorithms such as, for example, Basic Local Alignment Tool (BLAST) described in Altshul et al. (1990) J. Mol. Biol., 215:403-410, the algorithm of Needleman et al. (1970) J. Mol. Biol., 48:444-453, or the algorithm of Meyers et al. (1988) Comput. Appl. Biosci., 4:11-17.

In addition to the sequence homology analyses, epitope mapping (see, e.g., Epitope Mapping Protocols, ed. Morris, Humana Press, 1996) and secondary and tertiary structure analyses can be carried out to identify specific 3D structures assumed by the disclosed antibodies and their complexes with antigens. Such methods include, but are not limited to, X-ray crystallography (Engstom (1974) Biochem. Exp. Biol., 11:7-13) and computer modeling of virtual representations of the presently disclosed antibodies (Fletterick et al. (1986) Computer Graphics and Molecular Modeling, in Current Communications in Molecular Biology, Cold Spring Harbor Laboratory, Cold Spring Harbor, N.Y.).

Antibody Variants

This disclosure also provides methods for obtaining an antibody specific for KLRG1. Complementarity-determining regions (CDRs) in such antibodies are not limited to the specific sequences of VH and VL identified in the Working Examples below, and may include variants of these sequences that retain the ability to specifically bind KLRG1 while not interfering with the binding by KLRG1 and E-cadherin, N-cadherin, and R-cadherin. Such variants may be derived from the sequences listed in the Working Examples by a skilled artisan using techniques well known in the art. For example, amino acid substitutions, deletions, or additions, can be made in the framework regions (FRs) and/or in CDRs. While changes in the FRs can usually be designed to improve stability and immunogenicity of the antibody, changes in the CDRs can typically be designed to increase affinity of the antibody for its target.

Changes to FRs include, but are not limited to, humanizing a non-human derived or engineering certain framework residues that are important for antigen contact or for stabilizing the binding site, e.g., changing the class or subclass of the constant region, changing specific amino acid residues which might alter the effector function such as Fc receptor binding, e.g., as described in U.S. Pat. Nos. 5,624,821 and 5,648,260 and Lund et al. (1991) J. Immun. 147:2657-2662 and Morgan et al. (1995) Immunology 86:319-324, or changing the species from which the constant region is derived.

Variants of FRs also include naturally occurring immunoglobulin allotypes. Such affinity-increasing changes may be determined empirically by routine techniques that involve altering the CDR and testing the affinity antibody for its target. For example, conservative amino acid substitutions can be made within any one of the disclosed CDRs. Various alterations can be made according to the methods described, for example, in Antibody Engineering, 2nd ed., Oxford University Press, ed. Borrebaeck, 1995. These include but are not limited to nucleotide sequences that are altered by the substitution of different codons that encode a functionally equivalent amino acid residue within the sequence, thus producing a "silent" change. For example, the nonpolar amino acids include alanine, leucine, isoleucine, valine, proline, phenylalanine, tryptophan, and methionine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Substitutes for an amino acid within the sequence may be selected from other members of the class to which the amino acid belongs (see Table 6). Furthermore, any native residue in the polypeptide may also be substituted with alanine (see, e.g., MacLennan et al. (1998) Acta Physiol. Scand. Suppl. 643:55-67; Sasaki et al. (1998) Adv. Biophys. 35:1-24).

The phrase "substantially as set out" means that the relevant CDR, VH, or VL domain of the resent disclosure will be either identical to, or have only insubstantial differences in the specified regions (e.g., a CDR) from the sequence of which is set out. Insubstantial differences include minor amino acid changes, such as substitutions of one (1) or two (2) out of any five (5) amino acids in the sequence of a specified region.

The term "KLRG1 activity" refers to one or more lymphocyte co-inhibitory activities associated with KLRG1. For example, KLRG1 activity may mean modulation of cytotoxic T and NK cell activation.

The term "modulate," and its cognates, refer to a reduction or an increase in the activity of KLRG1 associated with activation of T cells and NK cells due to its interaction with an anti-KLRG1 antibody, wherein the reduction or increase is relative to the activity of KLRG1 in the absence of the same antibody. A reduction or an increase in activity is preferably at least about 10%, about 20%, about 30%, about 40%, about 50%, about 60%, about 70%, about 80%, about 90%, or more. When KLRG1 activity is reduced, the terms "modulatory" and "modulate" are interchangeable with the terms "inhibitory" and "inhibit." When KLRG1 activity is increased, the terms "modulatory" and "modulate" are interchangeable with the terms "activating" and "activate."

Antibody fragments included within the scope of the present disclosure include, for example: Fab, Fab', F (ab') 2, and Fv fragments; domain antibodies, diabodies; vaccibodies, linear antibodies; single-chain antibody molecules; and multispecific antibodies formed from antibody fragments. Such fragments can be produced by known techniques. For example, F (ab') 2 fragments can be produced by pepsin digestion of the antibody molecule, and Fab fragments can be generated by reducing the disulfide bridges of the F (ab') 2 fragments. Alternatively, Fab expression libraries can be constructed to allow rapid and easy identification of monoclonal Fab fragments with the desired specificity (see Huse et al, Science 1989 Dec. 8; 246 (4935): 1275-1281).

Antibodies of the present disclosure may be altered or mutated for compatibility with species other than the species in which the antibody was produced. For example, antibodies may be humanized or camelized. Humanized forms of non-human (e.g., murine) antibodies are chimeric immunoglobulins, immunoglobulin chains or fragments thereof (such as Fv, Fab, Fab1, F(ab')2 or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat, or rabbit having the desired specificity, affinity, and capacity. In some instances, Fv framework residues of the human immunoglobulin can be replaced by corresponding non-human residues. Humanized antibodies may also comprise residues which are found neither in the recipient antibody nor in the imported CDR or framework sequences. In general, the humanized antibody can comprise substantially all of at least one, and typically two, variable domains, in which all or substantially all of the CDR regions correspond to those of a non-human immunoglobulin and all or substantially all of the framework (FR) regions (i.e., the sequences between the CDR regions) are those of a human immunoglobulin consensus sequence. The humanized antibody optimally also can comprise at least a portion of an immunoglobulin constant region (Fc), typically that of a human immunoglobulin.

In certain embodiments, the VH and/or VL domains may be germlined, i.e., the framework regions (FRs) of these domains are mutated using conventional molecular biology techniques to match those produced by the germline cells. In other embodiments, the framework sequences remain diverged from the consensus germline sequences.

Methods for humanizing non-human antibodies are well known in the art. The present disclosure, and any invention(s) provided for herein, is not limited to any particular source, species of origin, or method of production. Generally, a humanized antibody has one or more amino acid residues introduced into it from a source that is non-human. These non-human amino acid residues are often referred to as "import" residues, which are typically taken from an "import" variable domain. Humanization can essentially be performed following the method of Winter and co-workers (Jones et al, Nature 321:522 (1986); Riechmann et al, Nature 332:323 (1988); Verhoeyen et al, Science 239:1534 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues (e.g., all of the CDRs or a portion thereof), and possibly some FR residues, are substituted by residues from analogous sites in rodent antibodies.

Human antibodies can also be produced using various techniques known in the art, including phage display libraries (Hoogenboom and Winter, J. Mol. Biol. 227:381 (1991); Marks et al, J. Mol Biol 222:581 (1991)). The techniques of Cole et al and Boerner et al are also available for the preparation of human monoclonal antibodies (Cole et al, Monoclonal Antibodies and Cancer Therapy, Alan R. Liss, p. 77 (1985) and Boerner et al, J. Immunol. 147:86 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 9,434,782, 9,253,965, 5,545,807, 5,545,806, 5,569,825, 5,625,126, 5,633,425, and 5,661,016, and in the following scientific publications: Lee, E-Chiang et al. "Complete humanization of the mouse immunoglobulin loci enables efficient therapeutic antibody discovery" Nature Biotechnology volume 32, pages 356-363 (2014); Marks et ah, Bio/Technology 10:779 (1992); Lonberg et 1, Nature 368:856 (1994); Morrison, Nature 368:812 (1994); Fishwild et ah, Nature Biotechnol. 14: M5 (1996); Neuberger, Nature Biotechnoh 14:826 (1 96); Lonberg and Huszar, Intern, Rev. Immunol 13:65 (1995).

Monoclonal antibodies used to carry out the present disclosure can be produced in a hybridoma cell line according to the technique of Kohler and Milstein, Nature 265:495 (1975). For example, a solution containing the appropriate antigen can be injected into a mouse and, after a sufficient time, the mouse sacrificed, and spleen cells obtained. The spleen cells can then be immortalized by fusing them, for example with myeloma cells or with lymphoma cells, typically in the presence of polyethylene glycol, to produce hybridoma cells. The hybridoma cells can then be grown in a suitable medium and the supernatant screened for monoclonal antibodies having the desired specificity. Monoclonal Fab fragments can be produced in $E.$ $coli$ by recombinant techniques known to those skilled in the art. Antibodies specific to the target polypeptide can also be obtained by phage display techniques known in the art.

Various immunoassays can be used for screening to identify antibodies having the desired specificity for the extracellular domain of KLRG1. Numerous protocols for competitive binding or immunoradiometric assays using monoclonal antibodies with established specificity are well known in the art. Such immunoassays typically involve the measurement of complex formation between an antigen and its specific antibody (e.g., antigen/antibody complex formation). A two-site, monoclonal-based immunoassay utilizing monoclonal antibodies reactive to two non-interfering epitopes on the polypeptides or peptides of this disclosure can be used as well as a competitive binding assay.

Further to the conjugates described above, anti-KLRG1 antibodies described herein can be conjugated to a solid support (e.g., beads, plates, slides, or wells formed from materials such as latex or polystyrene) in accordance with known techniques. Anti-KLRG1 antibodies described herein can likewise be conjugated to detectable groups such as radiolabels (e.g., $^{35}S$, $^{125}I$, $^{131}I$ or $^{99m}Tc$, which may also be attached to antibodies using conventional chemistry), enzyme labels (e.g., horseradish peroxidase, alkaline phosphatase), and fluorescence labels (e.g., fluorescein) in accordance with known techniques. Detectable labels further include chemical moieties such as biotin, which may be detected via binding to a specific cognate detectable moiety, e.g., labeled avidin. Determination of the formation of an antibody/antigen complex in the methods of this disclosure can be by detection of, for example, precipitation, agglutination, flocculation, radioactivity, color development or change, fluorescence, luminescence, etc., and is well known in the art.

As described above, anti-KLRG1 antibodies described herein can be linked to another functional molecule, e.g., another peptide or protein (albumin, another antibody, etc.), toxin, radioisotope, cytotoxic or cytostatic agents. For example, the antibodies can be linked by chemical cross-linking or by recombinant methods. The antibodies may also be linked to one of a variety of nonproteinaceous polymers, e.g., polyethylene glycol, polypropylene glycol, or polyoxy-alkylenes, in the manner set forth in U.S. Pat. Nos. 4,640,835, 4,496,689, 4,301,144, 4,670,417, 4,791,192, and 4,179,337. The antibodies can be chemically modified by covalent conjugation to a polymer, for example, to increase their circulating half-life. Exemplary polymers and methods to attach them are also shown in U.S. Pat. Nos. 4,766,106, 4,179,337, 4,495,285, and 4,609,546.

Anti-KLRG1 antibodies described herein may also be altered to have a glycosylation pattern that differs from the native pattern. For example, one or more carbohydrate moieties can be deleted and/or one or more glycosylation sites added to the original antibody. Addition of glycosylation sites to the presently disclosed antibodies may be accomplished by altering the amino acid sequence to contain glycosylation site consensus sequences known in the art. Another means of increasing the number of carbohydrate moieties on the antibodies is by chemical or enzymatic coupling of glycosides to the amino acid residues of the antibody. Such methods are described in International Patent Application Publication No. WO 87/05330, and in Aplin et al. (1981) CRC Crit. Rev. Biochem., 22:259-306. Removal of any carbohydrate moieties from the antibodies may be accomplished chemically or enzymatically, for example, as described by Hakimuddin et al. (1987) Arch. Biochem. Biophys., 259:52; and Edge et al. (1981) Anal. Biochem., 118:131 and by Thotakura et al.

Further Embodiments

In certain embodiments, the monoclonal antibody, or a fragment thereof, can be a chimeric antibody or a humanized antibody. In additional embodiments, the chimeric or humanized antibody comprises at least a portion of the CDRs of the monoclonal antibody. As used herein, a "portion" of a CDR is defined as one or more of the three loops from each of the light and heavy chain that make up the CDRs (e.g., from 1-6 of the CDRs) or one or more portions of a loop comprising, consisting essentially of, or consisting of at least three contiguous amino acids. For example, the chimeric or humanized antibody may comprise 1, 2, 3, 4, 5, or 6 CDR loops, portions of 1, 2, 3, 4, 5, or 6 CDR loops, or a mixture thereof, in any combination.

In some embodiments, the antibody, or a fragment thereof, comprises a heavy chain variable region that includes the amino acid sequence of any one of SEQ ID NOs: 4, 6, 8, 10, 12, 14, or a sequence approximately at least 90% identical thereto, e.g., at least about 95%, about 96%, about 97%, about 98%, or about 99% identical thereto. In some embodiments, the antibody, or fragment thereof, comprises a heavy chain variable region that includes at least 50 contiguous amino acids of the amino acid sequence of any one of SEQ ID NOs: 4, 6, 8, 10, 12, 14, or a sequence approximately at least 90% identical thereto, e.g., at least about 100 or about 150 or about 200 or more contiguous amino acids.

In some embodiments, the antibody, or a fragment thereof, comprises a light chain variable region that includes the amino acid sequence of any one of SEQ ID NOs: 5, 7, 9, 11, 13, 15, or a sequence approximately at least 90% identical thereto, e.g., at least about 95%, about 96%, about 97%, about 98%, or about 99% identical thereto. In some embodiments, the antibody, or fragment thereof, comprises a light chain variable region that includes at least 50 contiguous amino acids of the amino acid sequence of any one of SEQ ID NOs: 5, 7, 9, 11, 13, 15, or a sequence approximately at least 90% identical thereto, e.g., at least about 100 or about 150 or about 200 or more contiguous amino acids.

In some embodiments, the antibody, or a fragment thereof, comprises a heavy chain variable region that includes the amino acid sequence of any one of SEQ ID NOs: 4, 6, 8, 10, 12, 14, or a sequence approximately at least 90% identical thereto, e.g., at least about 95%, about 96%, about 97%, about 98%, or about 99% identical thereto, and a light chain variable region that includes the amino acid sequence of any one of SEQ ID NOs: 5, 7, 9, 11, 13, 15, or a sequence approximately at least 90% identical thereto, e.g., at least about 95%, about 96%, about 97%, about 98%, or about 99% identical thereto. In some embodiments, the antibody, or fragment thereof, comprises a heavy chain variable region that includes at least 50 contiguous amino acids of the amino acid sequence of any one of SEQ ID NOs: 4, 6, 8, 10, 12, 14, or a sequence approximately at least 90% identical thereto, e.g., at least about 100 or about 150 or about 200 or more contiguous amino acids, and a light chain variable region that includes at least 50 contiguous amino acids of the amino acid sequence of SEQ ID NOs: 5, 7, 9, 11, 13, 15, or a sequence approximately at least 90% identical thereto, e.g., at least about 100 or about 150 or about 200 or more contiguous amino acids.

In some embodiments, the antibody, or a fragment thereof, comprises a heavy chain variable region that includes at least one CDR (e.g., 1, 2, or 3), or a portion thereof, from the amino acid sequence of SEQ ID NOs: 4, 6, 8, 10, 12, 14, or a sequence approximately at least 90% identical thereto, e.g., at least about 95%, about 96%, about 97%, about 98%, or about 99% identical thereto. One of skill in the art understands that the CDRs play a role in binding specificity and that sequence substitutions (e.g., for humanization of a mouse antibody) are typically made outside of the CDRs, and that minimal changes are typically made within the CDRs. Thus, in some embodiments, sequences that are approximately at least 90% identical to the disclosed sequences comprise no changes, or only a minimal number of changes, to the CDRs.

In some embodiments, the antibody, or a fragment thereof, comprises a light chain variable region that includes at least one CDR (e.g., 1, 2, or 3), or a portion thereof, from the amino acid sequence of SEQ ID NOs: 5, 7, 9, 11, 13, 15, or a sequence approximately at least 90% identical thereto, e.g., at least about 95%, about 96%, about 97%, about 98%, or about 99% identical thereto.

In some embodiments, the antibody, or a fragment thereof, comprises a heavy chain variable region that includes at least one CDR (e.g., 1, 2, or 3), or a portion thereof, from the amino acid sequence of SEQ ID NOs: 4, 6, 8, 10, 12, 14, or a sequence approximately at least 90% identical thereto, e.g., at least about 95%, about 96%, about 97%, about 98%, or about 99% identical thereto, and a light chain variable region that includes at least one CDR (e.g., 1, 2, or 3), or a portion thereof, from the amino acid sequence of SEQ ID NOs: 5, 7, 9, 11, 13, 15, or a sequence approximately at least 90% identical thereto, e.g., at least about 95%, about 96%, about 97%, about 98%, or about 99% identical thereto.

In further embodiments, the antibody can be a monoclonal antibody, or a fragment thereof, that competes for binding to the same epitope specifically bound by the monoclonal antibody ABC_G1D01 or ABC_G1D02 or ABC_G1D03 or ABC_G1D04 or ABC_G1D05 or ABC_G1D06. In still other embodiments, the antibody can be a monoclonal antibody, or a fragment thereof, that specifically binds to the same epitope specifically bound by the monoclonal antibody ABC_G1D01 or ABC_G1D02 or ABC_G1D03 or ABC_G1D04 or ABC_G1D05 or ABC_G1D06. In certain embodiments, the monoclonal antibody, or a fragment thereof, can be a chimeric antibody or a humanized antibody. In some embodiments, the chimeric or humanized antibody can include at least a portion of the CDRs of one of a monoclonal antibody ABC_G1D01 or ABC_G1D02 or ABC_G1D03 or ABC_G1D04 or ABC_G1D05 or ABC_G1D06.

Nucleic Acids, Cloning, and Expression Systems

The present disclosure further provides isolated nucleic acids encoding the disclosed antibodies. The nucleic acids may comprise DNA or RNA and may be wholly or partially synthetic or recombinant. Reference to a nucleotide sequence as set out herein encompasses a DNA molecule with the specified sequence, and encompasses a RNA molecule with the specified sequence in which U is substituted for T, unless context requires otherwise.

The nucleic acids provided herein can comprise a coding sequence for a CDR, a VH domain, and/or a VL domain disclosed herein. The present disclosure also provides constructs in the form of plasmids, vectors, phagemids, transcription or expression cassettes which can include at least one nucleic acid encoding a CDR, a VH domain, and/or a VL domain disclosed herein. The disclosure further provides a host cell that can include one or more constructs as above.

Also provided are nucleic acids encoding any CDR (H1, H2, H3, L1, L2, or L3), VH or VL domain, as well as methods of making the encoded products. The methods can include expressing the encoded product from the encoding nucleic acid. Expression may be achieved, for example, by culturing under appropriate conditions recombinant host cells containing the nucleic acid. Following production by expression a VH or VL domain, or specific binding member may be isolated and/or purified using any suitable technique, then used as appropriate and as understood by a person skilled in the art.

Antigen-binding fragments, VH and/or VL domains, and encoding nucleic acid molecules and vectors may be isolated and/or purified from their natural environment, in substantially pure or homogeneous form, or, in the case of nucleic acid, free or substantially free of nucleic acid or genes of origin other than the sequence encoding a polypeptide with the required function.

Systems for cloning and expression of a polypeptide in a variety of different host cells are well known in the art. For cells suitable for producing antibodies, see Gene Expression Systems, Academic Press, eds. Fernandez et al., 1999. Briefly, suitable host cells include bacteria, plant cells, mammalian cells, and yeast and baculovirus systems. Mammalian cell lines available in the art for expression of a heterologous polypeptide include Chinese hamster ovary cells, HeLa cells, baby hamster kidney cells, NS0 mouse myeloma cells, and many others. A common bacterial host is E. coli. Any protein expression system compatible with the present disclosure may be used to produce the disclosed antibodies. Suitable expression systems include transgenic animals described in Gene Expression Systems, Academic Press, eds. Fernandez et al., 1999.

Suitable vectors can be chosen or constructed so that they contain appropriate regulatory sequences, including promoter sequences, terminator sequences, polyadenylation sequences, enhancer sequences, marker genes, and other sequences as appropriate. Vectors may be plasmids or viral, e.g., phage, or phagemid, as appropriate. For further details see, for example, Sambrook et al., Molecular Cloning: A Laboratory Manual, $2^{nd}$ ed., Cold Spring Harbor Laboratory Press, 1989. Many known techniques and protocols for manipulation of nucleic acid, for example, in preparation of nucleic acid constructs, mutagenesis, sequencing, introduction of DNA into cells and gene expression, and analysis of proteins, are described in detail in Current Protocols in Molecular Biology, $2^{nd}$ Edition, eds. Ausubel et al., John Wiley & Sons, 1992.

Further aspects of the disclosure provide a host cell comprising a nucleic acid as disclosed herein, or otherwise derivable from the present disclosures. Still further aspects of the disclosure provide methods that include introducing such nucleic acid into a host cell. The introduction may employ any available technique. For eukaryotic cells, suitable techniques may include calcium phosphate transfection, DEAE-Dextran, electroporation, liposome-mediated transfection, and transduction using retrovirus or other virus, e.g., vaccinia or, for insect cells, baculovirus. For bacterial cells, suitable techniques may include calcium chloride transformation, electroporation, and transfection using bacteriophage. The introduction of the nucleic acid into the cells may be followed by causing or allowing expression from the nucleic acid, e.g., by culturing host cells under conditions for expression of the gene.

Pharmaceutical Compositions and Methods of Administration

The disclosure provides compositions comprising KLRG1 depletion agents, anti-KLRG1 antibodies, and/or fragments thereof, and/or conjugates and fusion proteins thereof. The compositions of the present disclosure can optionally comprise medicinal agents, pharmaceutical agents, carriers, pharmaceutically acceptable carriers, adjuvants, dispersing agents, diluents, and the like. Such compositions may be suitable for pharmaceutical use and administration to patients. By "pharmaceutically acceptable" it is meant a material that is not biologically or otherwise undesirable, i.e., the material can be administered to a subject without causing any undesirable biological effects such as toxicity. The compositions typically comprise one or more antibodies of the present disclosure and a pharmaceutically acceptable excipient. The phrase "pharmaceutically acceptable excipient" includes any and all solvents, dispersion media, coatings, antibacterial agents and antifungal agents, isotonic agents, and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions. The pharmaceutical compositions may also be included in a container, pack, or dispenser, together with instructions for administration.

The compositions of the present disclosure can be formulated for administration in a pharmaceutical carrier in accordance with known techniques. In the manufacture of a pharmaceutical formulation according to the present disclosure, the compound (including the physiologically acceptable salts thereof) can typically be admixed with, inter alia, an acceptable carrier. The carrier can be a solid or a liquid, or both, and can be formulated with the compound as a unit-dose formulation, for example, a tablet, which can contain from approximately 0.01% or approximately 0.5% to approximately 95% or approximately 99% by weight of the compound. One or more compounds can be incorporated in the formulations of the present disclosure, which can be prepared by any of the techniques of pharmacy known to those skilled in the art.

A pharmaceutical composition of the present disclosure can be formulated to be compatible with its intended route of administration. Methods to accomplish the administration are known to those skilled in the art. The administration may, for example, be intravenous, intraperitoneal, intramuscular, intracavity, subcutaneous, and/or transdermal. It may also be possible to obtain compositions that may be administered in other manners, including topically or orally, or which may be capable of transmission across mucous membranes.

Solutions or suspensions used for intradermal or subcutaneous application typically include one or more of the following components: a sterile diluent, such as water for injection, saline solution, fixed oils, polyethylene glycols, glycerin, propylene glycol, or other synthetic solvents; antibacterial agents, such as benzyl alcohol or methyl parabens; antioxidants, such as ascorbic acid, or sodium bisulfite; chelating agents, such as ethylenediaminetetraacetic acid; buffers, such as acetates, citrates, or phosphates; and agents for the adjustment of tonicity, such as sodium chloride or dextrose. The pH can be adjusted with acids or bases, such as hydrochloric acid or sodium hydroxide. Such preparations may be enclosed in ampoules, disposable syringes, or multiple dose vials, which can be made, for example, of glass or plastic.

Pharmaceutical compositions suitable for injection include sterile aqueous solutions or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.), or phosphate buffered saline (PBS). Typically, the composition should be sterile and should be fluid to the extent that easy syringeability exists. It should be stable under the conditions of manufacture and storage and should be preserved against the contaminating action of microorganisms, such as bacteria and fungi. Prevention of the action of microorganisms can be achieved, for example, by various antibacterial and antifungal agents, including parabens, chlorobutanol, phenol, ascorbic acid, thimerosal, and the like. In many cases, it will be preferable to include in the composition isotonic agents, for example, sugars and/or polyalcohols, such as mannitol, sorbitol, and sodium chloride. The carrier can be a solvent or dispersion medium containing, for example, water, ethanol, polyol (e.g., glycerol, propylene glycol, liquid polyetheylene glycol, and the like), and suitable mixtures thereof. The proper fluidity can be maintained, for example, by the use of a coating, such as lecithin, by the maintenance of the required particle size in the case of dispersion, and/or by the use of surfactants. Prolonged absorption of the injectable compositions can be brought about by including in the composition an agent that delays absorption, for example, aluminum monostearate, and gelatin.

Oral compositions generally include an inert diluent or an edible carrier. They can be enclosed in gelatin capsules or compressed into tablets in some instances. For oral administration, the antibodies can be combined with excipients and used in the form of tablets, troches, or capsules. Pharmaceutically compatible binding agents, and/or adjuvant materials, can be included as part of the composition. The tablets, pills, capsules, troches, and the like can contain any of the following ingredients, or compounds of a similar nature: a binder, such as microcrystalline cellulose, gum tragacanth, or gelatin; an excipient, such as starch or lactose; a disintegrating agent, such as alginic acid, Primogel, or corn starch; a lubricant, such as magnesium stearate or Sterotes; a glidant, such as colloidal silicon dioxide; a sweetening agent, such as sucrose or saccharin; or a flavoring agent, such as peppermint, methyl salicylate, or orange flavoring.

Systemic administration can also be by transmucosal or transdermal means. For transmucosal or transdermal administration, penetrants appropriate to the barrier to be permeated can be used in the formulation. Such penetrants are generally known in the art, and include, for example, detergents, bile salts, and fusidic acid derivatives. Transmucosal administration may be accomplished, for example, through the use of lozenges, nasal sprays, inhalers, or suppositories. For example, in case of antibodies that include the Fc portion, compositions may be capable of transmission across mucous membranes in intestine, mouth, or lungs (e.g., via the FcRn receptor-mediated pathway as described in U.S. Pat. No. 6,030,613). For transdermal administration, the active compounds may be formulated, for example, into ointments, salves, gels, or creams as generally known in the art. For administration by inhalation, the antibodies may be delivered, for example, in the form of an aerosol spray from pressured container or dispenser, which can contain a suitable propellant, e.g., a gas such as carbon dioxide, or a nebulizer.

In certain embodiments, the presently disclosed antibodies can be prepared with carriers that are configured to protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and/or polylactic acid. Methods for preparation of such formulations will be apparent to those skilled in the art. Liposomal suspensions containing the presently disclosed antibodies can also be used as pharmaceutically acceptable carriers. These can be prepared according to methods known to those skilled in the art, for example, as described in U.S. Pat. No. 4,522,811.

It may be advantageous to formulate oral or parenteral compositions in a dosage unit form for ease of administration and uniformity of dosage. The term "dosage unit form" as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of the composition of the present disclosure can be determined by standard pharmaceutical procedures in cell cultures or experimental animals, e.g., for determining the LD50 (the dose lethal to approximately 50% of the population) and the ED50 (the dose therapeutically effective in approximately 50% of the population). The dose ratio between toxic and therapeutic effects is the therapeutic index and it can be expressed as the ratio LD50/ED50. Compositions that exhibit large therapeutic indices are typically preferred.

For any composition used in the present disclosure, or derivable from the present disclosure, the therapeutically effective dose can be estimated initially from cell culture assays. Examples of suitable bioassays include but are not limited to DNA replication assays, cytokine release assays, transcription-based assays, KLRG1/cadherin binding assays, immunological assays, and other assays, such as those described in the Examples below. The data obtained from the cell culture assays and animal studies can be used in formulating a range of dosage for use in humans. A dose may be formulated in animal models to achieve a circulating plasma concentration range that includes the IC50 (i.e., the concentration of the antibody which achieves a half-maximal inhibition of symptoms). Circulating levels in plasma may be measured, for example, by high performance liquid chromatography. The effects of any particular dosage can be monitored by a suitable bioassay. The dosage lies preferably within a range of circulating concentrations with little or no toxicity. The dosage may vary depending, at least in part, upon the dosage form employed and the route of administration utilized. Alternatively, one can administer the presently disclosed antibodies, or those derivable from the present disclosure, in a local rather than systemic manner, for example, in a depot or sustained-release formulation.

A further aspect of the present disclosure relates to kits for use in the methods provided for herein or otherwise derivable in view of the present disclosures. A kit can comprise one or more antibodies of the present disclosure, and/or one or more antibodies derivable from the present disclosure, in a form suitable for administration to a subject, and/or in a form suitable for compounding into a formulation. The kit can further comprise other components, such as therapeutic agents, carriers, buffers, containers, devices for administration, and the like. The kit can be designed for therapeutic use, diagnostic use, and/or research use, and the additional components can be those suitable for the intended use. A person skilled in the art will recognize various such components suitable for inclusion in kits of this nature. The kit can further comprise labels and/or instructions, e.g., for treatment of a disorder. Such labeling and/or instructions can include, for example, information concerning the amount, frequency, and method of administration of the antibody. A person skilled in the art, in view of the present disclosures, will appreciate the types of instructions that may be included in conjunction as part of the kits. The instructions are provided for herein, or are otherwise derivable by a person skilled in the art in view of the present disclosures.

The following Working Examples do not in any way limit the scope of the present disclosure, and any invention(s) provided for herein. One of ordinary skill in the art will recognize the numerous modifications and variations that may be performed without altering the spirit or scope of the present disclosure. Such modifications and variations are encompassed within the scope of the present disclosure. The entire contents of all references, patents, and published patent applications cited throughout this application are herein incorporated by reference.

The phrase "disorder associated with KLGR1," as used herein, refers to any disease, disorder, or condition in which KLGR1 plays a role in a cause, side effect, symptom, or other aspect in the disease, disorder, or condition. Examples of such disorders include, without limitation, autoimmune and transplantation disorders, and cancer.

WORKING EXAMPLES

Example 1: Generation of Anti-KLRG1 Antibodies

Production of Recombinant Antigens and Proteins:

Recombinant proteins were produced by standard molecular cloning and expression protocols. The amino acid sequence of human KLRG1 ECD (SEQ ID NO:1), cyno KLRG1 ECD (SEQ ID NO:2) and human E-cadherin ECD (SEQ ID NO:3) are illustrated in Table 1.

TABLE 1

The amino acid sequence of human KLRG1 ECD (SEQ ID NO: 1), cyno KLRG1 ECD (SEQ ID NO: 2) and human E-cadherin ECD (SEQ ID NO: 3)

| | |
|---|---|
| human KLRG1 extracellular domain (ECD) (SEQ ID NO: 1), | LCQGSNYSTCASCPSCPDRWMKYGNHCYYFSVEEKDWNSSLEFCLARDSHLLVITDNQEM SLLQVFLSEAFCWIGLRNNSGWRWEDGSPLNFSRISSNSFVQTCGAINKNGLQASSCEVP LHWVCKKVRL |
| cyno KLRG1 extracellular domain (ECD) (SEQ ID NO: 2), | LCQGSKYSTCASCPSCPDHWMKYGNHCYYFSVEKKDWISSLEFCLARDSHLLMITDKQEM SLLQDFLSEAFHWVGLRNNSGWRWEDGSPLNFSRIYSNSLVQTCGAINKNSLQASSCEVS LQWVCKKVSP |
| human E-cadherin full length (SEQ ID NO: 3) | DWVIPPISCPENEKGPFPKNLVQIKSNKDKEGKVFYSITGQGADTPPVGVFIIERETGWL KVTEPLDRERIATYTLFSHAVSSNGNAVEDPMEILITVTDQNDNKPEFTQEVFKGSVMEG ALPGTSVMEVTATDADDDVNTYNAAIAYTILSQDPELPDKNMFTINRNTGVISVVTTGLD RESFPTYTLVVQAADLQGEGLSTTATAVITVTDTNDNPPIFNPTTYKGQVPENEANVVIT TLKVTDADAPNTPAWEAVYTILNDDGGQFVVTTNPVNNDGILKTAKGLDFEAKQQYILHV AVTNVVPFEVSLTTSTATVTVDVLDVNEAPIFVPPEKRVEVSEDFGVGQEITSYTAQEPD TFMEQKITYRIWRDTANWLEINPDTGAISTRAELDREDFEHVKNSTYTALIIATDNGSPV ATGTGTLLLILSDVNDNAPIPEPRTIFFCERNPKPQVINIIDADLPPNTSPFTAELTHGA SANWTIQYNDPTQESIILKPKMALEVGDYKINLKLMDNQNKDQVTTLEVSVCDCEGAAGV CRKAQPVEAGLQIPAILGILGGILALLILILLLLFLRRRAVVKEPLLPPEDDTRDNVYY YDEEGGGEEDQDFDLSQLHRGLDARPEVTRNDVAPTLMSVPRYLPRPANPDEIGNFIDEN LKAADTDPTAPPYDSLLVFDYEGSGSEAASLSSLNSSESDKDQDYDYLNEWGNRFKKLAD MYGGGEDD |

Recombinant proteins were produced as FC fusion or as HIS tagged versions by cloning the respective cDNA into pCDNA4 vector (Invitrogen) and transient transfection in mammalian HEK293 cells. Purification of the expressed proteins took place by chromatography using Protein A affinity resin for the FC fusion versions and Nickel-NTA resin for HIS tagged proteins. All purified proteins were characterized by SDS-PAGE electrophoresis to verify purity and molecular weight.

Stable cell lines were developed to be used as immunization antigens, to test binding of antibodies to full length antigen and as target cells in functional T cell assays. Cell lines developed include CHO cells expressing full length human KLRG1 and CHO cells expressing full length cynomolgus KLRG1. Stable cell lines were derived by transfection of CHO cells with pCDNA4 plasmid coding protein of interest. After transfection, the cells were exposed to approximately 500 ug/ml of G418 to select for stably integrated plasmid. The cell lines were further characterized by FACS for expression and were sorted to select for homogeneous and stable expression.

Monoclonal antibodies (MAB) against human KLRG1 were generated by standard immunizations of female BALB/c mice and SJL mice with human and cynomolgus KLRG1, and subsequent hybridoma screening. Several immunization strategies were employed to generate a diverse number of antibody hits. Briefly SJL and Balb/c mice were repeatedly immunized with either cDNA encoding the antigen of interest, recombinant antigen, or CHO cells expressing the antigen of interest. Antigen specific antibody titers were periodically monitored by ELISA and animals were sacrificed when appropriate titers were reached, usually between approximately 1:1000 and approximately 1:10000 dilution factor. Splenocytes from sacrificed mice were fused to mouse myeloma cells to produce hybridoma cells and later cultured and sub-cloned into single cells. Stable clones were scaled up and condition media was harvested and tested for expression of anti-KLRG1 antibodies by ELISA and FACS.

Example 2: Selection of Anti-KLRG1 Antibodies

Hybridoma produced antibodies were screened for binding to human KLRG1 ECD and cyno KRG1 ECD. Antibodies with cross reactivity between both antigens were chosen to move forward to the next stage of screening to determine their ability to block the interaction between KLRG1 and E-cadherin. Antibodies were ranked according to their binding EC50 to human and cyno KLRG1 and further selected as hits if they did not interfere with E-cadherin binding in a competition assay. A total of 35 antibodies were selected according to these criteria and six (6) antibodies were prioritized for functional characterization in cell-based assay.

Provided below is sequence information for the six selected antibodies that bind to human KLRG1: ABC_G1D01, ABC_G1D02, ABC_G1D03, ABC_G1D04, ABC_G1D05 and ABC_G1D06.

Table 2 summarizes the amino acid sequences of the heavy and light chain variable regions of the six selected mouse antibodies that bind to human KLRG1, and Table 3 shows the CDR regions for each antibody.

TABLE 2

Amino acid sequences of the heavy and light chain variable regions for each mouse anti-KLRG1 antibody

| | |
|---|---|
| ABC_G1D01-VH | EVQLQQSGPELVKPGASVKMSCKASGYTFTDYNIHWVKQSHGKSLEWIGFFNPKNG VTINNQNFKGKAALTVNKSSTAYMELRRLTSEDSAVYYCARDYYGTAWFAYWGQG TLVTVSA (SEQ ID NO: 4) |
| ABC_G1D01-VK | DIVMSQSPSSLAVSVGEKVTMSCRSSQSLLYSSNQKNYLAWYQQKPGQSPKLLIYW ASTRESGVPDRFTGSGSGTDFTLTISSVKAEDLAVYYCQQFYSYPTFGGGTKLEIK (SEQ ID NO: 5) |
| ABC_G1D02-VH | QVQLQQSGAELVRPGTSVKVSCKASGYAFTNYFIEWIKQRPGQGLEWIGVINPGSG GTNYNEKFKGKATLTADKSSSTAYMQLSSLTSEDSAVYFCTRPGHFDYWGQGTTLT VSS (SEQ ID NO: 6) |
| ABC_G1D02-VK | EIVLTQSPTTMAASPGEKITITCSASSSISSNYLHWYQQKPGFSPKLLIYKTSNLA SGVPPRFSGSGSGTSYSLTIGTMEAEDVATYYCQQGNSIPRTFGGGTKLEIK (SEQ ID NO: 7) |
| ABC_G1D03-VH | EVQLQQSGPELVKPGASVKMSCKTSGYTFTDHNMHWLKQSHGKGLEWFGFINPNTG VTRYNQKFNGKATLTINKSSSTAYLDLRSLTSEDSAVYYCTRDYYGSAWFAYWGQG TLVTVSA (SEQ ID NO: 8) |
| ABC_G1D03-VK | DIVMSQSPASQTVSVGEKVTMSCKSSQTLLYSSDQKNYLAWYQQKPGQSPKLLIYW ASTRESGVPDRFTGSGSGTDFTLTISSVKAEDLAVYYCQQYYNYPTFGGGTKLEIK (SEQ ID NO: 9) |
| ABC_G1D04-VH | EVQLQQSGPELVKPGSSLMMSCKSSGYTFTDYNIHWVKQSHGKRLEWIGFIDPKNG GTLYSEKFKDKATLTINKSSSTAYMELRSLTSEDSAVFYCAPDYYGSAWFAYWGQG TLVTVSA (SEQ ID NO: 10) |
| ABC_G1D04-VK | DIVMSQSPSSLTVSVGENVTMSCKSSQNLLYTSNQKNYLAWYQQKPGHSPKLLISW ASTRESGVPDRFTGSGSGTDFTLTITSVKAEDLAVFYCQQYYHYPTFGGGTKLEIK (SEQ ID NO: 11) |
| ABC_G1D05-VH | QVQLKQSGPGLVQPSQSLSITCTVSGFSLTTHGVHWVRQSPGKGLEWLGVIWSGGS TDYNAAFISRLSIRKDNSKSQVFFKMNSLQTNDTAIYYCARLRLPAMDYWGQGTSV TVSS (SEQ ID NO: 12) |
| ABC_G1D05-VK | QIVLTQSPTIMSASLGERVTMTCTASSSVSSTYLHWYQQKPGSSPKLWIYSTSNLA SGVPARFSGSGSGTSYSLTISSMEAEDAATYYCHQYHRSPLSFGAGTKLELK (SEQ ID NO: 13) |
| ABC_G1D06-VH | QVQLQQSGAELVRPGASVTLSCKASGYKFSDYEIHWVKQTPVYGLEWIGALEPATG GTAYNPNFKGKAILTADKSSTTAYMELRSLTSEDSAVYYCSMHLAVYWGQGTLVTV SA (SEQ ID NO: 14) |

TABLE 2 -continued

Amino acid sequences of the heavy and light chain variable regions for each mouse anti-KLRG1 antibody ABC_G1D06-VK  DVVMTQTPLTLSVTFGQPASISCKSSQSLLYSNGKTYLNWLLQRPGQSPKRLIYLV
SKLDSGVPDRFTGSGSGTDFTLKISRVEAEDLGVYYCVQGTHSPRTFGGGTKLEIK
(SEQ ID NO: 15)

TABLE 3

CDR sequences for selected antibodies:

| | CDR-H1 | CDR-H2 | CDR-H3 | CDR-L1 | CDR-l2 | CDR-l3 |
|---|---|---|---|---|---|---|
| ABC_G1D01 | GYTFTDY (SEQ ID NO: 16) | NPKNGV (SEQ ID NO: 17) | DYYGTAWFAYRSSQSLLYSSNQKNYLA (SEQ ID NO: 18) | (SEQ ID NO: 19) | WASTRES (SEQ ID NO: 20) | QQFSYPT (SEQ ID NO: 21) |
| ABC_G1D02 | GYAFTNY (SEQ ID NO: 22) | NPGSGG (SEQ ID NO: 23) | PGHFDY (SEQ ID NO: 24) | SASSSISSNYLH (SEQ ID NO: 25) | KTSNLAS (SEQ ID NO: 26) | QQGNSIPRT (SEQ ID NO: 27) |
| ABC_G1D03 | GYTFTDH (SEQ ID NO: 28) | NPNTGV (SEQ ID NO: 29) | DYYGSAWFAYKSSQTLLYSSDQKNYLA (SEQ ID NO: 30) | (SEQ ID NO: 31) | WASTRES (SEQ ID NO: 32) | QQYYNYPT (SEQ ID NO: 33) |
| ABC_G1D04 | GYTFTDY (SEQ ID NO: 34) | DPKNGG (SEQ ID NO: 35) | DYYGSAWFAYKSSQNLLYTSNQKNYLA (SEQ ID NO: 36) | (SEQ ID NO: 37) | WASTRES (SEQ ID NO: 38) | QQYYHYPT (SEQ ID NO: 39) |
| ABC_G1D05 | GFSLTTH (SEQ ID NO: 40) | IWSGGS (SEQ ID NO: 41) | LRLPAMDY (SEQ ID NO: 42) | TASSSVSSTYLH (SEQ ID NO: 43) | STSNLAS (SEQ ID NO: 44) | HQYHRSPLS (SEQ ID NO: 45) |
| ABC_G1D06 | GYKFSDY (SEQ ID NO: 46) | LEPATGG (SEQ ID NO: 47) | HLAVY (SEQ ID NO: 48) | (SEQKSSQSLLYSNGKTYLN (SEQ ID NO: 49) | LVSKLDSG (SEQ ID NO: 50) | VQGTHSPRT (SEQ ID NO: 51) |

The antibodies were further ranked according to the presence of sequence liabilities motifs and are summarized in Table 4.

TABLE 4

Sequence liability motifs used to screen antibodies for potential manufacturability problems:

| Liability | Motif | Consequence |
|---|---|---|
| Unpaired cysteine | C | Adduct formation, activity loss, scrambling, aggregation, process inconsistency |
| Deamidation | NG | Activity loss, aggregation, process inconsistency |
| N-glycosylation | NXS/T, X not P | Impact on PK if heavily sialylated, activity loss |
| Tyrosine sulphation | Neg-Neg-Y-Neg-Neg | Activity loss, process inconsistency |
| Hydrolysis | DP | Fragmentation, stability |
| Asp-Pro | | |
| Methionine oxidation | M | Activity loss, aggregation |
| Tryptophan oxidation | W | Photosensitivity, activity loss |
| Deamidation | NS, UG, NN | Activity loss, aggregation, process inconsistency |
| Asparatate isomerisation | DG, DS, DQ, DK | Activity loss, aggregation |

Table 5 shows examples of humanized constructs for ABC_HG1D02 and ABC_HG1D03. Humanization was carried out by grafting the CDR of the mouse antibodies onto human framework sequences with the highest sequence homology.

TABLE 5

Amino acid sequences of variable regions for selected antibodies after humanization:

ABC_HG1D02-VH  QVQLVQSGAEVKKPGSSVKVSCKASGYAFTNYFIEW
VRQRPGQGLEWMGVINPGSGGTNYNEKFKGRVTITA
DKSSSTAYMELSSLRSEDTAVYYCARPGHFDYWGQG
TTVTVSS (SEQ ID NO: 52)

ABC_HG1D02-VK  EIVLTQSPTTLSLSPGERATLSCSASSSISSNYLHW
YQQKPGFAPRLLIYKTSNLASGIPPRFSGSGSGTDF
TLTISRLEPEDFAVYYCQQGNSIPRTFGQGTKVEIK
RTV (SEQ ID NO: 53)

ABC_HG1D03-VH  EVQLVQSGAEVKKPGASVKVSCKASGYTFTDHNMHW
VKQATGQGLEWFGFINPNTGVTRYNQKFQGRVTLTI
NKAISTAYLELSSLRSEDTAVYYCARDYYGSAWFAY
WGQGTLVTVSS (SEQ ID NO: 54)

ABC_HG1D03-VK  DIVMTQSPDSLAVSLGERATINCKSSQTLLYSSDQK
NYLAWYQQKPGQPPKLLIYWASTRESGVPDRFSGSG
SGTDFTLTISSLQAEDVAVYYCQQYYNYPTFGGGTK
V (SEQ ID NO: 55)

Back mutations can be introduced in humanized constructs to improve affinity. Furthermore, conservative mutations can be made to the CDR regions to improve affinity, potency, or biophysical characteristics.

Table 6 summarizes a list a conservative mutation that can be made to the CDR regions.

TABLE 6

| Residue | Conservative substitution | Residue | Conservative Substitution |
|---|---|---|---|
| Ala (A) | Ser (S) | Leu (L) | Ile (I), Val (V) |
| Arg (R) | Lys (K) | Lys (K) | Arg (R), Gln (Q) |
| Asn (N) | Gln (Q); His (H) | Met (M) | Leu (L), Ile (I) |
| Asp (D) | Glu (E) | Phe (F) | Met (M), Leu (L), Tyr (Y) |
| Cys (C) | Ser (S) | Ser (S) | Thr (T); Gly (G) |
| Gln (Q) | Asn (N) | Thr (T) | Ser (S), Val (V) |
| Glu (E) | Asp (D) | Trp (W) | Tyr (Y) |
| Gly (G) | Pro (P) | Tyr (Y) | Trp (W), Phe (F) |
| His (H) | Asn (N), Gln (Q) | Val (V) | Ile (I), Leu (L) |
| Ile (I) | Leu (L), Val (V) | Pro (P) | — |

The antibodies were produced as chimeric by cloning the variable mouse regions onto human IgG constant frameworks and tested in functional assays to determine their functional activity on human T cells and described herein.

Example 3: Characterization of Antibody Binding Site by Epitope Mapping

The monoclonal antibodies were found to all bind to the same epitope when binned according to their ability to compete with each other. The binding site of ABC-G1D03 was further analyzed by peptide mapping to identify the specific binding epitope and it was found that it bound to a peptide with the following amino acid sequence: "PLNFSRI" (SEQ ID NO:56). The mapping is illustrated in FIG. 1.

Figure 2:
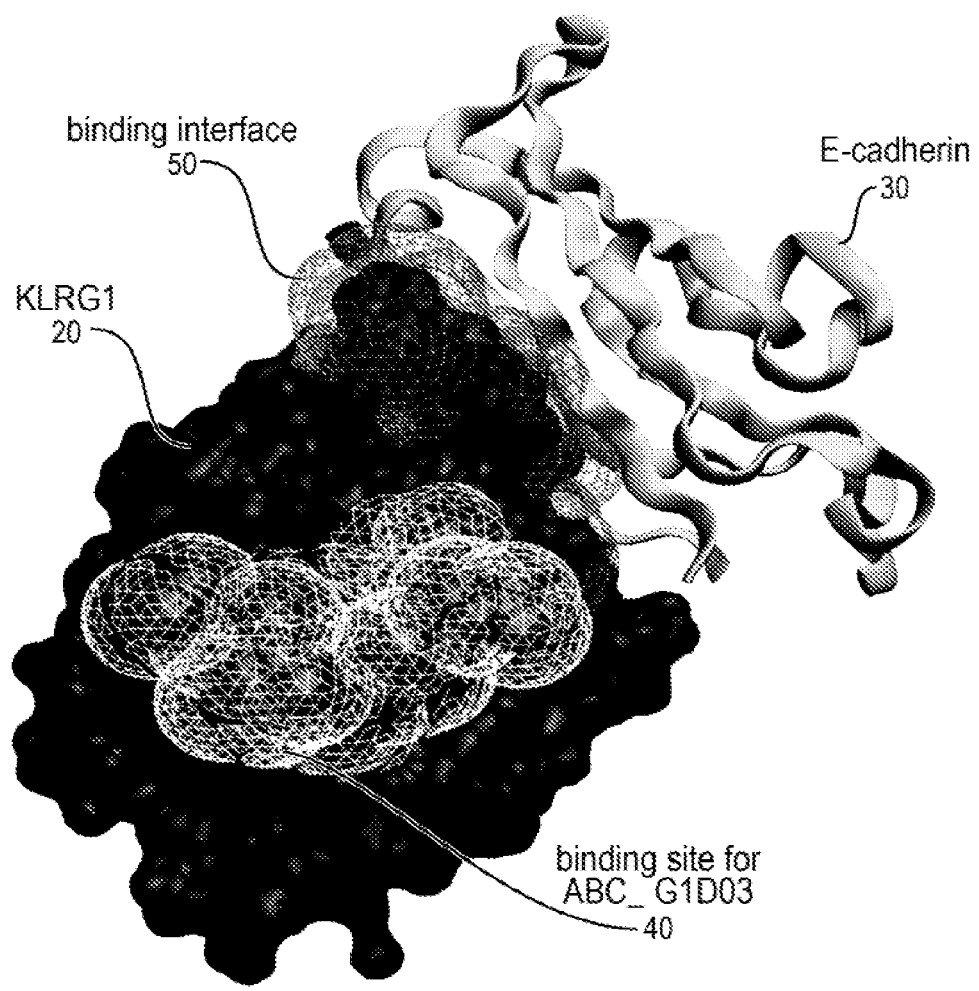
FIG. 2 provides a three-dimensional representation of KLRG1 (20) binding to E-cadherin (3) derived from the PDB crystal structure 3ff7, with a first highlighted region (40) corresponding to a binding site for ABC_G1D03 defined by amino acids "PLNFSRI" (SEQ ID NO: 56), on KLRG1, and a second highlighted region (50) corresponding to a binding interface between KLRG1 and E-cadherin.

This sequence can be mapped onto a three-dimensional crystal structure of KLRG1 deposited in the Protein Data Bank (www.rcsb.org/structure/3FF7) to reveal the binding site. FIG. 2 summarizes the epitope mapping results and highlights that the antibody binding site is distinct from the known ligand binding site. Specifically, FIG. 2 illustrates the three-dimensional representation of KLRG1 (20) binding to E-cadherin (30) derived from the PDB crystal structure 3ff7. A distinct region (40) of KLRG1 highlighted in FIG. 2 corresponds to the binding site for ABC_G1D03 defined by amino acids "PLNFSRI" (SEQ ID NO:56) on KLRG1. A second region (50) highlighted in FIG. 2 corresponds to the binding interface between KLRG1 and E-cadherin.

Example 4: Measurement of Antibody Binding to Cell Expressed KLRG1 by FACS

Binding of anti-KLRG1 monoclonal antibodies to cells that expressed human and cynomolgus-KLRG1 was carried out by FACS. Chinese hamster ovary (CHO) cells were stably transfected to express full length human KLRG1 (CHO-human-KLRG1) and cynomolgus KLRG1 (CHO-cynomolgus-KLRG1). EC50 values were determined by incubation of varying concentrations of anti-KLRG1 monoclonal antibodies at concentrations ranging from approximately 1 nM to approximately 100 nM, and measuring fluorescence of the labeled cells using an anti-mouse detection antibody directly conjugated with a fluorescent probe. Table 7 summarizes the EC50 binding data measured for selected antibodies.

TABLE 7

Binding EC50 of MABs measured by FACS:

| | FACS Binding EC50 (nM) | |
|---|---|---|
| Antibody | Human EC50 | Cyno EC50 |
| ABC_G1D01 | 4.87 | 3.44 |
| ABC_G1D02 | 9.11 | 10.1 |
| ABC_G1D03 | 6.3 | 8.63 |
| ABC_G1D04 | 212.9 | 7.2 |
| ABC_G1D05 | 5.15 | 5.93 |
| ABC_G1D06 | 72.5 | 3.4 |

Example 5: Measurement of Binding Kinetics

Binding kinetics of humanized antibodies for human and cynomolgus KLRG1 were determined by Octet® Systems (ForteBio) measurement. The Octet® platform includes instruments, biosensors, reagents, and assay kits for analysis of biomolecular interactions in 96- and 384-well microplates for use in real-time, label-free analysis for determination of affinity, kinetics, and concentration. The experimental set-up includes immobilizing biotinylated recombinant antigen (Human-KLRG-ECD or cynomolgus-KLRG1-ECD) on a streptavidin Octet® sensor to produce antigen loaded sensors. The loaded sensors can then be exposed to varying concentrations of each humanized antibody from approximately 100 nM to approximately 0.1 nM in the OCET® instruments and data collected for approximately 600 seconds to measure association kinetic (Kon) of the antibody/antigen complex. Thereafter, the sensors can be exposed to a solution of 1× phosphate buffered saline (PBS) buffer devoid of antibody for approximately 600 seconds to observe dissociation kinetics (kdis). The resulting data can then be fitted to a 1:1 binding kinetics model using, for example, ForteBio analysis software to calculate the KD. Kinetic binding parameters derived by this method are summarized in Table 8 for three humanized antibodies.

TABLE 8

Binding affinity of selected MABs measured by OCTET:

| Antigen | Antibody | kon (1/Ms) | kdis (1/s) | KD (M) |
|---|---|---|---|---|
| Human KLRG1 | ABC_HG1D02 | 5.41E+5 | 3.07E−5 | 5.67E−11 |
| | ABC_HG1D03 | 3.80E+5 | 5.91E−5 | 1.56E−10 |
| | ABC_HG1D04 | 5.05E+5 | 1.25E−4 | 2.48E−10 |
| Cyno KLRG1 | ABC_HG1D02 | 3.67E+5 | 1.42E−4 | 3.88E−10 |
| | ABC_HG1D03 | 6.27E+5 | 3.82E−5 | 6.09E−11 |
| | ABC_HG1D04 | 5.85E+5 | 4.74E−5 | 8.10E−11 |

Example 6: Characterization of ADCC Activity for KLRG1 Binding Antibodies

This example demonstrates that non-blocking antibodies against KLRG1 have no effect on T cell activity and therefore are functionally different from blocking antibodies, which interfere with the interaction between KLRG1 and its ligands and result in activating effect on human CD8+ T cell by measured by production of interferon gamma (IFN-gamma).

Here KLRG1 blocking antibodies are defined as binding to KLRG1 extracellular domain and effectively competing with E-cadherin, N-cadherin, or R-cadherin binding to KLRG1. Conversely, non-blocking antibodies are defined as antibodies that bind to KLRG1 extracellular domain but do not compete with E-cadherin, N-cadherin, or R-cadherin binding to KLRG1.

Figure 3:
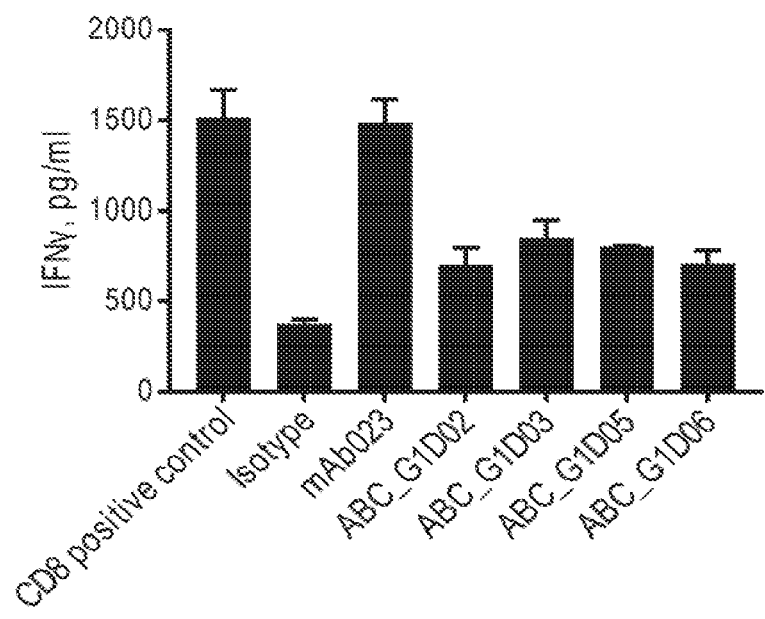
FIG. 3 provides a table and resulting graph that illustrates activity of non-blocking KLRG1 blocking antibodies on CD8+ human T cells; in contrast with KLRG1 blocking antibodies (mAb23), non-blocking antibodies have low activity in stimulating interferon gamma release in human CD8 T cells.

To demonstrate the differential functional effect of KLRG1 blockade on cells of the immune system, CD8+ T cells were isolated from healthy donors and tested in co-culture with a CHO cell line co-expressing a CD3 agonist and an E-cadherin (eAPC). The assay works by providing T cells with two (2) competing signals where CD3 stimulation is counteracted by the inhibitory effect of E-cadherin. When KLRG1 signaling is blocked by anti-KLRG1 antibodies, the inhibitory signal is disrupted, and T cells are activated according to their interaction with the CD3 agonist expressed on the cell surface. Interferon gamma secretion is measured by ELISA and results summarized in FIG. 3. This data demonstrate that E-cadherin has an inhibiting effect on human T cells which can be reversed by blockade of KLRG1 signaling with blocking antibodies. It also shows that non-blocking antibodies do not have stimulating effect.

Example 7: Selective In Vivo Depletion of KLRG1 Positive T Cells with Non-Blocking Anti-KLRG1 Antibody in Non-Human Primate This example demonstrates that non-blocking anti-KLRG1 antibodies can be used to selectively deplete KLRG1 positive T cells while sparing other lymphocytes necessary for normal immune function, such as regulatory T cells and naïve T cells. In the present example, the antibody ABC-HG1D03 was produced in an afucosylated form and administered to cynomolgus monkeys via a subcutaneous route of administration.

TABLE 9 summarizes the study design, including number of animals per cohort, dosing amount, and dosing regimen:

| Group | Test Material | Dose level (mg/kg/day) | Doses (Days) | Main study (28 days) Male | Main study (28 days) Female |
|---|---|---|---|---|---|
| 1 | Control | 0 | 1, 8, 15, 22 | 5 | 5 |
| 2 | ABC-HG1D03 | 0.1 | 1, 8 | 3 | 3 |
| 3 | ABC-HG1D03 | 0.3 | 1, 8 | 3 | 3 |
| 4 | ABC-HG1D03 | 10 | 1, 8, 15, 22 | 3 | 3 |
| 5 | ABC-HG1D03 | 30 | 1, 8, 15, 22 | 5 | 5 |

In order to monitor the effect of afucosylated ABC-HG1D03 on different immune cells, flow cytometry was used to immunophenotype circulating lymphocytes in cynomolgus monkey whole blood.

Figure 4:
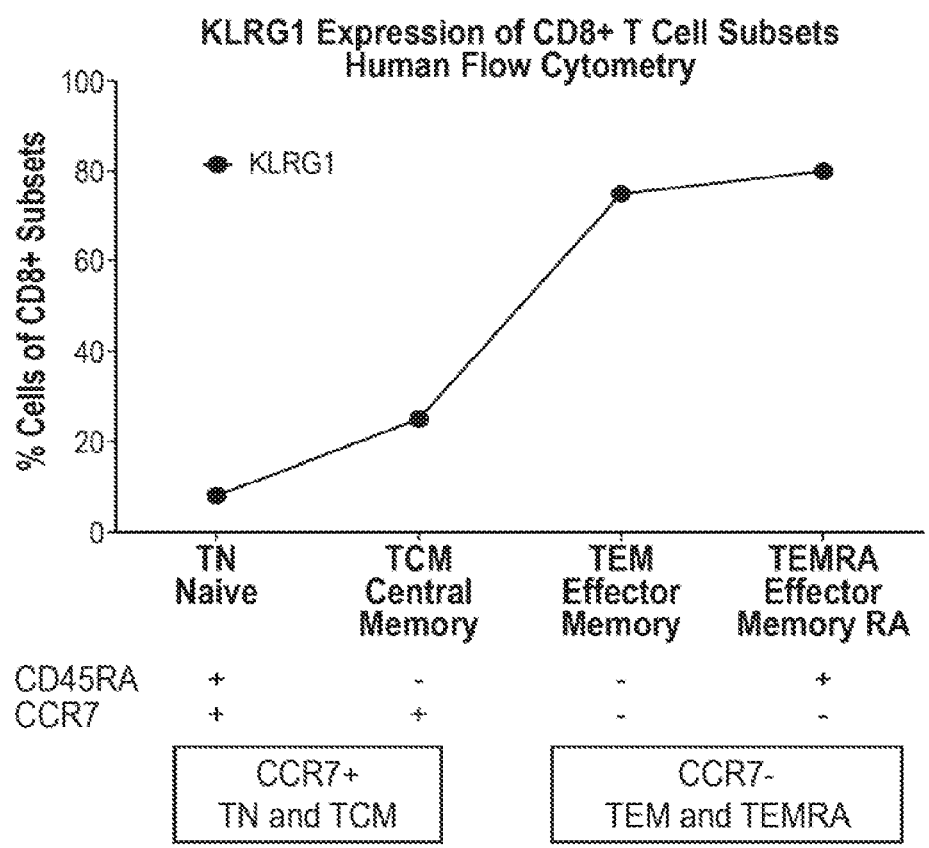
FIG. 4 provides a graph illustrating KLRG1 expression on T cell subsets, with KLRG1 being differentially expressed on effector T cells (TEM and TEMRA), which are CCR7−, compared to naive T cells (TN and TCM), which are CCR7+.

FIG. 4 highlights the identification scheme for KLRG1 positive cells and the classification of T cells as naïve (CCR7+) or effector (CCR7−). As established in published data (Koch et al., 2008, Legat et al., 2013), the flow cytometry data of FIG. 4 shows that KLRG1 is expressed predominantly on a subset of CCR7− effector T cells. The flow cytometry data of FIG. 4 also shows that KLRG1 is differentially expressed on effector T cells (TEM and TEMRA), which are CCR7−, compared to naive T cells (TN and TCM), which are CCR7+. One skilled in the art will recognize that central memory T cells (TCM) express CCR7 while effector memory (TEM) T cells lack expression of CCR7. In humans, but not in mice, there is a third T cell memory subset, TEMRA, that includes cells that express CD45RA but lack expression of CCR7.[2]

[2] (Willinger, T. et al. Molecular Signatures Distinguish Human Central Memory from Effector Memory CD8 T Cell Subsets. J Immunol 2005; 175:5895-5903; doi: 10.4049/jimmunol. 175.9.5895 www.jimmunol.org/content/175/9/5895

Figure 5:
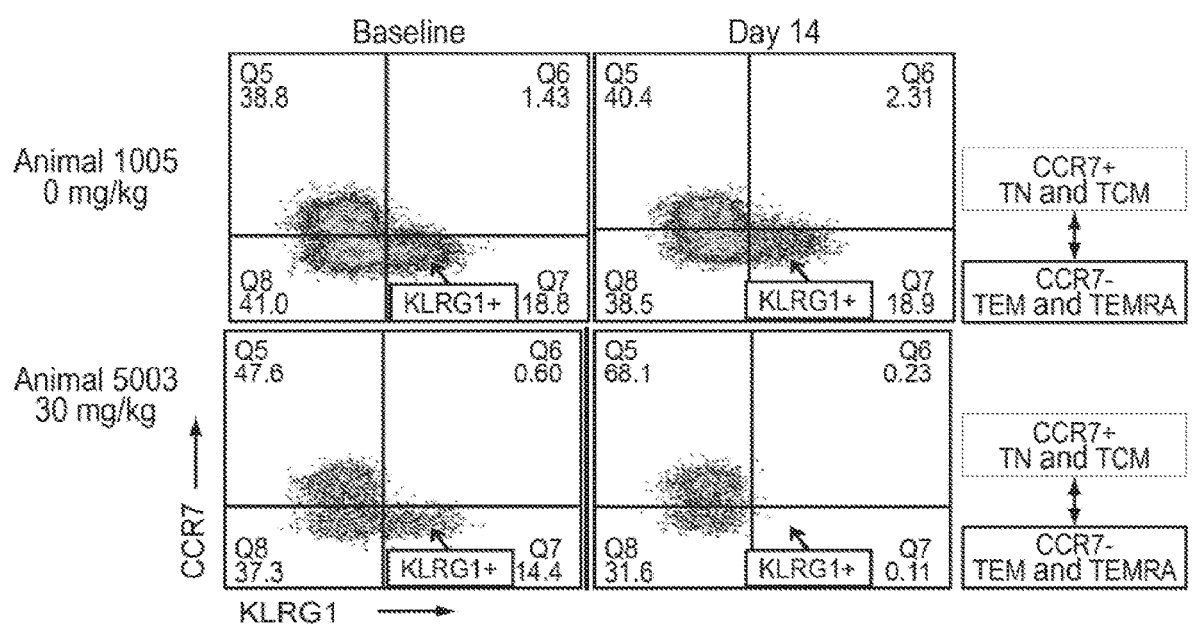
FIG. 5 provides flow cytometry analysis of CD8 T cells from non-human primate whole blood, highlighting the depletion effect of ABC-HG1D03 on KLRG1+ T cells; of note is that KLRG1 positive cells correspond to the effector phenotype and ABC-HG1D03 results in full, yet selective, depletion of this compartment.

The flow cytometry data of FIG. 5 exemplifies the depletion effect of in vivo administration of ABC-HG1D03 to cynomolgus monkeys by comparing a control animal with an animal dosed at 30 mg/kg. This data shows the depletion of KLRG1+ cells in the ABC-HG1D03 dosed animal compared to control, demonstrating the selective depletion of effector T cells and not naïve T cells. The flow cytometry analysis of CD8 T cells from non-human primate whole blood highlights the depletion effect of ABC-HG1D03 on KLRG1+ T cells. Notably, the KLRG1 positive cells correspond to the effector phenotype and contact with ABC-HG1D03 results in full, yet selective depletion of this compartment.

Figure 6:
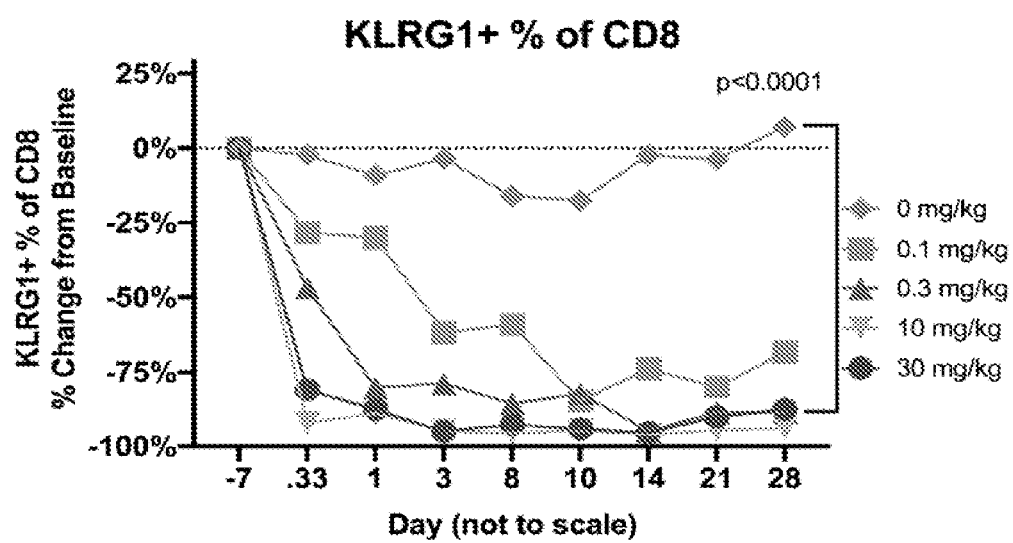
FIG. 6 provides a graph illustrating a dose dependent effect of ABC-HG1D03 on % KLRG1+CD8 T cells in a non-human primate.

The average % of KLRG1+CD8 T cells in all dosed animals are plotted in FIG. 6. As shown, there is a dose dependent effect of ABC-HG1D03 on depletion of KLRG1+ CD8 T cells.

In some embodiments, there can be a regulatory T cell sparing effect from the administration of ABC-HG1D03 to cynomolgus monkeys. The data shows no effect over a period of 28 days of KLRG1 depleting treatment on regulatory T cells for the dosing groups tested. Tregs can be viewed as another subset of activated T cells whose role is to regulate and suppress, rather than to induce and promote, immune responses. Tregs express Foxp3, and a subset of which express KLRG1.

One skilled in the art will appreciate further features and advantages of the disclosure based on the above-described embodiments. Accordingly, the disclosure is not to be limited by what has been particularly shown and described, except as indicated by the appended claims. All publications and references cited herein are expressly incorporated herein by reference in their entirety. Citation of references is not an admission that these references are prior art to the present disclosure.

REFERENCES

1. Akbar A N, Henson S M. Are senescence and exhaustion intertwined or unrelated processes that compromise immunity? Nat Rev Immunol. 2011; 11 (4): 289-95.
2. Amemiya K, Granger R P, Dalakas M C. Clonal restriction of T-cell receptor expression by infiltrating lymphocytes in inclusion body myositis persists over time. Studies in repeated muscle biopsies. Brain: a journal of neurology. 2000; 123 (Pt 10): 2030-9.
3. Apetoh L, Smyth M J, Drake C G, Abastado J P, Apte R N, Ayyoub M, et al. Consensus nomenclature for CD8 T cell phenotypes in cancer. Oncoimmunology. 2015; 4 (4): e998538.
4. Arahata K, Engel A G. Monoclonal antibody analysis of mononuclear cells in myopathies. I: Quantitation of subsets according to diagnosis and sites of accumulation and demonstration and counts of muscle fibers invaded by T cells. Ann Neurol. 1984; 16 (2): 193-208.
5. Arahata K, Engel A G. Monoclonal antibody analysis of mononuclear cells in myopathies. Ill: Immunoelectron microscopy aspects of cell-mediated muscle fiber injury. Ann Neurol. 1986; 19 (2): 112-25.
6. Arahata K, Engel A G. Monoclonal antibody analysis of mononuclear cells in myopathies. IV: Cell-mediated cytotoxicity and muscle fiber necrosis. Ann Neurol. 1988; 23 (2): 168-73.

7. Attig S, Hennenlotter J, Pawelec G, Klein G, Koch S D, Pircher H, et al. Simultaneous infiltration of polyfunctional effector and suppressor T cells into renal cell carcinomas. Cancer Res. 2009; 69 (21): 8412-9.
8. Betjes M G, Meijers R W, de Wit E A, Weimar W, Litjens N H. Terminally differentiated CD8+ Temra cells are associated with the risk for acute kidney allograft rejection. Transplantation. 2012; 94 (1): 63-9.
9. Bisping G, Lugering N, Lutke-Brintrup S, Pauels H G, Schurmann G, Domschke W, et al. Patients with inflammatory bowel disease (IBD) reveal increased induction capacity of intracellular interferon-gamma (IFN-gamma) in peripheral CD8+ lymphocytes co-cultured with intestinal epithelial cells. Clinical and experimental immunology. 2001; 123 (1): 15-22.
10. Blanco P, Viallard J F, Pellegrin J L, Moreau J F. Cytotoxic T lymphocytes and autoimmunity. Current opinion in rheumatology. 2005; 17 (6): 731-4.
11. Brunner S M, Rubner C, Kesselring R, Martin M, Griesshammer E, Ruemmele P, et al. Tumor-infiltrating, interleukin-33-producing effector-memory CD8 (+) T cells in resected hepatocellular carcinoma prolong patient survival. Hepatology. 2015; 61 (6): 1957-67.
12. Bueno V, Pestana J O. The role of CD8+ T cells during allograft rejection. Brazilian journal of medical and biological research=Revista brasileira de pesquisas medicas e biologicas/Sociedade Brasileira de Biofisica [et al]. 2002; 35 (11): 1247-58.
13. Carvalheiro H, Duarte C, Silva-Cardoso S, daSilva J A, Souto-Carneiro M M. CD8 T cell profiles in patients with rheumatoid arthritis and their relationship to disease activity. Arthritis & rheumatology. 2014; 37 (2): 363-71.
14. D'Asaro M, Dieli F, Caccamo N, Musso M, Porretto F, Salerno A. Increase of CCR7-CD45RA+ CD8 T cells (T (EMRA)) in chronic graft-versus-host disease. Leukemia. 2006; 20 (3): 545-7.
15. Faustman D L, Davis M. The primacy of CD8 T lymphocytes in type 1 diabetes and implications for therapies. Journal of molecular medicine. 2009; 87 (12): 1173-8.
16. Friese M A, Fugger L. Pathogenic CD8 (+) T cells in multiple sclerosis. Ann Neurol. 2009; 66 (2): 132-41.
17. Greenberg S A, Pinkus J L, Amato A A, Kristensen T, Dorfman D M. Association of inclusion body myositis with T cell large granular lymphocytic leukaemia. Brain: a journal of neurology. 2016; 139:1348-1360.
18. Guthmann M D, Tal M, Pecht I. A new member of the C-type lectin family is a modulator of the mast cell secretory response. Int Arch Allergy Immunol. 1995; 107 (1-3): 82-6.
19. Hijnen D, Knol E F, Gent Y Y, Giovannone B, Beijn S J, Kupper T S, et al. CD8 (+) T cells in the lesional skin of atopic dermatitis and psoriasis patients are an important source of IFN-gamma, IL-13, IL-17, and IL-22. J Invest Dermatol. 2013; 133 (4): 973-9.
20. Hofmann M, Schweier O, Pircher H. Different inhibitory capacities of human and mouse KLRG1 are linked to distinct disulfide-mediated oligomerizations. Eur J Immunol. 2012; 42 (9): 2484-90.
21. Kita H. Autoreactive CD8-specific T-cell response in primary biliary cirrhosis. Hepatology research: the official journal of the Japan Society of Hepatology. 2007; 37 Suppl 3: S402-5.
22. Koch S, Larbi A, Derhovanessian E, Ozcelik D, Naumova E, Pawelec G. Multiparameter flow cytometric analysis of CD4 and CD8 T cell subsets in young and old people. Immun Ageing. 2008; 5:6.
23. Lamy T, Loughran T P, Jr. How I treat LGL leukemia. Blood. 2011; 117 (10): 2764-74.
24. Legat A, Speiser D E, Pircher H, Zehn D, Fuertes Marraco S A. Inhibitory Receptor Expression Depends More Dominantly on Differentiation and Activation than "Exhaustion" of Human CD8 T Cells. Front Immunol. 2013; 4:455.
25. Melis L, Van Praet L, Pircher H, Venken K, Elewaut D. Senescence marker killer cell lectin-like receptor G1 (KLRG1) contributes to TNF-alpha production by interaction with its soluble E-cadherin ligand in chronically inflamed joints. Ann Rheum Dis. 2014; 73 (6): 1223-31.
26. Muller S, Lory J, Corazza N, Griffiths G M, Z'Graggen K, Mazzucchelli L, et al. Activated CD4+ and CD8+ cytotoxic cells are present in increased numbers in the intestinal mucosa from patients with active inflammatory bowel disease. The American journal of pathology. 1998; 152 (1): 261-8.
27. Okajima M, Wada T, Nishida M, Yokoyama T, Nakayama Y, Hashida Y, et al. Analysis of T cell receptor Vbeta diversity in peripheral CD4 and CD8 T lymphocytes in patients with autoimmune thyroid diseases. Clinical and experimental immunology. 2009; 155 (2): 166-72.
28. Schirmer M, Goldberger C, Wurzner R, Duftner C, Pfeiffer K P, Clausen J, et al. Circulating cytotoxic CD8 (+) CD28 (−) T cells in ankylosing spondylitis. Arthritis research. 2002; 4 (1): 71-6.
29. Takata K, Hong M E, Sitthinamsuwan P, Loong F, Tan S Y, Liau J Y, et al. Primary cutaneous NK/T-cell lymphoma, nasal type and CD56-positive peripheral T-cell lymphoma: a cellular lineage and clinicopathologic study of 60 patients from Asia. The American journal of surgical pathology. 2015; 39 (1): 1-12.
30. Tessmer M S, Fugere C, Stevenaert F, Naidenko O V, Chong H J, Leclercq G, et al. KLRG1 binds cadherins and preferentially associates with SHIP-1. International immunology. 2007; 19 (4): 391-400.
31. Trevino M A, Teixeiro E, Bragado R. CD8+ T cells oligoclonally expanded in synovial fluid at onset of spondyloarthropathy selectively proliferate in response to self-antigens: characterization of cell specificities in nonclonal populations. The Journal of rheumatology. 2004; 31 (10): 1962-72.
32. Voehringer D, Koschella M, Pircher H. Lack of proliferative capacity of human effector and memory T cells expressing killer cell lectinlike receptor G1 (KLRG1). Blood. 2002; 100 (10): 3698-702.
33. Xing L, Dai Z, Jabbari A, Cerise J E, Higgins C A, Gong W, et al. Alopecia areata is driven by cytotoxic T lymphocytes and is reversed by JAK inhibition. Nat Med. 2014; 20 (9): 1043-9.
34. Willinger, T. et al. Molecular Signatures Distinguish Human Central Memory from Effector Memory CD8 T Cell Subsets. J Immunol 2005; 175:5895-5903; doi: 10.4049/jimmunol. 175.9.5895 http://www.jimmunol.org/content/175/9/5895.
35. Yamauchi C, Fujii S, Kimura T, Kuwata T, Wada N, Mukai H, Matsumoto N, Fukayama M, Ochiai A. E-cadherin expression on human carcinoma cell affects trastuzumab-mediated antibody-dependent cellular cytotoxicity through killer cell lectin-like receptor G1 on natural killer cells. Int J Cancer. 2011; 128 (9): 2125-37.
36. Yu H G, Lee D S, Seo J M, Ahn J K, Yu Y S, Lee W J, et al. The number of CD8+ T cells and NKT cells increases in the aqueous humor of patients with Behcet's uveitis. Clinical and experimental immunology. 2004; 137 (2): 437-43.

37. Zang Y C, Li S, Rivera V M, Hong J, Robinson R R, Breitbach W T, et al. Increased CD8+ cytotoxic T cell responses to myelin basic protein in multiple sclerosis. Journal of immunology. 2004; 172 (8): 5120-7.

What is claimed is:

1. A method of treating a disorder associated with excess or unwanted killer cell lectin-like receptor G1 (KLRG1) expressing T cells in a subject in need thereof, comprising:

delivering to the subject a therapeutically effective amount of an antibody, or a fragment thereof, that specifically binds to an extracellular domain of KLRG1 without interfering with binding by E-cadherin, N-cadherin, or R-cadherin to the extracellular domain of KLRG1 and comprises a heavy chain variable region comprising three heavy chain complementarity determining regions (CDR-H1, CDR-H2 and CDR-H3) and a light chain variable region comprising three light chain complementary determining regions (CDR-L1, CDR-L2 and CDR-L3), wherein said antibody, or fragment thereof, comprises i) SEQ ID NO:16 (CDR-H1), SEQ ID NO:17 (CDR-H2), SEQ ID NO:18 (CDR-H3), SEQ ID NO:19 (CRD-L1), SEQ ID NO:20 (CDR-L2), and SEQ ID NO:21 (CDR-L3);
ii) SEQ ID NO:22 (CDR-H1), SEQ ID NO:23 (CDR-H2), SEQ ID NO:24 (CDR-H3), SEQ ID NO:25 (CRD-L1), SEQ ID NO:26 (CDR-L2), and SEQ ID NO:27 (CDR-L3);
iii) SEQ ID NO:28 (CDR-H1), SEQ ID NO:29 (CDR-H2), SEQ ID NO:30 (CDR-H3), SEQ ID NO:31 (CRD-L1), SEQ ID NO:32 (CDR-L2), and SEQ ID NO:33 (CDR-L3);
iv) SEQ ID NO:34 (CDR-H1), SEQ ID NO:35 (CDR-H2), SEQ ID NO:36 (CDR-H3), SEQ ID NO:37 (CRD-L1), SEQ ID NO:38 (CDR-L2), and SEQ ID NO:39 (CDR-L3);
v) SEQ ID NO:40 (CDR-H1), SEQ ID NO:41 (CDR-H2), SEQ ID NO:42 (CDR-H3), SEQ ID NO:43 (CRD-L1), SEQ ID NO:44 (CDR-L2), and SEQ ID NO:45 (CDR-L3); or
vi) SEQ ID NO:46 (CDR-H1), SEQ ID NO:47 (CDR-H2), SEQ ID NO:48 (CDR-H3), SEQ ID NO:49 (CRD-L1), SEQ ID NO:50 (CDR-L2), and SEQ ID NO:51 (CDR-L3);

and wherein the delivery of the therapeutically effective amount of the antibody, or fragment thereof, depletes the excess or unwanted KLRG1 expressing T cells in the subject.

2. The method of claim 1,
wherein the disorder comprises a transplant disorder, and
wherein the delivery to the subject depletes KLRG1 expressing pathogenic T cells and/or NK cells attacking transplanted tissues in the subject.

3. The method of claim 1,
wherein the disorder comprises an autoimmune disease, and
wherein the delivery to the subject depletes KLRG1 expressing pathogenic T cells and/or NK cells attacking self-tissues in the subject.

4. The method of claim 1, wherein the disorder is inclusion body myositis (IBM).

5. The method of claim 1, wherein the antibody, or a fragment thereof, comprises:

a) the three heavy chain complementarity determining regions and the three light chain complementarity determining regions of i); wherein the heavy chain variable region comprises SEQ ID NO:4 or a sequence at least 90% identical to SEQ ID NO:4; and the light chain variable region comprises SEQ ID NO:5 or a sequence at least 90% identical to SEQ ID NO:5;
b) the three heavy chain complementarity determining regions and the three light chain complementarity determining regions of ii); wherein the heavy chain variable region comprises SEQ ID NO:6 or a sequence at least 90% identical to SEQ ID NO:6; and the light chain variable region comprises SEQ ID NO:7 or a sequence at least 90% identical to SEQ ID NO:7;
c) the three heavy chain complementarity determining regions and the three light chain complementarity determining regions of iii); wherein the heavy chain variable region comprises SEQ ID NO:8 or a sequence at least 90% identical to SEQ ID NO:8; and the light chain variable region comprises SEQ ID NO:9 or a sequence at least 90% identical to SEQ ID NO:9;
d) the three heavy chain complementarity determining regions and the three light chain complementarity determining regions of iv); wherein the heavy chain variable region comprises SEQ ID NO: 10 or a sequence at least 90% identical to SEQ ID NO:10; and the light chain variable region comprises SEQ ID NO: 11 or a sequence at least 90% identical to SEQ ID NO:11;
e) the three heavy chain complementarity determining regions and the three light chain complementarity determining regions of v); wherein the heavy chain variable region comprises SEQ ID NO: 12 or a sequence at least 90% identical to SEQ ID NO:12; and the light chain variable region comprises SEQ ID NO: 13 or a sequence at least 90% identical to SEQ ID NO:13;
f) the three heavy chain complementarity determining regions and the three light chain complementarity determining regions of vi); wherein the heavy chain variable region comprises SEQ ID NO: 14 or a sequence at least 90% identical to SEQ ID NO:14; and the light chain variable region comprises SEQ ID NO:15 or a sequence at least 90% identical to SEQ ID NO:15;
g) the three heavy chain complementarity determining regions and the three light chain complementarity determining regions of ii); wherein the heavy chain variable region comprises SEQ ID NO:52 or a sequence at least 90% identical to SEQ ID NO:52; and the light chain variable region comprises SEQ ID NO:53 or a sequence at least 90% identical to SEQ ID NO:53; or
h) the three heavy chain complementarity determining regions and the three light chain complementarity determining regions of iii); wherein the heavy chain variable region comprises SEQ ID NO:54 or a sequence at least 90% identical to SEQ ID NO:54; and the light chain variable region v SEQ ID NO:55 or a sequence at least 90% identical to SEQ ID NO:55.

6. The method of claim 1, wherein the antibody, or a fragment thereof, comprises a monoclonal antibody, or a fragment thereof.

7. The method of claim 6, wherein the monoclonal antibody, or a fragment thereof, specifically binds the epitope PLNFSRI (SEQ ID NO:56) or a fragment thereof, comprising at least five contiguous amino acids.

8. The method of claim 6, wherein the monoclonal antibody, or a fragment thereof, comprises a chimeric antibody, or a fragment thereof.

9. The method of claim 6, wherein the monoclonal antibody, or a fragment thereof, comprises a humanized antibody or a fragment thereof.

10. A method of treating cancer in a subject, wherein the cancer comprises cancer cells that express KLRG1, the method comprising:

delivering to the subject a therapeutically effective amount of an antibody, or a fragment thereof, that specifically binds to an extracellular domain of KLRG1 without interfering with binding by E-cadherin, N-cadherin, or R-cadherin to the extracellular domain of KLRG1, wherein the delivery to the subject depletes the cancer cells expressing KLRG1, and wherein said antibody, or fragment thereof, comprises a heavy chain variable region comprising three heavy chain complementarity determining regions (CDR-H1, CDR-H2 and CDR-H3) and a light chain variable region comprising three light chain complementary determining regions (CDR-L1, CDR-L2 and CDR-L3) comprising:

i) SEQ ID NO:16 (CDR-H1), SEQ ID NO:17 (CDR-H2), SEQ ID NO:18 (CDR-H3), SEQ ID NO:19 (CRD-L1), SEQ ID NO:20 (CDR-L2), and SEQ ID NO:21 (CDR-L3);

ii) SEQ ID NO:22 (CDR-H1), SEQ ID NO:23 (CDR-H2), SEQ ID NO:24 (CDR-H3), SEQ ID NO:25 (CRD-L1), SEQ ID NO:26 (CDR-L2), and SEQ ID NO:27 (CDR-L3);

iii) SEQ ID NO:28 (CDR-H1), SEQ ID NO:29 (CDR-H2), SEQ ID NO:30 (CDR-H3), SEQ ID NO:31 (CRD-L1), SEQ ID NO:32 (CDR-L2), and SEQ ID NO:33 (CDR-L3);

iv) SEQ ID NO:34 (CDR-H1), SEQ ID NO:35 (CDR-H2), SEQ ID NO:36 (CDR-H3), SEQ ID NO:37 (CRD-L1), SEQ ID NO:38 (CDR-L2), and SEQ ID NO:39 (CDR-L3);

v) SEQ ID NO:40 (CDR-H1), SEQ ID NO:41 (CDR-H2), SEQ ID NO:42 (CDR-H3), SEQ ID NO:43 (CRD-L1), SEQ ID NO:44 (CDR-L2), and SEQ ID NO:45 (CDR-L3); or vi) SEQ ID NO:46 (CDR-H1), SEQ ID NO:47 (CDR-H2), SEQ ID NO:48 (CDR-H3), SEQ ID NO:49 (CRD-L1), SEQ ID NO:50 (CDR-L2), and SEQ ID NO:51 (CDR-L3).

11. The method of 10, wherein the cancer is a leukemia.

12. The method of 11, wherein the leukemia is T cell large granular lymphocytic leukemia (T-LGLL).

13. The method of claim 10, wherein the antibody, or a fragment thereof, comprises:

a) the three heavy chain complementarity determining regions and the three light chain complementarity determining regions of i); wherein the heavy chain variable region comprises SEQ ID NO:4 or a sequence at least 90% identical to SEQ ID NO:4; and the light chain variable region comprises SEQ ID NO:5 or a sequence at least 90% identical to SEQ ID NO:5;

b) the three heavy chain complementarity determining regions and the three light chain complementarity determining regions of ii); wherein the heavy chain variable region comprises SEQ ID NO:6 or a sequence at least 90% identical to SEQ ID NO:6; and the light chain variable region comprises SEQ ID NO:7 or a sequence at least 90% identical to SEQ ID NO:7;

c) the three heavy chain complementarity determining regions and the three light chain complementarity determining regions of iii); wherein the heavy chain variable region comprises SEQ ID NO:8 or a sequence at least 90% identical to SEQ ID NO:8; and the light chain variable region comprises SEQ ID NO:9 or a sequence at least 90% identical to SEQ ID NO:9;

d) the three heavy chain complementarity determining regions and the three light chain complementarity determining regions of iv); wherein the heavy chain variable region comprises SEQ ID NO: 10 or a sequence at least 90% identical to SEQ ID NO:10; and the light chain variable region comprises SEQ ID NO: 11 or a sequence at least 90% identical to SEQ ID NO:11;

e) the three heavy chain complementarity determining regions and the three light chain complementarity determining regions of v); wherein the heavy chain variable region comprises SEQ ID NO: 12 or a sequence at least 90% identical to SEQ ID NO:12; and the light chain variable region comprises SEQ ID NO:13 or a sequence at least 90% identical to SEQ ID NO:13;

f) the three heavy chain complementarity determining regions and the three light chain complementarity determining regions of vi); wherein the heavy chain variable region comprises SEQ ID NO: 14 or a sequence at least 90% identical to SEQ ID NO:14; and the light chain variable region comprises SEQ ID NO: 15 or a sequence at least 90% identical to SEQ ID NO:15;

g) the three heavy chain complementarity determining regions and the three light chain complementarity determining regions of ii); wherein the heavy chain variable region comprises SEQ ID NO:52 or a sequence at least 90% identical to SEQ ID NO:52; and the light chain variable region comprises SEQ ID NO:53 or a sequence at least 90% identical to SEQ ID NO:53; or h) the three heavy chain complementarity determining regions and the three light chain complementarity determining regions of iii); wherein the heavy chain variable region comprises SEQ ID NO:54 or a sequence at least 90% identical to SEQ ID NO:54; and the light chain variable region v SEQ ID NO:55 or a sequence at least 90% identical to SEQ ID NO:55.

14. The method of claim 10, wherein the antibody, or a fragment thereof, comprises a monoclonal antibody, or a fragment thereof.

15. The method of claim 14, wherein the monoclonal antibody, or a fragment thereof, specifically binds the epitope PLNFSRI (SEQ ID NO:56), or a fragment thereof comprising at least five contiguous amino acids.

16. The method of claim 14, wherein the monoclonal antibody, or a fragment thereof, comprises a chimeric antibody, or a fragment thereof.

17. The method of claim 14, wherein the monoclonal antibody, or a fragment thereof, comprises a humanized antibody or a fragment thereof.

18. An adjunct therapy for treatment of cancer in a subject, wherein the subject is undergoing checkpoint therapy and the cancer expresses KLRG1, the adjunct therapy comprising:

delivering to the subject a therapeutically effective amount of an antibody, or a fragment thereof, that specifically binds to an extracellular domain of KLRG1 without interfering with binding by E-cadherin, N-cadherin, or R-cadherin to the extracellular domain of KLRG1, wherein the delivery depletes KLRG1 expressing pathogenic T cells and/or NK cells attacking self-tissues in the subject, wherein the antibody, or a fragment thereof, comprises: a heavy chain variable region comprising three heavy chain complementarity determining regions (CDR-H1, CDR-H2 and CDR-H3) and a light chain variable region comprising three light chain complementary determining regions (CDR-L1, CDR-L2 and CDR-L3) comprising:

i) SEQ ID NO:16 (CDR-H1), SEQ ID NO:17 (CDR-H2), SEQ ID NO:18 (CDR-H3), SEQ ID NO:19 (CRD-L1), SEQ ID NO:20 (CDR-L2), and SEQ ID NO:21 (CDR-L3);
ii) SEQ ID NO:22 (CDR-H1), SEQ ID NO:23 (CDR-H2), SEQ ID NO:24 (CDR-H3), SEQ ID NO:25 (CRD-L1), SEQ ID NO:26 (CDR-L2), and SEQ ID NO:27 (CDR-L3);
iii) SEQ ID NO:28 (CDR-H1), SEQ ID NO:29 (CDR-H2), SEQ ID NO:30 (CDR-H3), SEQ ID NO:31 (CRD-L1), SEQ ID NO:32 (CDR-L2), and SEQ ID NO:33 (CDR-L3);
iv) SEQ ID NO:34 (CDR-H1), SEQ ID NO:35 (CDR-H2), SEQ ID NO:36 (CDR-H3), SEQ ID NO:37 (CRD-L1), SEQ ID NO:38 (CDR-L2), and SEQ ID NO:39 (CDR-L3);
v) SEQ ID NO:40 (CDR-H1), SEQ ID NO:41 (CDR-H2), SEQ ID NO:42 (CDR-H3), SEQ ID NO:43 (CRD-L1), SEQ ID NO:44 (CDR-L2), and SEQ ID NO:45 (CDR-L3); or
vi) SEQ ID NO:46 (CDR-H1), SEQ ID NO:47 (CDR-H2), SEQ ID NO:48 (CDR-H3), SEQ ID NO:49 (CRD-L1), SEQ ID NO:50 (CDR-L2), and SEQ ID NO:51 (CDR-L3).

19. A method of depleting KLRG1 expressing cells in a mixed population of cells, wherein the KLRG1 expressing cells in said mixed population of cells comprise one or more cells selected from the group consisting of T cells, NK cells and cancer cells, the method comprising:
   delivering to said mixed population of cells an effective amount of an antibody, or a fragment thereof, that specifically binds to KLRG1 and depletes KLRG1 expressing T cells and/or NK cells and/or cancer cells, thereby depleting KLRG1 expressing T cells and/or NK cells and/or cancer cells in the mixed population of cells,
   wherein the antibody, or a fragment thereof, comprises: a heavy chain variable region comprising three heavy chain complementarity determining regions (CDR-H1, CDR-H2 and CDR-H3) and a light chain variable region comprising three light chain complementary determining regions (CDR-L1, CDR-L2 and CDR-L3) comprising:
   i) SEQ ID NO:16 (CDR-H1), SEQ ID NO:17 (CDR-H2), SEQ ID NO:18 (CDR-H3), SEQ ID NO:19 (CRD-L1), SEQ ID NO:20 (CDR-L2), and SEQ ID NO:21 (CDR-L3);
   ii) SEQ ID NO:22 (CDR-H1), SEQ ID NO:23 (CDR-H2), SEQ ID NO:24 (CDR-H3), SEQ ID NO:25 (CRD-L1), SEQ ID NO:26 (CDR-L2), and SEQ ID NO:27 (CDR-L3);
   iii) SEQ ID NO:28 (CDR-H1), SEQ ID NO:29 (CDR-H2), SEQ ID NO:30 (CDR-H3), SEQ ID NO:31 (CRD-L1), SEQ ID NO:32 (CDR-L2), and SEQ ID NO:33 (CDR-L3);
   iv) SEQ ID NO:34 (CDR-H1), SEQ ID NO:35 (CDR-H2), SEQ ID NO:36 (CDR-H3), SEQ ID NO:37 (CRD-L1), SEQ ID NO:38 (CDR-L2), and SEQ ID NO:39 (CDR-L3);
   v) SEQ ID NO:40 (CDR-H1), SEQ ID NO:41 (CDR-H2), SEQ ID NO:42 (CDR-H3), SEQ ID NO:43 (CRD-L1), SEQ ID NO:44 (CDR-L2), and SEQ ID NO:45 (CDR-L3); or
   vi) SEQ ID NO:46 (CDR-H1), SEQ ID NO:47 (CDR-H2), SEQ ID NO:48 (CDR-H3), SEQ ID NO:49 (CRD-L1), SEQ ID NO:50 (CDR-L2), and SEQ ID NO:51 (CDR-L3).

* * * * *